United States Patent [19]

Hong et al.

[11] Patent Number: 5,633,262
[45] Date of Patent: May 27, 1997

[54] QUINOLINE CARBOXYLIC ACID DERIVATIVES HAVING 7-(4-AMINO-METHYL-3-OXIME) PYRROLIDINE SUBSTITUENT AND PROCESSES FOR PREPARING THEREOF

[75] Inventors: Chang Y. Hong, Daejeon; Young K. Kim, Kyungki-do; Jay H. Chang, Daejeon; Se H. Kim, Seoul; Hoon Choi, Daejeon; Do H. Nam, Daejeon; Jin H. Kwak, Daejeon; Yi N. Jeong, Daejeon; Jeong I. Oh, Daejeon; Mu Y. Kim, Daejeon, all of Rep. of Korea

[73] Assignee: LG Chemical Ltd., Seoul, Rep. of Korea

[21] Appl. No.: 490,978

[22] Filed: Jun. 15, 1995

[30] Foreign Application Priority Data

Jun. 16, 1994 [KR] Rep. of Korea ............ 94-13604
Dec. 30, 1994 [KR] Rep. of Korea ............ 94-39915
Dec. 30, 1994 [KR] Rep. of Korea ............ 94-39930

[51] Int. Cl.$^6$ ............ A61K 31/44; C07D 471/02
[52] U.S. Cl. ............ 514/300; 546/123
[58] Field of Search ............ 546/156, 123; 514/312, 300

[56] References Cited

FOREIGN PATENT DOCUMENTS 1-100165  4/1989  Japan.
0541086   5/1993  Japan.

OTHER PUBLICATIONS

CA114:164195r Preparation of . . . as antibacterials. Kuramoto et al., p. 775, 1991.
CA119:203318h Preparation of . . . antibacterial agents. Ochi et al., p. 884, 1993.
Lesher et al., "1, 8–Naphthyridine Derivatives. A New Class of Chemotherapeutic Agents", *J. Med. Chem.*, vol. 5, pp. 1063–1065, 1962.
Koga et al., "Structure–Activity Relationships of Antibacterial 6,7– and 7,8–Disubstituted 1–Alkyl–1,4–dihydro–4–oixoquinoline–3–carboxylic Acids", *J. Med. Chem.*, vol. 23, pp. 1358–1363, 1980.
Wise et al., "In Vitro Activity of Bay 09867, a New Quinoloine Derivative, Compared with Those of Other Antimicrobial Agents", *J. Antimicrob. Agents Chemother.*, vol. 23, pp. 559–564, 1983.
Sato et al., "In Vitro and In Vivo Activity of DL–8280, a New Oxazine Derivative", *J. Antimicrob. Agents Chemother*, vol. 23, pp. 548–553, 1982.
Rosen et al., "Design, Synthesis, and Properties of (4S)–7–(4–Amino–2–substituted–pyrrolidin–1–yl) quinolone–3–carboxylic Acids", *J. Med. Chem.*, vol. 31, pp. 1598–1611, 1988.

Matsumoto et al., "AT–3295, a New Pyridonecarboxylic Acid Derivative with Potent Antibacterial Activity: Synthesis and Structure–activity Relationships", *Proceedings of the 14th International Congress of Chemotheraphy*, pp. 1519–1520, 1985.
Cooper et al., "Preparation and in Vitro and in Vivo Evaluation of Quinolones with Selective Activity against Gram–Positive Organisms", *J. Med. Chem.*, vol. 35, pp. 1392–1398, 1992.
Domagala et al., "Synthesis and Biological Activity of 5–Amino–and 5–Hydroxyquinolones, and the Overwhelming Influence of the Remote N– Substituent in Determining the Structure–Activity Relationship", *J. Med. Chem.*, vol. 34, pp. 1142–1154, 1991.
Domagala et al., "1–Substituted, 7–[3–[(Ethylamoni)methyl]–1–pyrrolidinyl]–6,8–difluoror–1, 4–dihydro–4–oxo–3–quinolinecarboxylic Acids. New Quantititative Structure–Activity Relationships at N' for the Quinolone Antibacterials", *J. Med. Chem.*, vol. 31, pp. 991–1001, 1988.
Bouzard et al., "Fluoronaphthyridines as Antibacterial Agents. 4. Synthesis and Structure–Activity Relationships of 5–Substituted–6–fluoro–7–(cycloalkylamino)–1, 4–dihydro–4–oxo–1,8–naphthyridine–3–carboxylic Acids", *J. Med. Chem.*, vol. 35, pp. 518–525, 1992.
Parikh et al., "Sulfur Trioxide in the Oxidation of Alcohols by Dimethyl Sulfoxide", *JACS.*, vol. 89, pp. 5505–5507, 1967.

*Primary Examiner*—Joseph McKane
*Attorney, Agent, or Firm*—Banner & Witcoff, Ltd.

[57] ABSTRACT

The present invention relates to a novel quinolone compound having an excellent antibacterial activity. More specifically, the present invention relates to a novel quinoline(naphthyridine)carboxylic acid derivative represented by the following formula (I), which has an 4-aminomethyl-3-oximepyrrolidine substituent on 7-position of the quinolone nucleus and shows a superior antibacterial activity in contrast to the known quinolone antibacterial agents having a weak activity against gram-positive bacterial strains and also has a broad antibacterial spectrum and a highly improved pharmacokinetic property:

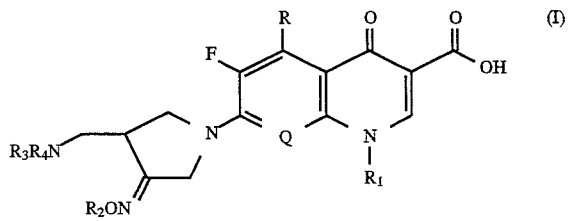

wherein R, $R_1$, $R_2$, $R_3$, $R_4$ and Q are defined as described in the specification.

6 Claims, No Drawings

QUINOLINE CARBOXYLIC ACID DERIVATIVES HAVING 7-(4-AMINO-METHYL-3-OXIME) PYRROLIDINE SUBSTITUENT AND PROCESSES FOR PREPARING THEREOF

BACKGROUND OF INVENTION

1. Field of Invention

The present invention relates to a novel quinoline (naphthyridine)carboxylic acid derivative having an excellent antibacterial activity. More specifically, the present invention relates to a novel quinoline(paphthyridine) carboxylic acid derivative represented by the following formula (I), which has an 4-aminomethyl-3-oximepyrrolidine substituent on 7-position of the quinolone, nucleus and shows a superior antibacterial activity in contrast to the known quinolone antibacterial agents and also has a broad antibacterial spectrum and a highly improved pharmacokinetic property:

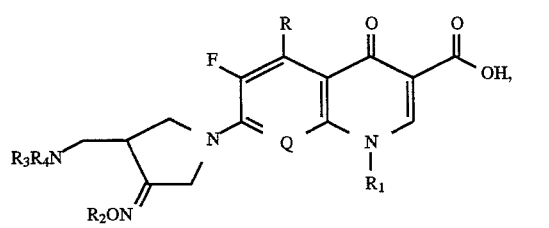

and its pharmaceutically acceptable non-toxic salt, its physiologically hydrolyzable ester, solvate and isomer; in which R represents hydrogen, methyl or amino;

Q represents C—H, C—F, C—Cl, C—OH, C—CH$_3$, C—O—CH$_3$ or N;

$R_1$ represents cyclopropyl, ethyl, or phenyl which is substituted with one or more fluorine atom(s);

$R_2$ represents one of the following a) through e):
  a) hydrogen, straight or branched $C_1$–$C_4$ alkyl, cyclopropyl, cyclopropylmethyl, $C_3$–$C_6$ alkynyl, 2-haloethyl, methoxymethyl, methoxycarbonylmethyl, aryl or allyl,
  b) a group of the following formula (1),

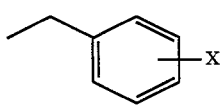

wherein X represents hydrogen, 2, 3 or 4-fluoro, cyano, nitro, methoxy, $C_1$–$C_4$ alkyl, or 2,4-difluoro, c) a group of the following formula (2),

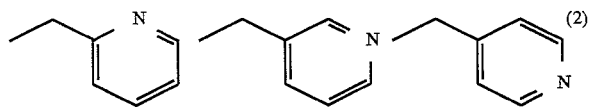

d) a heteroarylmethyl of the following formula (3),

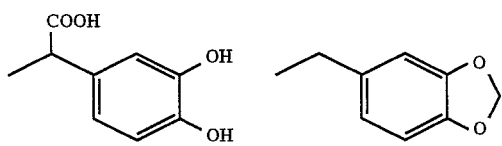

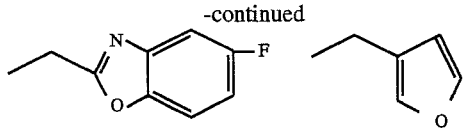

e) a group of the following formula (4),

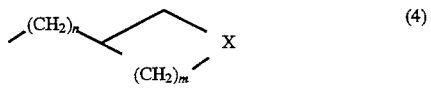

wherein n denotes 0 or 1, m denotes 0, 1 or 2, and X represents methylene, O or N, and $R_3$ and $R_4$ independently of one another represent hydrogen or $C_1$–$C_3$ alkyl or $R_3$ and $R_4$ together with a nitrogen atom to which they are attached can form a ring.

The present invention also relates to a process for preparing the compound of formula (I), as defined above, and an antibacterial composition comprising the compound of formula (I) as an active component.

2. Background Art

Since in 1962 nalidixic acid was first introduced as an agent for treating urinary tract infection (see, G. Y. Lesher, et al., J. Med. Chem. 5, 1063–1065 (1962)), numerous quinoline carboxylic acid antibacterial agents, including oxolinic acid, rosoxacin, pipemidic acid, etc., have been developed. However, these early-stage antibacterial agents have a little activity against gram-positive bacterial strains and thus have been used only against gram-negative strains.

Recently, norfloxacin which is the quinolone compound having a fluorine on 6-position has been newly developed (see, H. Koga, et al., J. Med. Chem., 23, 1358–1363 (1980)), and thereafter an extensive study to develop various quinolone antabacterial compounds has been conducted. However, since norfloxacin has a weak antibacterial activity against gram-positive strains and shows poor distribution and absorption in living body, it has been used only for treatment of diseases including urinary tract infections, gastro-intestinal infections, sexually transmitted diseases and the like. Thereafter, ciprofloxacin (see, R. Wise, et al., J. Antimicrob. Agents Chemother., 23, 559 (1983)), ofloxacin (see, K. Sata, et al., Antimicrob. Agents Chemother., 22, 548 (1982)) and the like have been developed. These antibacterial agents have a superior and broad antibacterial activity in comparison with the early-stage antibacterial compounds, and therefore, have been widely and practically used for treatment of diseases in clinical field.

The compounds in use or under clinical test include mainly the derivatives having a piperazine substituent on 7-position of the quinolone nucleus as in ciprofloxacin or ofloxacin. However, as a result of the study to develop quinolone compounds having a more potent and broad antibacterial activity it has been disclosed that a compound having an 3-amino or 3-aminomethylpyrrolidine group introduced into 7-position has an increased activity against gram-positive strains, in comparison with the compounds having 7-piperazine group, while maintaining a potent activity against gram-negative strains. However, unfortunately, the compounds having pyrrolidine substituent have a low solubility in water in comparison with the compounds having piperazine substituent, and thus their in-vivo antibacterial activity is not so high as the in-vitro activity. Accordingly, numerous study has been continuously conducted to improve the disadvantage of the compounds having pyrrolidine substituent, that is, to increase the solubility in water and to improve the pharmacokinetic property.

As a result, many reports of such study have been made. For example, it has been disclosed that ((2S, 4S)-4-amino-2-methylpyrrolidinyl)naphthyridine derivatives (see, Rosen, T., Chu, D. T. W. etc. J. Med. Chem. 1988, 31, 1598–1611) or (trans-3-amino-4-methylpyrrolidinyl)naphthyridine derivatives (see, Matsumoto, J. et al., Proceedings of the 14th International Congress of Chemotherapy; Ishigami, J., Ed.; University of Tokyo Press: Tokyo, 1985; pp 1519–1520) shows a 20 to 40 times increase in water-solubility, an increased bioavailability and an improved pharmacokinetic property, in comparison with the compounds having no methyl group, with a similar in-vitro antibacterial activity.

In addition, an attempt to improve the disadvantage of the prior quinolone compounds including a relatively low antibacterial activity against gram-positive strains, a low water-solubility and a poor pharmacokinetic property has been made by introducing different functional groups, instead of amino group, into the pyrrolidine or piperazine moiety. As one of such attempt, some compounds having an oxime group introduced into the 7-amine moiety of quinolone compounds have been reported. For example, the researchers of Abbott have reported in a scientific Journal, J. Med. Chem., 1992, 35, 1392–1398, that the quinolone compound having the following general formula [A] wherein 3-oxime (or methyloxime)pyrrolidine group or 4-oxime(or methyloxime)piperidine group is substituted on 7-position of quinolone nucleus exhibits a good antibacterial activity against gram-positive strains:

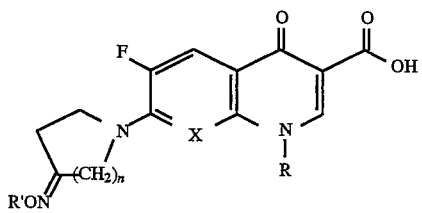

in which

R represents cyclopropyl or 2,4-difluorophenyl;
R' represents hydrogen or methyl;
X represents C—H, C—F or N; and
n denotes 1 or 2.

The compound [A] has some disadvantages that it shows a good antibacterial activity against gram-positive strains but a relatively weak activity against gram-negative strains, and also has a relatively low antibacterial activity in in-vivo test.

In addition, Japanese Laid-open Patent Publication No. (Hei) 01–100165 (1989) discloses the compound having the following general formula [B]:

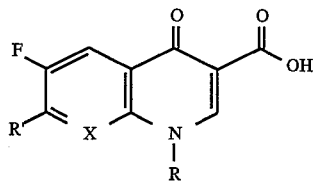

in which

R represents cyclopropyl, 2,4-difluorophenyl or 4-hydroxyphenyl;
X represents C—H, C—F or C—Cl; and
R' represents oxime or hydroxyaminopyrrolidine-derived substituent.

Specifically, in said Japanese laid-open publication the oxime or hydroxyaminopyrrolidine-derived groups as R' substituent are very broadly disclosed. However, only the 3-hydroxyaminopyrrolidine [the following formula (a)], 3-methoxyaminopyrrolidine [the following formula (b)], 3-amino-4-methoxyaminopyrrolidine [the following formula (c)], 3-oximepyrrolidine [the following formula (d)] and 3-methyloximepyrrolidine [the following formula (e)] groups are specifically exemplified but the pyrrolidine substituent having both 3-oxime and 4-aminomethyl groups has never been specifically mentioned.

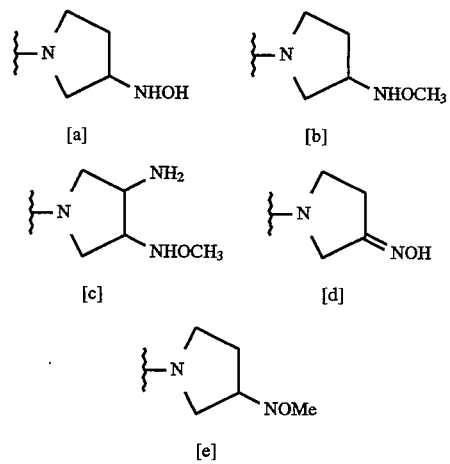

Further, European Early Patent Publication No. 0 541 086 discloses the quinolone compound having the following general formula [C]:

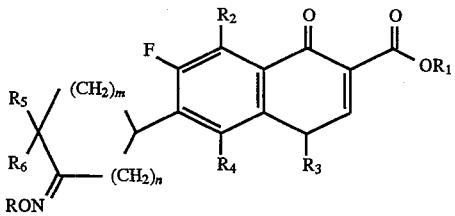

in which

R and $R_1$ independently of one another represent hydrogen or $C_1$–$C_5$ alkyl;

$R_2$ represents hydrogen, amino, fluoro or hydroxy;

$R_3$ represents $C_3$–$C_7$ cycloalkyl;

$R_4$ represents methoxy or fluoro;

$R_5$ and $R_6$ can be identical with or different from each other and independently of one another represent hydrogen or alkyl, or $R_5$ and $R_6$ together can form $C_3$–$C_5$ cycloalkyl;

m denotes 0 or 1; and n denotes an integer of 1 to 3.

Among the compounds [C] disclosed in said European early patent publication the typical substituent on 7-position of quinolone nucleus is a group having the following structure:

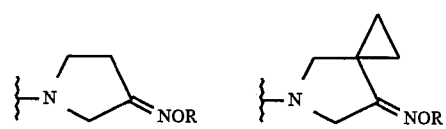

-continued

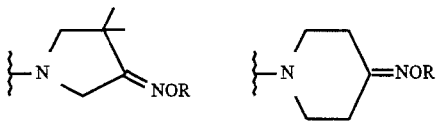

However, the compound of formula [C] does not include any compound having both oxime group and aminomethyl group on 7-position, and therefore, is different from the compound of the present invention.

The common characteristic feature of the known oxime or hydroxyamine-derived compounds as mentioned above is that they exhibit a good activity against gram-positive strains including MRSA (Methicillin Resistant *Staphylococcus aureus*) strains in comparison with the early developed quinolone compounds but show a weak activity against gram-negative strains in comparison with the antibacterial agents including ofloxacin or ciprofloxacin. Therefore, it can be said that their antibacterial spectrum may be narrower than that of the known ofloxacin or ciprofloxacin antibacterial compound.

Thus, on the basis of prior art as mentioned above the present inventors have extensively studied to develop the novel oxime-aminomethyl compound, which shows a potent antibacterial activity against broad spectrum pathogenic strains including resistant strains and also exhibits more improved pharmacokinetic properties and high absorption in living body, by introducing various substituted pyrrolidine groups into 7-position of quinoline nucleus and determining pharmacological activities of the resulting compounds. As a result, we have identified that the quinolone compounds having the general formula (I), as defined above, wherein 4-aminomethyl-3-(optionally substituted)oxime-pyrrolidine group is introduced into 7-position of quinoline nucleus can satisfy such purpose, and thus completed the present invention.

Therefore, it is an object of the present invention to provide a novel quinoline(naphthyridine) carboxylic acid derivative of formula (I), as defined above, which shows a potent antibacterial activity against broad pathogenic strains including both gram-positive and gram-negative strains and also has a good pharmacokinetic property.

It is another object of the present invention to provide a process for preparing the novel quinoline(naphthyridine) carboxylic acid derivative of formula (I).

It is a further object of the present invention to provide an antibacterial composition comprising the novel quinoline (naphthyridine)carboxylic acid derivative of formula (I) as an active component.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel quinoline(naphthyridine) carboxylic acid derivative having the following formula (I):

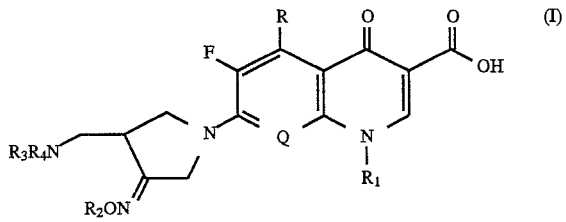

and its pharmaceutically acceptable non-toxic salt, its physiologically hydrolyzable ester, solvate and isomer, in which R represents hydrogen, methyl or amino;

Q represents C—H, C—F, C—Cl, C—OH, C—$CH_3$, C—O—$CH_3$ or N;

$R_1$ represents cyclopropyl, ethyl, or phenyl which is substituted with one or more fluorine atom(s);

$R_2$ represents one of the following a) through e):
  a) hydrogen, straight or branched $C_1$-$C_4$ alkyl, cyclopropyl, cyclopropylmethyl, $C_3$-$C_6$ alkynyl, 2-haloethyl, methoxymethyl, methoxycarbonylmethyl, aryl or allyl,
  b) a group of the following formula (1),

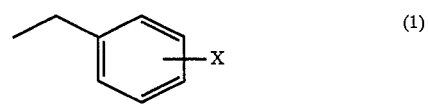

wherein X represents hydrogen, 2, 3 or 4-fluoro, cyano, nitro, methoxy, $C_1$-$C_4$ alkyl, or 2,4-difluoro,
  c) a group of the following formula (2),

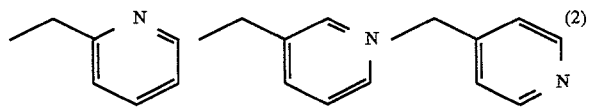

d) a heteroarylmethyl of the following formula (3),

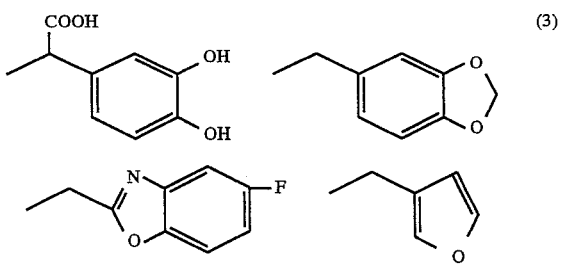

e) a group of the following formula (4),

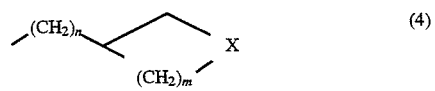

wherein n denotes 0 or 1, m denotes 0, 1 or 2, and X represents methylene, O or N, and $R_3$ and $R_4$ independently of one another represent hydrogen or $C_1$-$C_3$ alkyl or $R_3$ and $R_4$ together with a nitrogen atom to which they are attached can form a ring.

Among the compound of formula (I), as defined above, having a superior antibacterial activity, a broad antibacterial spectrum and an excellent pharmacokinetic property, the preferred compounds include those wherein Q represents C—H, C—F, C—Cl, C—OMe or N, R represents hydrogen or amino, $R_1$ represents cyclopropyl or 2,4-difluorophenyl, $R_2$ represents hydrogen, methyl, ethyl, isopropyl, t-butyl, phenyl, propargyl, homopropargyl, 2-fluoroethyl, benzyl, 2-fluorobenzyl or 2-cyanobenzyl, and $R_3$ and $R_4$ represent hydrogen.

More preferred compounds of formula (I) include those wherein Q represents C—H, C—Cl, C—F or N, R represents hydrogen or amino, $R_1$ represents cyclopropyl, $R_2$ represents methyl, t-butyl, homopropargyl, 2-fluoroethyl, benzyl or 2-fluorobenzyl, and $R_3$ and $R_4$ represent hydrogen.

In the pyrrolidine moiety of the compound of formula (I) the 4-carbon atom on which aminomethyl group is substituted is an assymetric carbon atom and thus can be present in the form of R or S or a mixture of R and S. In addition, due to the presence of (optionally substituted) oxime group on 3-position of pyrrolidine moiety the compound of formula (I) can be present in the form of syn- and anti-isomers depending on their geometric structure. Thus, the present invention also includes all of those geometric isomers and their mixtures.

The compound of formula (I) according to the present invention can form a pharmaceutically acceptable non-toxic salt. Such salt includes a salt with inorganic acids such as hydrochloric acid, hydrobromic acid, phosphoric acid, sulfuric acid, etc., a salt with organic carboxylic acids such as acetic acid, trifluoroacetic acid, citric acid, maleic acid, oxalic acid, succinic acid, benzoic acid, tartaric acid, fumaric acid, mandelic acid, ascorbic acid or malic acid or with sulfonic acids such as methanesulfonic acid, paratoluenesulfonic acid, etc., and a salt with other acids which are generally known and conventionally used in the technical field of quinolone-based compounds. These acid-addition salts can be prepared according to a conventional conversion method.

In the second aspect, the present invention also relates to a process for preparing the novel compound of formula (I).

According to the present invention, the compound of formula (I) can be prepared by reacting a compound of formula (II) with a compound of formula (III) or a salt thereof, as shown in the following reaction scheme 1.

Reaction Scheme 1

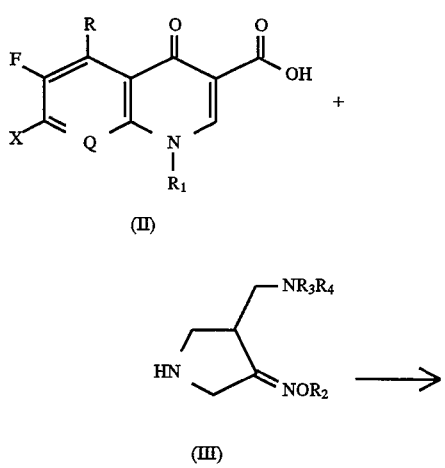

(II)

(III)

-continued
Reaction Scheme 1

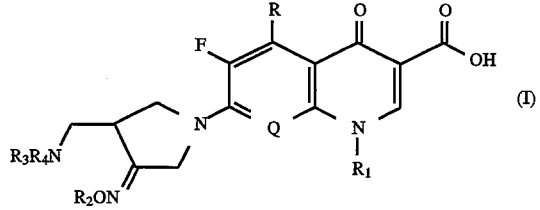

(I)

In the above scheme,

R, $R_1$, $R_2$, $R_3$, $R_4$ and Q are defined as previously described; and

X represents a halogen atom, preferably chlorine, bromine or fluorine.

According to the above reaction scheme 1, the compound of formula (I) according to the present invention can be prepared by stirring the compound of formula (II) and the compound of formula (III) in the presence of a solvent for 1 to 20 hours at the temperature between room temperature and 200° C. with the addition of a suitable base. In this reaction, the compound of formula (III) can be used in the form of a free compound or a salt with an acid such as hydrochloric acid, hydrobromic acid or trifluoroacetic acid.

As the solvent for the above reaction, any solvent which does not adversely affect the reaction can be used. Preferably, acetonitrile, dimethylformamide(DMF), dimethylsulfoxide(DMSO), pyridine or hexamethylphosphoramide(HMPA) can be used.

This reaction is generally conducted in the presence of an acid acceptor. In this case, to increase the reaction efficiency of the relatively expensive starting material (II) the reactant (III) is used in an excessive amount, for example, an equimolar amount to 10 times molar amount, preferably an equimolar amount to 5 times molar amount, with respect to the starting material (II). When the reactant (III) is used in an excessive amount, the unreacted compound of formula (III) which is retained after the reaction can be recoverd and reused in another reaction. The acid acceptor which can be preferably used in this reaction includes inorganic bases such as sodium hydrogen carbonate, potassium carbonate, etc., and organic bases such as triethylamine, diisopropylethylamine, pyridine, N,N-dimethylaniline, N,N-dimethylaminopyridine, 1,8-diazabicyclo[5.4.0]undec-7-ene(DBU), 1,4-diazabicyclo[2.2.2]octane(DABCO), etc.

The compound of formula (I) according to the present invention can also prepared by a method depicted in the following reaction scheme 2, in which a protecting group P is introduced into one of $R_3$ and $R_4$ of the compound of formula (III) wherein $R_3$ and $R_4$ are hydrogen to prepare the compound of formula (III') wherein the amino group is protected with P, the protected compound of formula (III') is reacted with the compound of formula (II) under the same condition as in the reaction scheme 1, and then the resulting compound of formula (I') is deprotected by removing the protecting group P to form the desired compound of formula (I).

Reaction Scheme 2

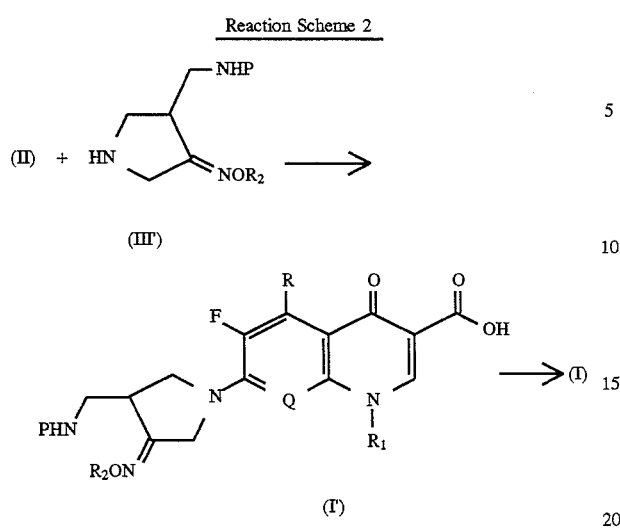

In the above reaction scheme,

R, $R_1$, $R_2$ and Q are defined as previously described; and P represents an amino-protecting group.

In the reaction of the above reaction scheme 2, the compound of formula (III') can be used in the form of a free compound or a salt with hydrochloric acid, hydrobromic acid or trifluoroacetic acid, as in the compound of formula (III) used in the reaction scheme 1.

Any protecting group which is conventionally used in the field of organic chemistry and can be readily removed after the reaction without decomposition of the structure of the desired compound can be used as the suitable amino-protecting group P in the compound of formula (III'). The specific example of protecting groups which can be used for this purpose includes formyl, acetyl, trifluoroacetyl, benzoyl, para-toluenesulfonyl, methoxycarbonyl, ethoxycarbonyl, t-butoxycarbonyl, benzyloxycarbonyl, para-methoxybenzyloxycarbonyl, trichloroethoxycarbonyl, beta-iodoethoxycarbonyl, benzyl, para-methoxybenzyl, trityl, tetrahydropyranyl, etc.

After the reaction is completed, the amino-protecting group present in the resulting compound of formula (I') can be removed by hydrolysis, solvolysis or reduction depending on properties of the relevant protecting group. For example, the compound of formula (I') is treated in a solvent in the presence or absence of an acid or base at the temperature of 0° to 130° C. to remove the protecting group. As the acid which can be used for this purpose, an inorganic acid such as hydrochloric acid, hydrobromic acid, sulfuric acid, phosphoric acid, etc., an organic acid such as acetic acid, trifluoroacetic acid, formic acid, toluenesulfonic acid, etc., or a Lewis acid such as boron tribromide, aluminum chloride, etc., can be mentioned. As the base for this purpose, hydroxide of an alkali or alkaline earth metal such as sodium hydroxide, barium hydroxide, etc., an alkali metal carbonate such as sodium carbonate, calcium carbonate, etc., an alkali metal alkoxide such as sodium methoxide, sodium ethoxide, etc., or sodium acetate, and the like can be used. The reaction can be carried out in the presence of a solvent, for example, water or an organic solvent such as ethanol, tetrahydrofuran, dioxane, ethyleneglycol, acetic acid, etc., or a mixture of such organic solvent and water. If required, this reaction can also be practiced in the absence of any solvent.

In addition, when the protecting group is para-toluenesulfonyl, benzyl, trityl, para-methoxybenzyl, benzyloxycarbonyl, para-methoxybenzyloxycarbonyl, trichloroethoxycarbonyl, betaiodoethoxycarbonyl and the like, such groups can be effectively removed by means of a reduction. Although the reaction condition of the reduction for removing protecting group may be varied with properties of the relevant protecting group, the reduction can be generally carried out with hydrogen gas stream in an inert solvent in the presence of a catalyst such as platinum, palladium, Raney nickel, etc., at the temperature of 10° to 100° C. or with metal sodium or metal lithium in ammonia at the temperature of –50° to –10° C.

The compound of formula (II) used as the starting material in the present invention is a known compound and can be readily prepared according to a method known in the prior publication (see, J. M. Domagala, et al., J. Med. Chem. 34, 1142 (1991); J. M. Domagala, et al., J. Med. Chem. 31, 991 (1988); D. Bouzard, et al., J. Med. Chem. 35, 518 (1992)).

The compound of formula (III) used as another starting material in the present invention can be readily prepared according to the method as depicted in the following reaction schemes 3, 4 and 5.

Reaction Scheme 3

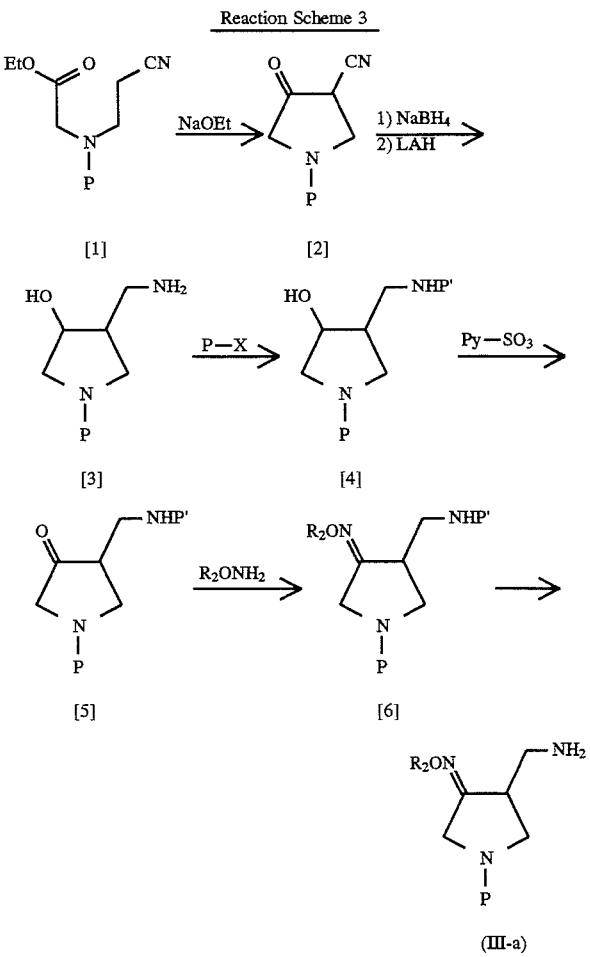

Reaction Scheme 4

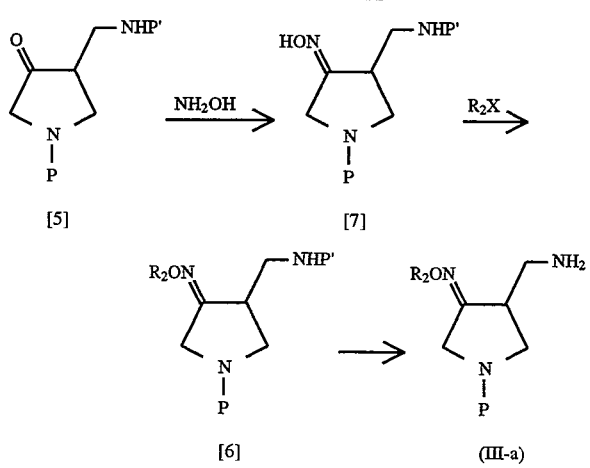

In the above reaction schemes 3 and 4,
the protecting groups P and P' independently of one another represent the same amino-protecting group as defined for P in connection with the compound of formula (III) and can be identical with or different from each other; and Py represents pyridine.

The process depicted in the reaction schemes 3 and 4 will be specifically explained hereinafter.

According to the reaction scheme 3, first a cyano ester [1] having a protected amino group can be reacted with sodium ethoxide in a solvent such as ethanol to obtain a 3-keto-4-cyanopyrrolidine [2]. The resulting cyanopyrrolidine [2] is reduced with hydrogen gas in the presence of a platinum catalyst to prepare an aminoalcohol [3]. In this case, the cyanopyrrolidine [2] may be reduced by means of other reductant to prepare the aminoalcohol [3]. For example, the ketone and cyano groups can be reduced with lithium aluminumhydride(LAH), sodium borohydride-cobalt chloride complex(NaBH$_4$—CoCl$_3$) or lithium borohydride (LiBH$_4$). Alternatively, the aminoalcohol [3] can be synthesized by reducing first the ketone group to a hydroxyl group by means of sodium borohydride(NaBH$_4$) and then reducing the cyano group by lithium aluminum hydride(LAH). Then, the amino group of the aminoalcohol [3] thus prepared is selectively protected to obtain a protected amine [4], which is then treated with sulfur trioxide(SO$_3$)-pyridine mixture in dimethylsulfoxide solvent (see, Parikh, J. R. and Doering, W. v. E. J. Am. Chem. Soc. 1967, 89, 5505), or oxidized with other oxidant, to prepare a ketone compound [5]. The resulting ketone compound [5] is then reacted with a O-substituted hydroxyamine of formula R$_2$ONH$_2$ to obtain the desired substituted oxime compound [6], which can be deprotected by means of a suitable method selected depending on the kind of protecting group to obtain the desired oxime compound (III) wherein R$_3$ and R$_4$ are hydrogen, i.e. the compound of formula (III-a).

Alternatively, according to the method depicted in the reaction scheme 4, the ketone compound [5] is reacted with hydroxyamine to obtain the desired oxime compound [7] and the compound [7] is reacted with a suitable electrophilic compound of formula R$_2$X which can introduce the desired R$_2$ group, in the presence of a base to prepare the oxime derivative of formula [6], which is then deprotected by means of a suitable method selected depending on the kind of protecting group in the same manner as in the reaction scheme 3 to prepare the desired oxime compound (III-a).

The compound of formula (III) wherein R$_3$ and R$_4$ of aminomethyl group present on 4-position of pyrrolidine are other than hydrogen, i.e. the compound of formula (III-b), can be prepared by the following reaction scheme 5.

Reaction Scheme 5

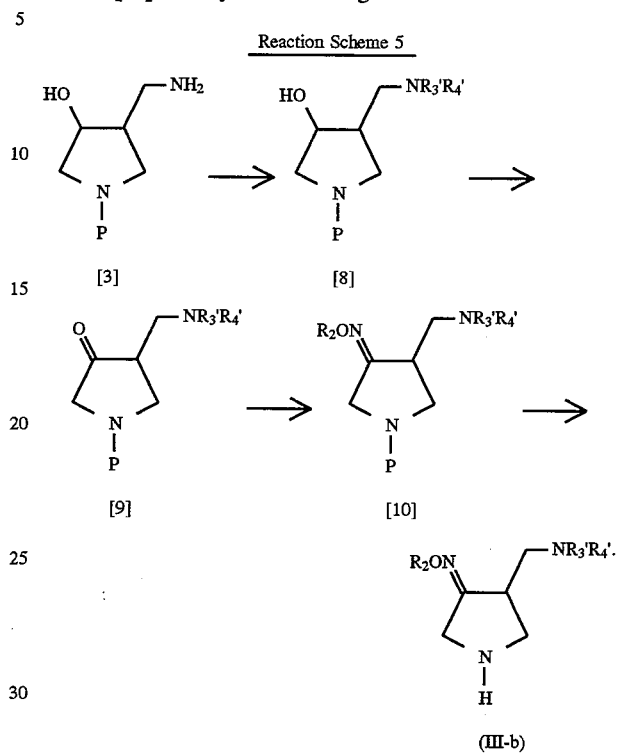

In the above reaction scheme,
R$_3$' and R$_4$' represent the same meaning as defined for R$_3$ and R$_4$ in connection with the compound of formula (I), provided that they cannot be hydrogen.

According to the method of reaction scheme 5, first the amine compound [3] is treated with C$_1$–C$_3$ aldehyde and then reduced to obtain a substituted amine compound [8] and the resulting amine compound [8] is treated with sulfur trioxide(SO$_3$)-pyridine mixture in dimethylsulfoxide solvent, or oxidized with other oxidant, to obtain a ketone compound [9]. The resulting ketone compound [9] can be treated in the same manner as in the method for treating ketone compound [5] in the reaction schemes 3 and 4 to synthesize the desired compound of formula (III-b).

The synthetic methods as described above will be more specifically explained in the following preparation examples.

The present invention also provides an antibacterial composition comprising the novel compound of formula (I), as defined above, or a pharmaceutically acceptable salt thereof as an active component together with a pharmaceutically acceptable carrier. When such antibacterial composition is used for clinical purpose, it may be formulated into solid, semi-solid or liquid pharmaceutical preparations for oral, parenteral or topical administration by combining the compound of formula (I) with a pharmaceutically acceptable inert carrier. The pharmaceutically acceptable inert carrier which can be used for this purpose may be solid or liquid. The solid or semi-solid pharmaceutical preparation in the form of powders, tablets, dispersible powders, capsules, cachets, suppositories and ointments may be prepared in which case solid carriers are usually used. The solid carrier which can be used is preferably one or more substances selected from the group consisting of diluents, flavouring agents, solubilizing agents, lubricants, suspending agents, binders, swelling agents, etc. or may be encapsulating substances. In the case of powder preparation, the micronized active component is contained in an amount of 5 or 10 to 70% in the carrier. Specific example of the suitable solid carrier includes magnesium carbonate, magnesium stearate, talc, sugar, lactose, pectine, dextrin, starch, gelatin, tragaganth, methylcellulose, sodium carboxymethylcellulose, low boiling wax, cocoa butter, etc. Because of their ease in administration, tablets, powders, cachets and capsules represent the most advantageous solid preparation for oral administration.

The liquid preparation includes solutions, suspensions and emulsions. For example, the injectable preparation for parenteral administration may be in the form of water or water-propyleneglycol solution, of which isotonicity, pH and the like can be adjusted to be suited for the physiological condition of living body. The liquid preparation can also be prepared in the form of a solution in aqueous polyethyleneglycol solution. The aqueous solution for oral administration can be prepared by dissolving the active component in water and adding a suitable coloring agent, flavouring agent, stabilizer and thickening agent thereto. The aqueous suspension suitable for oral administration can be prepared by dispersing the micronized active component in viscous substances such as natural or synthetic gum, methylcellulose, sodium carboxymethylcellulose and other known suspending agent.

It is especially advantageous to formulate the aforementioned pharmaceutical preparations in dosage unit form for ease of administration and uniformity of dosage. Dosage unit forms of the preparation refer to physically discrete units suitable as unitary dosage, each unit containing a predetermined quantity of the active component calculated to produce the desired therapeutic effect. Such dosage unit form can be in the packaged form, for example, a tablet, a capsule or a powder filled in vial or ampule, or an ointment, gel or cream filled in tube or bottle.

Although the amount of the active component contained in the dosage unit form can be varied, it can be generally adjusted within the range of 1 to 100 mg depending on the efficacy of the selected active component.

When the active compound of formula (I) of the present invention is used as a medicine for treatment of bacterial infections, it is preferably administered in an amount of about 6 to 14 mg per kg of body weight at the first stage. However, the administration dosage can be varied with the requirement of the subject patient, severity of the infections to be treated, the selected compound and the like.

The preferred dosage suitable for a certain condition can be determined by a person skilled in this art according to a conventional manner. In general, the therapeutic treatment is started from the amount less than the optimal dosage of the active compound and then the administration dosage is increased little by little until the optimal therapeutic effect is obtained. As a matter of convenience, the total daily dosage can be divided into several portions and administered over several times.

As mentioned above, the compound of the present invention shows a potent and broad spectrum antibacterial activity against various pathogenic organisms including gram-positive and gram-negative strains. The antibacterial activity of the present compound against gram-negative strains is comparable to or higher than that of the known antibacterial agents (for example, ciprofloxacin), and particularly, the antibacterial activity of the present compound against gram-positive strains is far superior to that of the known antibacterial agents. In addition, the present compound also exhibits a very potent antibacterial activity against the strains resistant to the known quinolone compounds.

In view of the pharmacokinetic properties, the compound of the present invention has a high water-solubility and thus can be well absorbed in the living body, in comparison with the known quinolone compounds, to show a very high bioavailability. The biological half life of the present compound is far longer than that of the known quinolone compounds, and therefore, the present compound can be administered once a day to be suitably used as an antibacterial agent.

Moreover, since the compound according to the present invention is less toxic, it can be effectively used for prophylaxis and treatment of diseases caused by bacterial infections in warm-blooded animals including human being.

The present invention will be more specifically explained in the following examples. However, it should be understood that the following preparations and examples are intended to illustrate the present invention and not to limit the scope of the present invention in any manner.

Preparation 1

Synthesis of (2-cyano-ethylamino)acetic acid ethyl ester

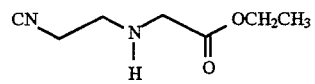

139.6g (1 mole) of glycine ethyl ester hydrochloride was dissolved in 80 ml of distilled water and to this solution was added 230 ml of an aqueous solution of 67.3 g (1.2 mole eq.) of potassium hydroxide. Then, 106.2 g (2 mole eq.) of acrylonitrile was added to the reaction solution while heating and stirring at 50° to 60° C. The reaction mixture was stirred for 5 hours with heating and then the organic layer was separated. The aqueous layer was extracted with ethyl ether and the extract was combined with the organic layer as separated above. The combined organic layer was dried over anhydrous magnesium sulfate and filtered. The filtrate was concentrated under reduced pressure to remove the solvent. The residue was distilled under reduced pressure (100° to 150° C./10.25 torr) to obtain 65.6 g (Yield: 48%) of the title compound.

$^1$H NMR (CDCl$_3$, ppm): δ4.20(2H, q), 3.48(2H, s), 2.96 (2H, t), 2.54(2H, t), 1.30(3H, t)

MS (FAB, m/e): 157(M+H)

Preparation 2

Synthesis of 4-cyano-1-(N-t-butoxycarbonyl)-pyrrolidin-3-one

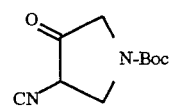

In the above formula and the following, Boc represents t-butoxycarbonyl. 29 g (0.186 mole) of the compound prepared in Preparation 1 was dissolved in 200 ml of chloroform and the resulting solution was introduced into a 1 L flask. Then, 45 g (1.1 mole eq.) of di-t-butoxycarbonyldicarbonate was added thereto and the reaction mixture was stirred for 17 hours at room temperature. The reaction solution was concentrated and the residue was diluted with 250 ml of absolute ethanol. The resulting solution was added to sodium ethoxide (NaOEt) solution prepared by adding 6 g of metal sodium (Na) turnings to 220 ml of absolute ethanol, under refluxing and heating. The reaction was continuously conducted for further one hour under refluxing with heating. The reaction solution was concentrated under reduced pressure and the residue was diluted with water and then washed with methylene chloride. The aqueous layer was adjusted with 1N HCl to pH 4 and extracted with ethyl acetate. The extract was dried over anhydrous magnesium sulfate and then filtered. The filtrate was concentrated to obtain a stoichiometric amount of the title compound in a crude state.

$^1$H NMR (COCl$_3$, ppm): δ4.5–3.5(5H, m), 1.5(9H, s)

MS (FAB, m/e): 211(M+H)

Preparation 3

Synthesis of 4-aminomethyl-1-(N-t-butoxycarbonyl) pyrrolidin-3-ol hydrochloride

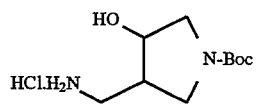

3 g (14 mmole) of the compound prepared in Preparation 2 was dissolved in the mixture of 357 ml of absolute ethanol and 7 ml of chloroform and the resulting solution was introduced into a flask. Then, a catalytic amount of platinum oxide(PtO$_2$) was added thereto. After air was removed from the reaction flask under reduced pressure, the reaction mixture was stirred for 17 hours at room temperature with blowing up the hydrogen gas from a balloon filled with hydrogen gas. The reaction solution was filtered and the filtrate was concentrated to obtain a stoichiometric amount of the title compound.

$^1$H NMR (CDCl$_3$, ppm): δ8.0(2H, bs), 3.5–2.0(7H, m), 3.3(2H, s), 1.38(9H, s)

MS (FAB, m/e): 217(M+H)

Preparation 4

Synthesis of 4-(N-t-butoxycarbonyl)aminomethyl-1-(N-t-butoxycarbonyl)pyrrolidin-3-ol

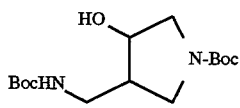

Method A:

20 g (0.094 mole) of the compound prepared in Preparation 3 was dissolved in the mixture of 456 ml of dioxane and 268 ml of distilled water and the resulting solution was adjusted with 1N aqueous sodium hydroxide solution to pH 9. Then, 30.9 g (1.5 mole eq.) of di-t-butoxycarbonyldicarbonate was added thereto, and the reaction mixture was stirred for 30 minutes at room temperature and concentrated under reduced pressure. The residue was diluted with methylene chloride. After adding water to the reaction solution, the organic layer was separated and the aqueous layer was acidified to pH 4 and then extracted with methylene chloride. The extract was combined with the organic layer as separated above and the combined solution was dried over anhydrous magnesium sulfate and concentrated. The residue was purified with column chromatography to obtain 17 g (Yield: 57%) of the title compound.

$^1$H NMR (CDCl$_3$, ppm): δ4.95(1H, m), 4.1(1H, m), 3.5(2H, m), 3.3–3.0(4H, m), 2.1(1H, in), 1.45(18H, s)

MS (FAB, m/e): 317(M+H)

Method B:

10 g (0.047 mole) of the compound prepared in Preparation 2 was introduced into a 1 L flask and then dissolved by adding 500 ml of dry tetrahydrofuran. This solution was cooled to −3° C. under ice-sodium chloride bath and then 3.8 g (0.094 mole) of lithium aluminumhydride(LAH) was added portionwise thereto over 20 minutes. After the addition is completed, the reaction mixture was stirred for one hour under ice-water bath. When the reaction is completed, 4 ml of water, 4 ml of 15% aqueous sodium hydroxide solution and 12 ml of water were carefully and successively added to the reaction mixture. The whole mixture was vigorously stirred for 3 hours at room temperature and 10 g of anhydrous magnesium sulfate was added thereto. This mixture was stirred and then filtered, and the filtrate was concentrated to stoichiometrically obtain the product. The resulting product was diluted with 200 ml of dioxane-water (2:1 by volume) and 12.3 g (0.056 mole) of di-t-butoxycarbonyldicarbonate was added thereto at room temperature. The reaction solution was stirred for one hour at room temperature to complete the reaction and then concentrated. The residue was diluted again with ethyl acetate, washed with saturated aqueous sodium chloride solution, dried over anhydrous magnesium sulfate and filtered. The filtrate was concentrated and the residue was then purified with column chromatography using hexane-ethyl acetate (2:1 by volume) eluant to obtain 8.2 g (Yield: 55%) of the title compound.

Method C:

210 g (1 mole) of the compound prepared in Preparation 2 was dissolved in 4 L of methanol and this solution was introduced into a 6 L reaction vessel equipped with a thermometer. The internal temperature of the reaction vessel was cooled to 10° C. under dry ice-acetone bath. 76 g (2 mole) of sodium borohydride (NaBH$_4$) was added portionwise thereto over 1.5 hours while maintaining the internal temperature of the vessel at 10° to 13° C. After the addition is completed, the reaction mixture was stirred for further 30 minutes at the same temperature so that all the ketone can be reduced to alcohol. Then, 243 g (1 mole) of cobalt chloride hydrate was added thereto over 10 minutes. When the reaction is completed, the resulting solid complex was dissolved in 4 L of ammonia water and this solution was diluted with 8 L of water and then extracted with ethyl acetate. The organic layer was washed with saturated saline, dried over anhydrous magnesium sulfate and filtered. The filtrate was concentrated and mixed with the mixture of 1.5 L of dioxane and 0.5 L of distilled water. 212 g of di-t-butoxycarbonyldicarbonate was added thereto and the whole mixture was stirred for 2 hours at room temperature. After the reaction is completed, the reaction mixture was concentrated under reduced pressure, diluted again with dichloromethane, washed with water, dried over anhydrous magnesium sulfate and then filtered. The filtrate was concentrated and then purified with silica gel column chromatography (eluant: hexane-ethyl acetate 2:1 by volume) to obtain 202 g (Yield: 64%) of the title compound.

Method D:

10 g (0.047 mole) of the compound prepared in Preparation 2 was introduced into a 1 L flask and dissolved by adding 500 ml of methanol. This solution was cooled down under ice bath and 3.6 g (0.094 mole) of sodium borohydride was added portionwise thereto over 20 minutes. The reaction mixture was stirred for further 30 minutes to complete the reaction, and then concentrated under reduced pressure, diluted with ethyl acetate, washed with water, dried over anhydrous magnesium sulfate and then filtered. The filtrate was concentrated to obtain the compound in which the desired ketone group is reduced to an alcohol. 10.1 g (0.047 mole) of the resulting alcohol compound was dissolved in 200 ml of dry tetrahydrofuran and this solution was cooled down to −5° C. under ice-salt bath. 2.6 g (0.066 mole) of lithium aluminumhydride was added thereto over 20 minutes. The reaction mixture was stirred for further 30 minutes at the same temperature to complete the reaction, and then 2.6 ml of water, 2.6 ml of 15% sodium hydroxide and 7.8 ml of water were added in order thereto. This mixture was stirred for one hour at room temperature. After adding 6 g of anhydrous magnesium sulfate, the mixture was stirred for further 30 minutes and filtered. The filtrate was concentrated to obtain the product. The resulting product was diluted with 200 ml of dioxane-water (2:1 by volume) and 12.3 g (0.056 mole) of di-t-butoxycarbonyldicarbonate was added portionwise thereto. The mixture was stirred for 30 minutes to complete the reaction, and then concentrated, diluted with ethyl acetate, washed with saturated saline, dried over anhydrous magnesium sulfate and then filtered. The filtrate was concentrated and the residue was purified with column chromatography to obtain 12.3 g (Yield: 83%) of the title compound.

Preparation 5

Synthesis of 4-(N-t-butoxycarbonyl)aminomethyl-1-(N-t-butoxycarbonyl)pyrrolidin-3-one

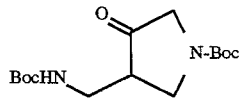

14 g (0.044 mole) of the compound prepared in Preparation 4 was dissolved in 64 ml of dimethylsulfoxide and 18.5 ml (3 mole eq.) of triethylamine was added thereto. This mixture was cooled down under ice bath. When the wall of reaction flask begins to freeze, 12.7 g (1.8 mole eq.) of pyridine-sulfur trioxide(Py—SO₃) oxidant was added portionwise thereto. After the addition is completed, the ice bath was removed and the reaction solution was stirred for 3 hours at room temperature, diluted with water and then extracted with ethyl acetate. The extract was dried over anhydrous magnesium sulfate and concentrated to stoichiometrically obtain the title compound in a crude state.

$^1$H NMR (CDCl₃, ppm): δ4.95(1H, bs), 4.15–2.7(6H, m), 2.8 (1H, br), 1.45(9H, s), 1.40(9H, s)

MS (FAB, m/e): 315 (M+H)

Preparation 6

Synthesis of 1-(N-t-butoxycarbonyl)-4-(N-t-butoxycarbonyl)aminomethyl-pyrrolidin-3-one oxime

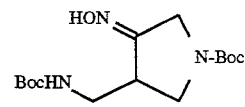

300 mg of the compound prepared in Preparation 5 was dissolved in the mixture of 6 ml of 95% ethanol and 3 ml of tetrahydrofuran(THF) and this solution was introduced into a 30 ml reaction vessel. 232 mg (3.5 mole eq.) of hydroxyamine hydrochloride (NH₂OH.HCl) was added thereto and then 281 mg (3.5 mole eq.) of sodium hydrogen carbonate dissolved in 1.5 ml of distilled water was added. The reaction mixture was stirred for 40 minutes at 40° C. under oil bath to complete the reaction, cooled down and then concentrated under reduced pressure. The residue was diluted with methylene chloride, washed with saturated aqueous sodium chloride solution, dried over anhydrous magnesium sulfate and then filtered. The filtrate was concentrated and the residue was subjected to silica gel column chromatography eluting with hexane-ethyl acetate (1:1 by volume) to obtain 230 mg (Yield: 73%) of the title compound.

$^1$H NMR (CDCl₃, ppm): δ9.70(1H, bs), 5.05(1, bs), 4.2(2H, br), 3.83(1H, m), 3.5–3.2(3H,m), 3.0(1H, m), 1.42 (18H, s)

MS (FAB, m/e: 330(M+H)

Preparation 7

Synthesis of 1-(N-t-butoxycarbonyl)-4-(N-t-butoxycarbonyl)aminomethyl-pyrrolidin-3-one-benzyloxime

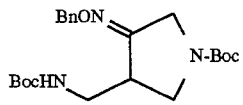

659 mg of the compound prepared in Preparation 6, 193 mg of tetra-n-butylammonium bromide and 855 mg of benzyl bromide were added to 15 ml of dichloromethane and then 5 ml of 15% aqueous sodium hydroxide solution was added thereto. The reaction mixture was stirred for 30 minutes at room temperature. The organic layer was separated, dried over anhydrous magnesium sulfate and filtered. The filtrate was distilled under reduced pressure and the residue was purified with glass column chromatography to obtain 776 mg (Yield: 92%) of the title compound.

$^1$H NMR (CDCl₃, ppm): δ7.38(5H, m), 5.13(2H, s), 4.92 (1H, m), 4.13(2H, m), 3.76(1H, m), 3.41 (1H, m), 3.25(2H, m), 3.02(1H, m), 1.50(9H, s), 1.49(9H, s)

MS (FAB, m/e): 420(M+H)

Preparations 8 to 17

The amine compounds listed in the following Table 1 were prepared according to the same procedure as Preparation 7 except that the corresponding benzylbromide derivatives having R₂ structure as presented in the following Table 1 are used instead of benzylbromide.

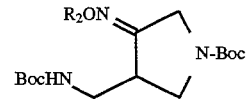

TABLE 1

Preparations 8 to 17

| Prep. | R₂ | NMR (CDCl₃), δ (ppm) | FAB MS (M+H) |
|---|---|---|---|
| 8 | 4-nitrobenzyl | 8.2(2H, m), 7.4(2H, m), 5.2(2H, s), 4.9(1H, s), 4.2(2H, m), 3.8(1H, m), 3.5–3.2(3H, m), 3.0(1H, m), 1.5(18H, s) | 465 |
| 9 | 4-methoxybenzyl | 7.3(2H, m), 6.9(2H, m), 5.0(2H, s), 4.9(1H, s), 4.1(2H, m), 3.8(3H, s), 3.75(1H, m), 3.5–3.0(4H, m), 1.45(18H, s) | 450 |
| 10 | 4-fluorobenzyl | 7.3(2H, m), 7.0(2H, m), 5.0(2H, s), 4.8(1H, br), 4.2(2H, m), 3.9(1H, m), 3.4(3H, m), 3.0(1H, m), 1.46(18H, s) | 438 |
| 11 | 4-t-butylbenzyl | 7.4–7.3(4H, m), 5.1(2H, s), 5.0(1H, s), 4.1(2H, m), 3.8(1H, m), 3.6–3.0(4H, m), 1.45(18H, s), 1.3(9H, s) | 476 |
| 12 | 2-cyanobenzyl | 7.8–7.3(4H, m), 5.3(2H, s), 5.0(1H, bs), 4.2(2H, s), 3.9(1H, m), 3.6–3.2(3H, m), 3.0(1H, s), 1.5(18H, s) | 445 |
| 13 | pyridylmethyl | 8.6(2H, m), 7.7(1H, m), 7.3(1H, m), 5.1(2H, s), 4.9(1H, s), 4.1(2H, m), 3.8(1H, m), 3.6–3.2(3H, m), 3.0(1H, m), 1.5(18H, s) | 421 |
| 14 | (furylmethyl group) | 7.4(2H, m), 6.5(1H, m), 4.9(2H, s), 4.9(1H, s), 4.1(2H, m), 3.8(2H, m), 3.2(3H, m), 1.5(18H, s) | 410 |
| 15 | (fluorobenzothiazolylmethyl group) | 7.7(2H, m), 7.2(1H, m), 5.5(1H, s), 5.0(1H, s), 4.2(2H, m), 3.8(1H, m), 3.6–3.1(4H, m), 1.5(18H, s) | 495 |
| 16 | (benzo[1,3]dioxol-5-ylmethyl group) | 6.9(3H, m), 6.0(2H, m), 5.0(3H, m), 4.1(2H, m), 3.8(1H, m), 3.6–3.2(3H, m), 3.0(1H, m), 1.5(18H, s) | 464 |
| 17 | (1-(3,4-dihydroxyphenyl)ethyl-COOH group) | 7.3–7.0(3H, m), 6.8(1H, s), 5.1(1H, s), 4.2(2H, m), 3.8(1H, m), 3.5–3.0(4H, m), 1.6–1.4(27H, s) | 496 |

Preparation 18

Synthesis of 4-aminomethyl-pyrrolidin-3-one-benzyloxime dihydrochloride 20 ml of methanol was cooled down to 5° C. and then 10 ml of acetyl chloride was slowly added thereto. This mixture was stirred for 30 minutes and 990 mg of the compound prepared in Preparation 7, which is dissolved in 10 ml of methanol, was added thereto. The reaction mixture was stirred for 50 minutes at room temperature and concentrated under reduced pressure. The residue was washed with ethyl acetate and dried to obtain 648 mg (Yield: 94%) of the title compound as a yellow solid.

¹H NMR (DMSO-d₆, ppm): δ10.0(1H, m), 8.35(2H, m), 7.40(5H, m), 5.18(2H, s), 4.00(2H, m), 3.69(1H, m), 3.40 (2H, m), 3.12(2H, s)

MS (FAB, m/e): 220(M+H)

Preparations 19 to 28

The compounds listed in the following Table 2 were prepared from the amine compounds prepared in Preparations 8 to 17 according to the same procedure as Preparation 18.

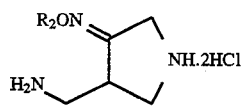

TABLE 2

Preparations 19 to 28

| Prep. | R₂ | NMR (CDCl₃), δ (ppm) | FAB MS (M+H) |
|---|---|---|---|
| 19 | 4-nitrobenzyl | 10.3–10.1(2H, s), 8.3(3H, s), 8.2(2H, d), 7.7(2H, d), 5.3(2H, s), 4.1(2H, m), 3.7(1H, m), 3.4(2H, m), 3.1(2H, m) | 265 |
| 20 | 4-methoxybenzyl | 10.2–10.0(2H, s), 8.4(3H, s), 7.3(2H, d), 6.9(2H, d), 5.0(2H, s), 3.9(2H, m), 3.73(3H, s), 3.7(1H, m), 3.4(2H, m), 3.1(2H, m) | 250 |
| 21 | 4-fluorobenzyl | 10.2(2H, s), 8.4(3H, s), 7.3(2H, m), 7.2(2H, m), 5.1(2H, s), 3.9(2H, m), 3.7(1H, m), 3.4(2H, m), 3.1(2H, m) | 238 |
| 22 | 4-t-butylbenzyl | 10.2(2H, s), 8.4(3H, s), 7.4–7.3(4H, m), 5.1(2H, s), 3.9(2H, m), 3.7(1H, m), 3.2(2H, m), 3.1(2H, m), 1.3(9H, s) | 276 |
| 23 | 2-cyanobenzyl | 10.2–10.0(2H, s), 8.2(3H, s), 7.9–7.5(4H, m), 5.3(2H, s), 4.0(2H, m), 3.7(1H, m), 3.2(2H, m), 3.1(2H, m) | 245 |
| 24 | 3-pyridylmethyl | 10.3(1H, s), 10.1(1H, s), 8.9(1H, s), 8.8 (1H, m), 8.5(1H, d), 8.4(3H, m), 8.0(1H, m), 5.4(2H, s), 4.0(2H, m), 3.7(1H, m), 3.4 (2H, m), 3.1(2H, m) | 221 |
| 25 | 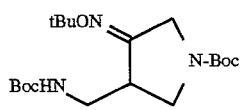 | 10.3(2H, s), 8.4(3H, s), 7.6(1H, s), 6.4(1H, s), 5.0(2H, s), 4.0(2H, m), 3.8(1H, m), 3.4(2H, m), 3.1(2H, m) | 210 |
| 26 | 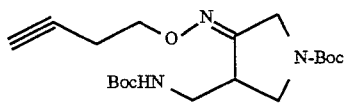 | 10.3(2H, s), 8.3(3H, s), 8.1(1H, m), 7.9 (1H, m), 7.4(1H, m), 5.5(2H, s), 4.1(2H, m), 3.9(1H, m), 3.14(2H, m), 3.1(2H, m) | 295 |
| 27 | (3,4-methylenedioxybenzyl structure) | 10.2(2H, s), 8.3(3H, s), 7.0(3H, m), 6.3 (2H, s), 5.3(2H, m), 4.1(2H, m), 3.9(1H, m), 3.4–3.2(2H, m), 3.1(2H, m) | 264 |
| 28 | (3,4-dihydroxyphenyl with COOH) | 10.3–10.2(2H, s), 8.4(3H, s), 8.0–7.3(3H, m), 7.0(1H, s), 4.2(2H, m), 3.8(1H, m), 3.5–3.2(3H, m), 3.0(1H, m) | 296 |

Preparation 29

Synthesis of 1-(N-t-butoxycarbonyl)-4-(N-t-butoxycarbonyl)aminomethyl-pyrrolidin-3-one t-butyloxime 300 mg of the compound prepared in Preparation 5 was dissolved in the mixture of 6 ml of 95% ethanol and 3 ml of tetrahydrofuran(THF) and this solution was introduced into a 30 ml reaction vessel. 487 mg (3.5 mole eq.) of o-t-butylhydroxyamine hydrochloride was added thereto and then 281 mg (3.5 mole eq.) of sodium hydrogen carbonate dissolved in 1.5 ml of distilled water was added. The reaction mixture was stirred for 40 minutes at 40° C. under oil bath to complete the reaction, and then cooled down, concentrated under reduced pressure, diluted with methylene chloride, washed with saturated aqueous sodium chloride solution, dried over anhydrous magnesium sulfate and then filtered. The filtrate was concentrated and the residue was subjected to silica gel column chromatography eluting with hexane-ethyl acetate (1:1 by volume) to obtain 285 mg (Yield: 80%) of the title compound.

¹H NMR (CDCl₃, ppm): δ5.10(1H, bs), 4.05(2H, s), 3.71(1H, dd), 3.43 (1H, br), 3.2 (2H, m), 3.0(1H, m), 1.42(18H, s), 1.30(9H, s)

MS (FAB, m/e): 386(M+H)

Preparation 30

Synthesis of 1-(N-t-butoxycarbonyl)-4-(N-t-butoxycarbonyl)aminomethyl-pyrrolidin-3-one 3-butynyloxime A. Synthesis of 3-butynyl hydroxylamine 0.35 g (5 mmole) of 3-butynol, 0.86 g (5.25 mmole) of N-hydroxyphthalimide and 1.44 g (5.5 mmole) of triphenylphosphine were dissolved in 15 ml of dry tetrahydrofuran, and then 1.05 g (6 mmole) of diethylazodicarboxylate was added thereto over 30 minutes. The mixture was stirred for 10 minutes at room temperature and then distilled under reduced pressure to remove the solvent. To the residue was added 50 ml of ethyl acetate-hexane (1:1 v/v). The precipitated solid material was filtered off and the filtrate was concentrated. The residue was purified with column chromatography (hexane-ethyl acetate 9:1 v/v). The resulting white solid [0.54 g, Yield 50%, $^1$H NMR (CDCl$_3$, ppm): δ7.85(2H, m), 7.75(2H, m), 4.2(2H, t), 2.8(2H, dd), 2.5(2H, dd), 2.1(1H, s), FAB MS(POS): [M+H]$^+$=216] was dissolved in 12 ml of methylene chloride, and 0.25 g (5 mmole) of hydrazine hydrate diluted with 4 ml of methanol was added dropwise thereto. The solid precipitate was filtered off and the filtrate was concentrated at low temperature under reduced pressure to obtain 0.2 g (Yield: 93%) of the title compound.

$^1$H NMR (CDCl$_3$, ppm): δ9.5(2H, br), 4.5(2H, t), 2.8(2H, m), 2.4 (2H, m), 2.05(1H, s)

MS (FAB, m/e): 86(M+H)$^+$

B. Synthesis of the title compound 0.45 g (1.43 mmole) of the compound prepared in Preparation 5 and 0.2 g (2.35 mmole) of 3-butynyl hydroxyamine were dissolved in 5 ml of methanol and the reaction was conducted for 12 hours at 60° C. The reaction solution was concentrated under reduced pressure and the residue was subjected to column chromatography (ethyl acetate-hexane 1:4 v/v) to obtain 0.59 g (stoichiometric amount) of the title compound.

$^1$H NMR (CDCl$_3$, ppm): δ5.0(1H, m), 4.15(2H, t), 4.0 (2H, s), 3.75(1H, m), 3.6–3.2(3H, m), 3.0(1H, m), 2.5(2H, m), 2.0(1H, s), 1.45(18H, s)

FAB MS (POS): 382(M+H)$^+$

Preparations 31 to 36

The amine compounds listed in the following Table 3 were prepared according to the same procedure as Preparation 30 except that the corresponding alcohol derivatives having R$_2$ structure as represented in the following Table 3 are used instead of 3-butynol.

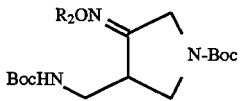

TABLE 3

| Prep. | R$_2$ | $^1$H NMR (CDCl$_3$), δ (ppm) | FAB MS (M+H) |
|---|---|---|---|
| 31 | isopropyl | 5.0(1H, br), 4.1(2H, s), 4.0(1H, m), 3.4(1H, m), 3.55–3.25(3H, m), 3.0(1H, m), 1.55(18H, s), 1.0(6H, d) | 372 |
| 32 | cyclobutyl | 4.7(1H, m), 4.2(2H, s), 3.8(1H, m), 3.4(1H, m), 3.3(2H, m), 3.0 (1H, m), 2.3(2H, m), 2.1(2H, m), 1.8(1H, m), 1.6(1H, m), 1.5 (18H, s) | 384 |
| 33 | cyclopentyl | 4.7(1H, m), 4.1(2H, m), 3.7(1H, m),3.4(1H, m), 3.3(2H, m), 3.0 (1H, m), 1.8(4H, m), 1.7(4H, m), 1.6(18H, s) | 398 |
| 34 | (tetrahydrofuranyl) | 5.0–4.8(1H, m), 4.3–3.7(6H, m), 3.3(2H, m), 3.0(1H, m), 2.1(2H, m), 1.5(18H, s), 1.3(2H, m) | 400 |
| 35 | cyclopropyl-methyl | 5.1(1H, br), 4.1(2H, m), 3.9(2H, m), 3.8(1H,m), 3.5(1H, m), 3.3 | 384 |

TABLE 3-continued

| Prep. | R$_2$ | $^1$H NMR (CDCl$_3$), δ (ppm) | FAB MS (M+H) |
|---|---|---|---|
| | | (2H, m), 3.0(1H, m), 1.5(18H, s), 1.1(1H, m), 0.6(2H, s), 0.3 (2H, s) | |
| 36 | isobutyl | 5.05(1H, br), 4.15(2H, s), 4.1 (2H, d), 3.6(2H, m), 3.3(1H, m), 3.0(2H, m), 2.5(1H, m), 1.5 (18H, s), 1.05(6H, d) | 386 |

Preparation 37

Synthesis of 1-(N-t-butoxycarbonyl)-4-(N-t-butoxycarbonyl)aminomethyl-pyrrolidin-3-one propargyl oxime

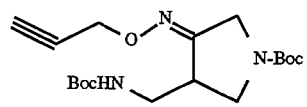

659 mg of the compound prepared in Preparation 6, 193 mg of tetra-n-butylammonium bromide and 855 mg of propargyl bromide were added to 15 ml of dichloromethane, and 5 ml of 15% aqueous sodium hydroxide solution was added thereto. This mixture was stirred for 30 minutes at room temperature. The organic layer was separated, dried over anhydrous magnesium sulfate and then filtered. The filtrate was distilled under reduced pressure and the residue was purified with glass column chromatography to obtain 776 mg (Yield: 92%) of the title compound.

$^1$H NMR (CDCl$_3$, ppm): δ4.92(1H, m), 4.13(2H, m), 3.76(1H, m), 3.41(1H, m), 3.25(2H, m), 3.02 (1H, m), 1.50(9H, s), 1.49(9H, s)

MS (FAB, m/e): 368(M+H)

Preparations 38 and 39

The amine compounds listed in the following Table 4 were prepared according to the same procedure as Preparation 37 except that the corresponding alkyl derivatives having R$_2$ structure as represented in the following Table 4 are used instead of propargyl.

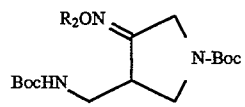

TABLE 4

| Prep. | R$_2$ | $^1$H NMR (CDCl$_3$), δ (ppm) | FAB MS (M+H) |
|---|---|---|---|
| 38 | methoxy-methyl | 5.15–4.9(3H), 4.15(2H, m), 3.75(1H, m), 3.5–3.2(5H), 3.0(1H, m), 1.5 (18H, s) | 374 |
| 39 | 2-chloro-ethyl | 4.9(1H, m), 4.3(2H, t), 4.1(2H, s), 3.7(3H, m), 3.6(1H, m), 3.5–3.0(3H, m), 1.45(18H, s) | 392 |

Preparation 40

Synthesis of 4-aminomethyl-pyrrolidin-3-one t-butyloxime dihydrochloride

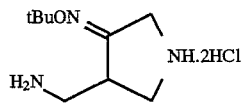

5 ml of methanol was cooled down to 0° C. and 3 ml of acetyl chloride was slowly added thereto. This mixture was stirred for 10 minutes and 640 mg of the compound prepared in Preparation 29, which is dissolved in 10 ml of methanol, was added thereto. The reaction mixture was stirred for 20 minutes at room temperature and concentrated under reduced pressure. The residue was filtered, washed with ethylether and dried to obtain 390 mg (Yield: 91%) of the title compound as a white solid.

$^1$H NMR (DMSO-$d_6$, ppm): δ10.0–9.6(2H, bsX2), 8.20 (3H, br), 3.90(2H,dd), 3.61(1H, bs), 3.40(2H, bs), 3.12(2H, bs), 1.25(9H, s)

MS (FAB, m/e): 186(M+H)

Preparations 41 to 50

The compounds of Preparations 41 to 50 as listed in the following Table 5 were prepared from the compounds prepared in Preparations 30 to 40 according to the same procedure as Preparation 40.

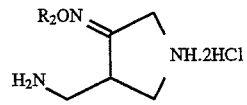

TABLE 5

| | Preparations 41 to 50 | | |
|---|---|---|---|
| Prep. | $R_2$ | $^1$H NMR (CDCl$_3$), δ (ppm) | FAB MS (M+H) |
| 41 | CH$_2$CH$_2$C≡CH | 10.1–9.8(2H, br), 8.2(3H, br), 4.3(2H, t), 4.0(2H, s), 3.7(1H, m), 3.6–3.2(3H, m), 3.0(1H, m), 2.8(1H, s), 2.6 (2H, t) | 182 |
| 42 | isopropyl | 10.1–9.8(2H, br), 8.3(3H, br), 4.4(1H, m), 3.9(2H, d), 3.7(1H, m), 3.3(2H, s), 3.1 (2H, m), 1.2(6H, d) | 172 |
| 43 | cyclobutyl | 10.2–9.8(2H, br), 8.2(3H, br), 4.8(1H, m), 4.3(2H, s), 3.7(1H, m), 3.6–3.2(3H, m), 3.0(1H, m), 1.8(2H, m), 1.7 (2H, m), 1.5(1H, m), 1.45 (1H, m) | 184 |
| 44 | cyclopentyl | 10.2–9.8(2H, br), 8.2(3H, br), 4.7(1H, m), 4.3(2H, s), 3.8(1H, m), 3.3(1H, m), 3.2 (3H, m), 1.8(4H, m), 1.6 (2H, m), 1.5(2H, m) | 198 |
| 45 | (tetrahydrofuranyl) | 10.1–9.8(2H, br), 8.3(3H, s), 4.1–3.6(10H, m), 3.2(2H, s), 2.2–1.9(2H, m) | 200 |
| 46 | cyclopropyl-methyl | 10.1–9.8(2H, br), 8.3(3H, s), 4.0–3.8(4H, m), 3.65 | 184 |

TABLE 5-continued

| | Preparations 41 to 50 | | |
|---|---|---|---|
| Prep. | $R_2$ | $^1$H NMR (CDCl$_3$), δ (ppm) | FAB MS (M+H) |
| | | (1H, m), 3.4(2H, m), 3.1 (2H, m), 1.1(1H, m), 0.5 (2H, d), 0.2(2H, d) | |
| 47 | isobutyl | 10.3–9.9(2H, br), 8.4(3H, br), 3.9–3.8(4H, m), 3.65 (1H, m), 3.3(2H, s), 3.1 (2H, m), 1.9(1H, m), 0.85 (6H, d) | 186 |
| 48 | propargyl | 10.0(1H, m), 8.3(2H, m), 4.8(2H, s), 4.0(2H, m), 3.7 (1H, m), 3.6(1H, s) 3.4(2H, m), 3.1(2H, s) | 168 |
| 49 | methoxymethyl | 10–9.6(2H, br), 8.2(3H, br), 5.1(2H, dd) 4.1–3.8(2H, m), 3.7(1H, m), 3.3–3.0(4H, m) | 174 |
| 50 | 2-chloroethyl | 10–9.7(2H, br), 8.2(3H, br), 4.3(2H, t), 4.0(2H, m), 3.8 (2H, t), 3.7(1H, m), 3.4(2H, m), 3.2(1H, m), 3.1(2H, m) | 192 |

Preparation 51

Synthesis of 4-(N-t-butoxycarbonyl)aminomethyl-1-(N-t-butoxycarbonyl)pyrrolidin-3-one O-methyloxime

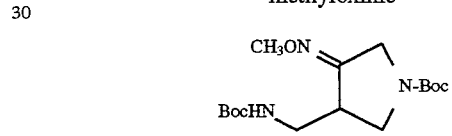

260 mg (8.28×10$^{-4}$ mole) of the compound prepared in Preparation 5 was dissolved in the mixture of 5 ml of 95% ethanol and 2.5 ml of tetrahydrofuran and this solution was introduced into a reaction vessel. Then, 256 mg (3.7 mole eq.) of methoxyamine hydrochloride was added thereto and 257 mg (3.7 mole eq.) of sodium hydrogen carbonate (NaHCO$_3$) dissolved in 2.5 ml of distilled water was also added. The reaction mixture was stirred for 1 hours at 40° C. under oil bath, concentrated under reduced pressure, washed successively with aqueous ammonium chloride solution and aqueous sodium chloride solution, dried over anhydrous magnesium sulfate and then filtered. The filtrate was concentrated to obtain 250 mg (Yield: 88%) of the title compound.

$^1$H NMR (CDCl$_3$, ppm): δ4.98(1H, bs), 3.81(3H, s), 3.75–2.80(7H, m), 1.40(18H, s)

MS (FAB, m/e): 344(M+H)

Preparations 52 and 53

The compounds listed in the following Table 6 were prepared according to the same procedure as Preparation 51 except that phenoxyamine hydrochloride or ethoxyamine hydrochloride are used instead of methoxyamine hydrochloride.

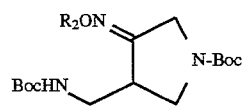

TABLE 6

Preparations 52 and 53

| Prep. | $R_2$ | $^1$H NMR (CDCl$_3$), δ (ppm) | FAB MS (M+H) |
|---|---|---|---|
| 52 | phenyl | 7.3(5H, m), 4.97(1H, bs), 3.8–2.8 (7H, m), 1.40(18H, s) | 406 |
| 53 | —CH$_2$CH$_3$ | 5.0(1H, bs), 3.8–2.8(7H, m), 1.42 (18H, s), 1.41(18H, s), 1.38(3H, t) | 358 |

Preparation 54

Synthesis of 4-aminomethyl-pyrrolidin-3-one O-methyloxime ditrifluoroacetate

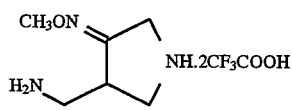

5 ml of trifluoroacetic acid was added to 250 mg of the compound prepared in Preparation 51, and this mixture was stirred for 20 minutes at room temperature. The reaction mixture was concentrated under reduced pressure, dissolved in the smallest amount of acetonitrile and then solidified with ethylether to obtain 220 mg (Yield: 84%) of the title compound in a purified state.

$^1$H NMR (CD$_3$OD, ppm): δ4.1(2H, s), 3.96(3H, s), 3.83 (1H, dd), 3.7–3.2 (6H, m)

MS (FAB, m/e): 144(M+H)

Preparations 55 to 57

The corresponding compounds of Preparations 55 to 57 were prepared from the compounds prepared in Preparations 6, 52 and 53, respectively, according to the same procedure as Preparation 54.

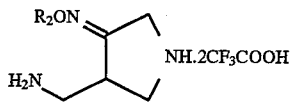

TABLE 7

Preparations 55 to 57

| Prep. | $R_2$ | $^1$H NMR (CDCl$_3$), δ (ppm) | FAB MS (M+H) |
|---|---|---|---|
| 55 | —H | 4.1–3.2(7H, m) | 130 |
| 56 | —Ph | 7.2–7.4(5H, m), 4.1–3.2(7H, m) | 206 |
| 57 | —CH$_2$CH$_3$ | 4.2–3.1(9H, m), 1.3(3H, t) | 158 |

EXAMPLE 1

Synthesis of 7-(4-aminomethyl-3-benzyloxyimino-pyrrolidin-1-yl)-1-cyclopropyl-6-fluoro-1,4-dihydro-4-oxo-1,8-naphthyridine-3-carboxylic acid

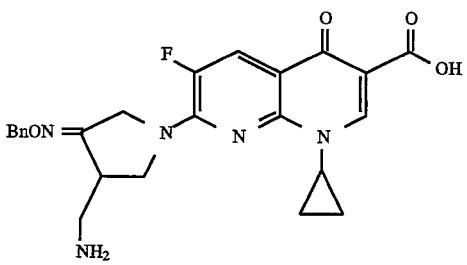

622 mg of 7-chloro-1-cyclopropyl-6-fluoro-1,4-dihydro-4-oxo-1,8-naphthyridine-3-carboxylic acid and 643 mg of the compound prepared in Preparation 18 were suspended in 15 ml of acetonitrile. This suspension was cooled down under ice-water bath and then 1.0 ml of 1,8-diazabicyclo [5.4.0]undec-7-ene(DBU) was slowly added thereto. The reaction mixture was stirred for 1.5 hours at room temperature and, after adding 15 ml of water, was then concentrated. The concentrated suspension was filtered. The filtered solid product was washed with water and ethanol to obtain 584 mg (Yield: 57%) of the title compound.

$^1$H NMR (DMSO-d$_6$, ppm): δ8.59(1H, s), 8.03(1H, d), 7.40(5H, m), 5.14(2H, s), 4.75(2H, s), 4.18 (1H, m), 3.94 (1H, m), 3.83(1H, m), 3.35(2H, m), 3.05(1H, m), 2.81(1H, m), 2.73 (1H, m), 1.25–1.05 (4H, m)

MS (FAB, m/e): 466(M+H)

EXAMPLE 2 to 11

The same starting material as Example 1 was reacted with each of the compounds prepared in Preparations 19 to 28 according to the same procedure as Example 1 to prepare the respective compounds listed in the following Table 8.

TABLE 8

Examples 2 to 11

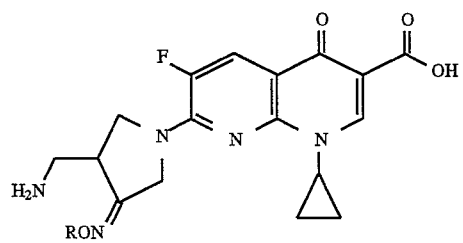

| Examp. No. | R | ¹H NMR, δ (ppm) | NMR solv. | FAB, MS (M+1) | Reac. time (min) | Yield (%) |
|---|---|---|---|---|---|---|
| 2 | (4-methoxybenzyl) | 8.73(1H, s), 8.05(1H, d), 7.30 (2H, d), 6.98(2H, d), 5.10(2H, s), 4.61(2H, s), 4.25(1H, m), 3.90(1H, m), 3.80(3H, s), 3.70 (1H, m), 3.00(3H, m), 1.26(2H, m), 1.07(2H, m) | CDCl₃ | 496 | 10 | 75 |
| 3 | (4-tert-butylbenzyl) | 8.75(1H, s), 8.05(1H, d), 7.45 (2H, d), 7.30(2H, d), 5.15(2H, s), 4.62(2H, s), 4.25(1H, m), 3.85(1H, m), 3.75(1H, m), 3.10 (1H, m), 2.98(2H, m), 1.35(9H, s), 1.25(2H, m), 1.09(2H, m) | CDCl₃ | 522 | 15 | 76 |
| 4 | (4-fluorobenzyl) | 8.68(1H, s), 8.00(1H, d), 7.35 (2H, m), 7.10(2H, m), 5.08(2H, s), 4.59(2H, s), 4.20(1H, m), 3.95(1H, m), 3.81(1H, m), 3.00 (3H, m), 1.23(2H, m), 1.04(2H, m) | CDCl₃ | 484 | 14 | 80 |
| 5 | (4-nitrobenzyl) | 8.59(1H, s), 8.21(2H, d), 8.06 (1H, s), 7.64(2H, d), 5.29(2H, s), 4.68(2H, s), 4.20(1H, m), 3.95(1H, m), 3.85(1H, m), 3.10 (1H, m), 2.80(2H, m), 1.18(2H, m), 1.10(2H, m) | DMSO | 511 | 10 | 76 |
| 6 | (2-cyanobenzyl) | 8.58(1H, s), 8.05(1H, d), 7.92– 7.42(4H, m), 5,28(2H, s), 4.65(2H, s), 4.20(1H, m), 3.95 (1H, m), 3.78(1H, m), 3.10(1H, m), 2.80(2H, m), 1.20(2H, m), 1.09(2H, m) | DMSO | 491 | 20 | 82 |
| 7 | (3,4-methylenedioxybenzyl) | 8.74(1H, s), 8.10(1H, d), 6.92 (3H, m), 6.10(2H, s), 5.10(2H, s), 4.75(2H, s), 4.30(1H, m), 3.95(1H, m), 3.85(1H, m), 3.15 (1H, m), 3.10(2H, m), 1.28(2H, m), 1.09(2H, m) | CDCl₃ | 510 | 25 | 79 |
| 8 | (3-pyridylmethyl) | 8.60(1H, d), 8.57(1H, s), 8.52 (1H, d), 8.03(1H, d), 7.80(1H, d), 7.41(1H, q), 5.18(2H, s), 4.65(2H, s), 4.17(1H, m), 3.94 (1H, m), 3.75(1H, m), 3.30(2H, m), 3.04(1H, m), 2.81(1H, m), 2.73(1H, m), 1.30–1.00(4H, m) | DMSO-d₆ | 467 | 90 | 70 |

TABLE 8-continued

Examples 2 to 11

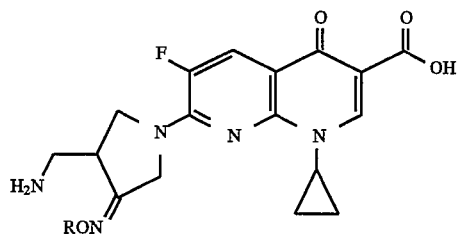

| Examp. No. | R | ¹H NMR, δ (ppm) | NMR solv. | FAB, MS (M+1) | Reac. time (min) | Yield (%) |
|---|---|---|---|---|---|---|
| 9 | (furfuryl group) | 8.82(1H, s), 8.05(1H, d), 7.51 (1H, d), 7.45(1H, m), 6.5(1H, s), 5.02(2H, m), 4.5(2H, m), 4.20(1H, m), 3.95(1H, m), 3.70 (1H, m), 3.00(1H, m), 2.80(1H, m), 2.70(1H, m), 1.00(4H, m) | DMSO | 456 | 15 | 69 |
| 10 | (3,4-dihydroxyphenyl-COOH-ethyl group) | 8.58(1H, s), 8.00(1H, d), 7.10 (3H, m), 6.72(1H, s), 4.80(2H, s), 4.20(1H, m), 3.95(1H, m), 3.85(1H, m), 3.10(1H, m), 2.95 (2H, m), 1.07(4H, m) | DMSO | 542 | 20 | 65 |
| 11 | (4-fluorobenzothiazolylmethyl group) | 8.76(1H, s), 8.20(1H, m), 8.02 (1H, d), 7.89(1H, m), 7.40(1H, m), 5.60(2H, s), 4.78(2H, m), 4.45(1H, m), 3.85(1H, m), 3.70 (1H, m), 3.10(2H, m), 1.30(2H, m), 1.15(2H. m) | DMSO | 541 | 25 | 73 |

EXAMPLE 12

Synthesis of 7-(4-aminomethyl-3-benzyloxyimino-pyrrolidin-1-yl)-1-cyclopropyl-6-fluoro-1,4-dihydro-4-oxoquinoline-3-carboxylic acid

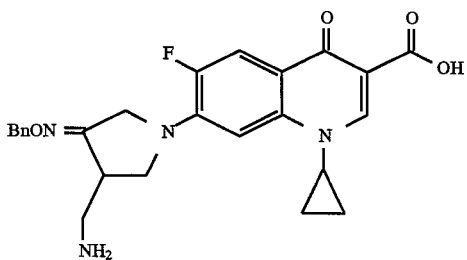

530 mg of 1-cyclopropyl-6,7-difluoro-1,4-dihydro4-oxoquinoline-3-carboxylic acid and 584 mg of the compound prepared in preparation 8 were suspended in 15 ml of acetonitrile. This suspension was cooled down under ice-water bath and then 913 mg of 1,8-diazabicyclo[5.4.0] undec-7-ene(DBU) was slowly added thereto. The reaction mixture was stirred for 2 hours at 80° C. and, after adding 15 ml of water, was then concentrated. The concentrated suspension was filtered. The filtered solid product was washed with water and ethanol to obtain 631 mg (yield: 68%) of the title compound.

¹H NMR (DMSO-$d_6$, ppm): δ8.60(1H, s), 7.92(1H, d), 7.38(5H, m), 5.10(2H, s), 4.87(2H, s), 4.10(1H, m), 3.94 (1H, m), 3.86(1H, m), 3.37(2H, m), 3.02(1H, m), 2.38(1H, m), 2.73(1H, m), 1.25–1.05(4H, m)

MS (FAB, m/e): 465(M+H)

EXAMPLES 13 to 22

The same starting material as Example 12 was reacted with each of the compounds prepared in Preparations 19 to 28 according to the same procedure as Example 12 to prepare the respective compounds listed in the following Table 9.

TABLE 9

Examples 13 to 22

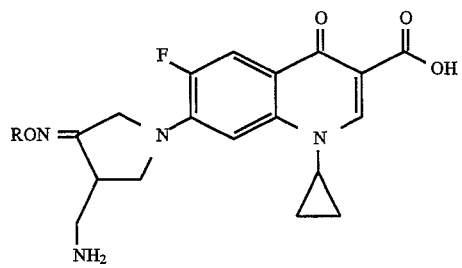

| Examp. No. | R | ¹H NMR, δ (ppm) | NMR solv. | FAB, MS (M+1) | Reac. time (min) | Yield (%) |
|---|---|---|---|---|---|---|
| 13 | 4-methoxybenzyl | 8.6(1H, s), 7.8(1H, d), 7.2(3H, d), 6.9(2H, d), 5.1(2H, s), 4.4 (2H, s), 3.9(1H, m), 3.8(1H, ,m), 3.7(3H, s), 3.65(1H, m), 3.0 (1H, m), 2.9–2.7(2H, m), 1.3–1.1(4H, m) | DMSO-$d_6$ | 495 | 2 | 60 |
| 14 | 4-tert-butylbenzyl | 8.6(1H, s), 7.8(1H, d), 7.4(2H, d), 7.3(3H, m), 5.1(2H, s), 4.4 (2H, s), 3.9(1H, m), 3.8(1H, m), 3.7(1H, m), 3.0(1H, m), 2.9–2.7 (2H, m), 1.4(9H, s), 1.3–1.1 (4H, m) | DMSO-$d_6$ | 521 | 2 | 65 |
| 15 | 4-fluorobenzyl | 8.6(1H, s), 7.8(1H, d), 7.4(2H, m), 7.2(3H, m), 5.1(2H, s), 4.4 (2H, s), 3.9(1H, m), 3.8(1H, m), 3.7(1H, m), 3.0(1H, m), 2.9–2.7 (2H, m), 1.3–1.1(4H, m) | DMSO-$d_6$ | 483 | 4 | 67 |
| 16 | 4-nitrobenzyl | 8.6(1H, s), 8.2(2H, d), 7.8(1H, d), 7.6(2H, d), 7.2(1H, d), 5.3 (2H, s), 4.4(2H, s), 3.9(1H, m), 3.8(1H, m), 3.7(1H, m), 3.0(1H, m), 2.9–2.7(2H, m), 1.3–1.1 (4H, m) | DMSO-$d_6$ | 510 | 3 | 58 |
| 17 | 2-cyanobenzyl | 8.6(1H, s), 7.9–7.4(5H, m), 7.2 (1H, d), 5.3(2H, s), 4.4(2H, s), 3.9(1H, m), 3.8(1H, m), 3.7(1H, m), 3.0(1H, m), 2.9–2.7(2H, m), 1.3–1.1(4H, m) | DMSO-$d_6$ | 490 | 4 | 55 |
| 18 | 3,4-methylenedioxybenzyl | 8.6(1H, s), 7.8(1H, d), 7.2(1H, d), 6.9(3H, m), 6.1(2H, s), 5.1 (2H, s), 4.4(2H, s), 3.9(1H, m), 3.8(1H, m), 3.7(1H, m), 3.0(1H, m), 2.9–2.7(2H, m), 1.3–1.1 (4H, m) | DMSO-$d_6$ | 509 | 4 | 71 |
| 19 | 3-pyridylmethyl | 8.6(3H, m), 7.8(2H, m), 7.4(1H, q), 7.2(1H, d), 5.2(2H, s), 4.4 (1H, m), 3.9(1H, m), 3.8(1H, m), 3.7(1H, m), 3.0(1H, m), 2.9–2.7 (2H, m), 1.3–1.1(4H, m) | DMSO-$d_6$ | 466 | 4 | 53 |

TABLE 9-continued

Examples 13 to 22

[Structure: quinolone core with F, COOH, cyclopropyl, and pyrrolidinyl substituent bearing =NOR and CH2NH2 groups]

| Examp. No. | R | $^1$H NMR, δ (ppm) | NMR solv. | FAB, MS (M+1) | Reac. time (min) | Yield (%) |
|---|---|---|---|---|---|---|
| 20 | [furfuryl group] | 8.6(1H, s), 7.8(1H, d), 7.5(2H, m), 7.2(1H, d), 6.5(1H, m), 5.0 (2H, m), 4.4(1H, m), 3.9(1H, m), 3.8(1H, m), 3.7(1H, m), 3.0(1H, m), 2.9–2.7(2H, m), 1.3–1.1 (4H, m) | DMSO-$d_6$ | 455 | 4 | 60 |
| 21 | [1-(3,4-dihydroxyphenyl)ethyl with COOH] | 8.6(1H, s), 7.8(1H, d), 7.2(1H, d), 7.1(3H, m), 6.7(1H, s), 4.4 (1H, m), 3.9(1H, m), 3.8(1H, m), 3.7(1H, m), 3.0(1H, m), 2.9–2.7 (2H, m), 1.3–1.1(4H, m) | DMSO-$d_6$ | 541 | 4 | 50 |
| 22 | [2-(6-fluorobenzothiazol-2-yl)ethyl] | 8.6(1H, s), 8.2(1H, m), 7.9–7.8 (2H, m), 7.4(1H, m), 7.2(1H, d), 5.6(2H, s), 4.4(1H, m), 3.9(1H, m), 3.8(1H, m), 3.0(1H, m), 2.9–2.7(2H, m), 1.3–1.1(4H, m) | DMSO-$d_6$ | 540 | 4 | 70 |

EXAMPLE 23

Synthesis of 7-(4-aminomethyl-3-benzyloxyimino-pyrrolidin-1-yl)-1-cyclopropyl-6,8-difluoro-1,4-dihydro-4-oxo-quinoline-3-carboxylic acid

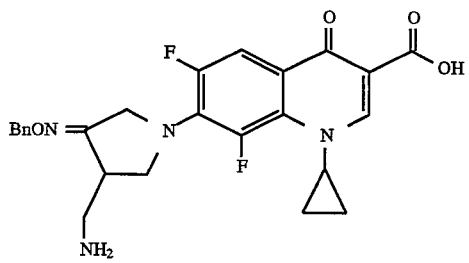

566 mg of 1-cyclopropyl-6,7,8-trifluoro-1,4-dihydro-4-oxo-quinoline-3-carboxylic acid and 584 mg of the compound prepared in Preparation 8 were suspended in 15 ml of acetonitrile. This suspension was cooled down under ice-water bath and then 913 mg of 1,8-diazabicyclo[5.4.0] undec-7-ene(DBU) was slowly added thereto. The reaction mixture was stirred for 2 hours at 80° C. and, after adding 10 ml of water, was then concentrated. The concentrated suspension was filtered. The filtered solid product was washed with water and ethanol to obtain 704 mg (Yield: 73%) of the title compound.

$^1$H NNR (DMSO-$d_6$, ppm): δ8.64(1H, s), 7.99(1H, d), 7.41(5H, m), 5.10(2H, s), 4.73(2H, s), 4.18(1H, m), 3.92 (1H, m), 3.86(1H, m), 3.37(2H, m), 3.02(1H, m), 2.83(1H, m), 2.73(1H, m), 1.25–1.05 (4H, m)

MS (FAB, m/e): 483(M+H)

EXAMPLES 24 to 33

The same starting material as Example 23 was reacted with each of the compounds prepared in Preparations 19 to 28 according to the same procedure as Example 23 to prepare the respective compounds listed in the following Table 10.

TABLE 10

Examples 24 to 33

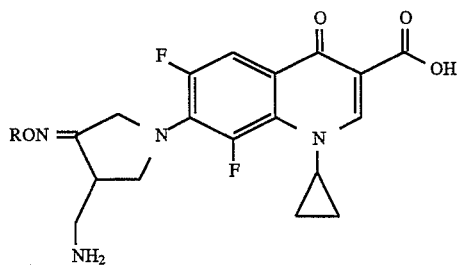

| Examp. No. | R | ¹H NMR, δ (ppm) | NMR solv. | FAB, MS (M+1) | Reac. time (min) | Yield (%) |
|---|---|---|---|---|---|---|
| 24 | (4-methoxybenzyl) | 8.6(1H, s), 7.7(1H, d), 7.2(2H, d), m 6.9(2H, d), 5.1(2H, s), 4.3 (2H, s), 4.1(1H, m), 3.9(1H, m), 3.8(1H, m), 3.7(3H, s), 2.9(1H, m), 2.8–2.7(2H, m), 1.15(4H, m) | DMSO-$d_6$ | 513 | 2 | 75 |
| 25 | (4-tert-butylbenzyl) | 8.6(1H, s), 7.7(1H, d), 7.5(2H, m), 7.1(2H, m), 5.1(2H, s), 4.3 (2H,s), 4.1(1H, m), 3.9(1H, m), 3.8(1H, m), 2.9(1H, m), 2.8–2.7 (2H, m), 1.4(9H, s), 1.15(4H, m) | DMSO-$d_6$ | 539 | 4 | 70 |
| 26 | (4-fluorobenzyl) | 8.6(1H, s), 7.7(1H, d), 7.3(2H, m), 7.1(2H, m), 5.1(2H, s), 4.3 (2H,s), 4.1(1H, m), 3.9(1H, m), 3.8(1H, m), 2.9(1H, m), 2.8–2.7 (2H, m), 1.15(4H, m) | DMSO-$d_6$ | 501 | 4 | 80 |
| 27 | (4-nitrobenzyl) | 8.6(1H, s), 8.2(2H, d), 7.7(1H, d), 7.6(2H, d), 5.3(2H, s), 4.3 (2H, s), 4.1(1H, m), 3.9(1H, m), 3.8(1H, m), 2.9(1H, m), 2.8–2.7 (2H, m), 1.15(4H, m) | DMSO-$d_6$ | 528 | 3 | 68 |
| 28 | (2-cyanobenzyl) | 8.6(1H, s), 7.9–7.4(5H, m), 5.3 (2H, s), 4.3(2H, s), 4.1(1H, m), 3.9(1H, m), 3.8(1H, m), 2.9(1H, m), 2.8–2.7(2H, m), 1.15(4H, m) | DMSO-$d_6$ | 508 | 2 | 70 |
| 29 | (3,4-methylenedioxybenzyl) | 8.6(1H, s), 7.7(1H, d), 7.0(3H, m), 6.1(2H, s), 5.1(2H, s), 4.3 (2H, s), 4.1(1H, m), 3.9(1H, m), 3.8(1H, m), 2.9(1H, m), 2.8–2.7 (2H, m), 1.15(4H, m) | DMSO-$d_6$ | 527 | 3 | 69 |
| 30 | (pyridylmethyl) | 8.6(3H, m), 7.8(1H, d), 7.7(1H, d), 7.4(1H, q), 5.3(2H, s), 4.3 (2H, s), 4.1(1H, m), 3.9(1H, m), 3.8(1H, m), 2.9(1H, m), 2.8–2.7 (2H, m), 1.15(4H, m) | DMSO-$d_6$ | 484 | 3 | 58 |

TABLE 10-continued

Examples 24 to 33

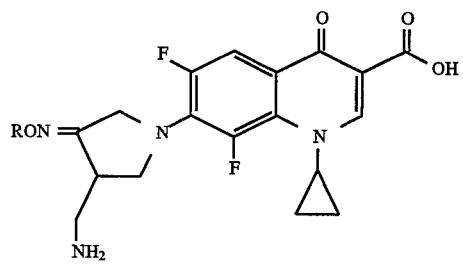

| Examp. No. | R | ¹H NMR, δ (ppm) | NMR solv. | FAB, MS (M+1) | Reac. time (min) | Yield (%) |
|---|---|---|---|---|---|---|
| 31 | (furanylmethyl) | 8.6(1H, s), 7.7(1H, d), 7.5(2H, m), 6.5(1H, m), 5.0(2H, m), 4.3 (2H, s), 4.1(1H, m), 3.9(1H, m), 3.8(1H, m), 2.9(1H, m), 2.8–2.7 (2H, m), 1.15(4H, m) | DMSO-$d_6$ | 473 | 3 | 70 |
| 32 | CH(COOH)–C₆H₃(OH)₂ | 8.6(1H, s), 7.7(1H, d), 7.1(3H, m), 6.6(1H, s), 4.3(2H, s), 4.1 (1H, m), 3.9(1H, m), 3.8(1H, m), 2.9(1H, m), 2.8–2.7(2H, m), 1.15(4H, m) | DMSO-$d_6$ | 559 | 4 | 59 |
| 33 | (fluorobenzothiazolyl-methyl) | 8.6(1H, s), 8.3(1H, m), 7.9(1H, m), 7.7(1H, d), 7.4(1H, m), 5.6 (2H, s), 4.3(2H, s), 4.1(1H, m), 3.9(1H, m), 3.8(1H, m), 2.9(1H, m), 2.8–2.7(2H, m), 1.15(4H, m) | DMSO-$d_6$ | 558 | 4 | 60 |

EXAMPLE 34

Synthesis of 7-(4-aminomethyl-3-benzyloxyimino-pyrrolidin-1-yl)-8-chloro-1-cyclopropyl-6-fluoro-1,4-dihydro-4-oxo-quinoline-3-carboxylic acid

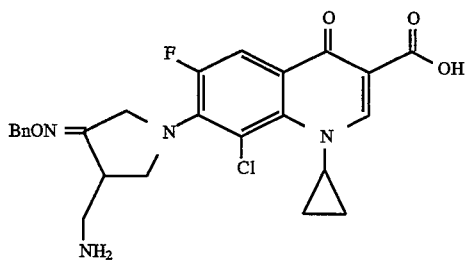

598 mg of 8-chloro-1-cyclopropyl-6,7-difluoro-1,4-dihydro-4-oxoquinoline-3-carboxylic acid and 584 mg of the compound prepared in Preparation 8 were suspended in 15 ml of acetonitrile and then mg of 1,8-diazabicyclo[5.4.0] undec-7-ene(DBU) was slowly added thereto. The reaction mixture was stirred for 3 hours at 80° C. and, after adding 15 ml of water, was then concentrated. The concentrated suspension was filtered. The filtered solid product was washed with water and ethyl ether to obtain 510 mg (Yield: 52%) of the title compound.

¹H NMR (DMSO-d6, ppm): δ8.78(1H, s), 7.91(1H, d), 7.41(5H, m), 5.16(2H, s), 4.74(2H, s), 4.16(1H, m), 3.90 (1H, m), 3.85(1H, m), 3.35(2H, m), 3.02(1H, m), 2.82(1H, m), 2.75(1H, m), 1.30–1.10(4H, m)

MS (FAB, m/e): 499(M+H)

EXAMPLES 35 to 44

The same starting material as Example 34 was reacted with each of the compounds prepared in Preparations 19 to 28 according to the same procedure as Example 34 to prepare the respective compounds listed in the following Table 11.

TABLE 11

Examples 35 to 44

| Examp. No. | R | ¹H NMR, δ (ppm) | NMR solv. | FAB, MS (M+1) | Reac. time (hr) | Yield (%) |
|---|---|---|---|---|---|---|
| 35 | 4-methoxybenzyl | 8.7(1H, s), 7.9(1H, d), 7.3(2H, d), 7.0(2H, d), 5.1(2H, s), 4.4 (2H, s), 4.3(1H, m), 3.8(1H, m), 3.7(3H, s), 3.0(1H, m), 2.9–2.6 (2H, s), 1.2–0.9(4H, m) | DMSO-$d_6$ | 529 | 3 | 63 |
| 36 | 4-tert-butylbenzyl | 8.7(1H, s), 7.9(1H, d), 7.5(2H, d), 7.3(2H, d), 5.2(2H, s), 4.4 (2H, s), 4.3(1H, m), 3.8(1H, m), 3.0(1H, m), 2.9–2.7(2H, m), 1.4 (9H, s), 1.2–0.9(4H, m) | DMSO-$d_6$ | 555 | 3 | 75 |
| 37 | 4-fluorobenzyl | 8.7(1H, s), 7.9(1H, d), 7.4(2H, m), 7.1(2H, m), 5.1(2H, s), 4.4 (2H, s), 4.3(1H, m), 3.8(1H, m), 3.0(1H, m), 2.9–2.7(2H, m), 1.2–0.9(4H, m) | DMSO-$d_6$ | 517 | 2 | 80 |
| 38 | 4-nitrobenzyl | 8.7(1H, s), 8.3(2H, d), 7.9(1H, d), 7.7(2H, d), 5.4(2H, s), 4.4 (2H, s), 4.3(1H, m), 3.8(1H, m), 3.0(1H, m), 2.9–2.7(2H, m), 1.2–0.9(4H, m) | DMSO-$d_6$ | 544 | 4 | 63 |
| 39 | 2-cyanobenzyl | 8.7(1H, s), 7.9–7.4(5H, m), 5.3 (2H, s), 4.4(2H, s), 4.3(1H, m), 3.8(1H, m) 3.0(1H, m), 2.9–2.7 (2H, m), 1.2–0.9(4H, m) | DMSO-$d_6$ | 524 | 4 | 70 |
| 40 | 3,4-methylenedioxybenzyl | 8.7 (1H, s), 7.9(1H, d), 7.0(3H, m), 6.1(2H, s), 5.1(2H, s), 4.4 (2H, s), 4.3(1H, m), 3.8(1H, m), 3.0(1H, m), 2.9–2.7(2H, m), 1.2–0.9(4H, m) | DMSO-$d_6$ | 543 | 2 | 67 |
| 41 | 3-pyridylmethyl | 8.7(1H, s), 7.9(1H, d), 8.6(2H, m), 7.8(1H, d), 7.4(1H, q), 5.2 (2H, s), 4.4(2H, s), 4.3(1H, m), 3.8(1H, m), 3.0(1H, m), 2.9–2.7 (2H, m), 1.2–0.9(4H, m) | DMSO-$d_6$ | 500 | 4 | 60 |

TABLE 11-continued

Examples 35 to 44

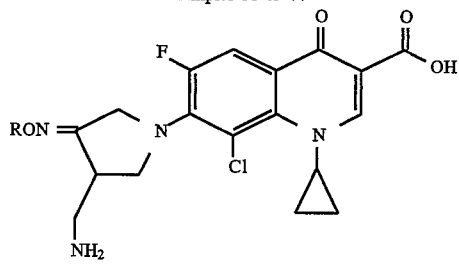

| Examp. No. | R | ¹H NMR, δ (ppm) | NMR solv. | FAB, MS (M+1) | Reac. time (hr) | Yield (%) |
|---|---|---|---|---|---|---|
| 42 | (furfuryl group) | 8.7(1H, s), 7.9(1H, d), 7.5(2H, m), 6.5(1H, m), 5.0(2H, m), 4.4 (2H, s), 4.3(1H, m), 3.8(1H, m), 3.0(1H, m), 2.9–2.7(2H, m), 1.2–0.9(4H, m) | DMSO-$d_6$ | 489 | 2 | 62 |
| 43 | (1-(3,4-dihydroxyphenyl)-1-carboxyethyl group) | 8.7(1H, s), 7.9(1H, d), 7.1(3H, m), 6.7(1H, s), 4.4(2H, s), 4.3 (1H, m), 3.8(1H, m), 3.0(1H, m), 2.9–2.6(2H, m), 1.2–0.9(4H, m) | DMSO-$d_6$ | 575 | 4 | 60 |
| 44 | (2-(4-fluorobenzothiazol-2-yl)ethyl group) | 8.7(1H, s), 8.2(1H, m), 7.9(2H, m), 7.4(1H, m), 5.6(2H, s), 4.4 (2H, s), 4.3(1H, m), 3.8(1H, m), 3.0(1H, m), 2.9–2.7(2H, m), 1.2–0.9(4H, m) | DMSO-$d_6$ | 574 | 4 | 76 |

EXAMPLE 45

Synthesis of 7-(4-aminomethyl-3-benzyloxyimino-pyrrolidin-1-yl)-1-cyclopropyl-6-fluoro-8-methoxy-1,4-dihydro-4-oxoquinoline-3-carboxylic acid

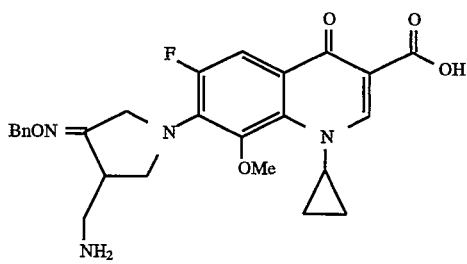

590 mg of 1-cyclopropyl-6,7-difluoro-8-methoxy-1,4-dihydro-4-oxoquinoline-3-carboxylic acid and 584 mg of the compound prepared in Preparation 8 were suspended in 15 ml of acetonitrile and then 913 mg of 1,8-diazabicyclo[5.4.0]undec-7-ene(DBU) was slowly added thereto. The reaction mixture was stirred for 2 hours at 80° C. and, after adding 15 ml of water, was then stirred for 30 minutes at room temperature and filtered. The filtered solid product was washed with water and ethyl ether to obtain 465 mg (Yield: 47%) of the title compound.

¹H NMR (DMSO-$d_6$, ppm): δ8.61(1H, s), 7.99(1H, d), 7.40(5H, m), 5.15(2H, s), 4.74(2H, s), 4.17(1H, m), 3.95 (1H, m), 3.83(1H, m), 3.60(3H, s), 3.35(2H, m), 3.02(1H, m), 2.80(1H, m), 2.71(1H, m), 1.30–1.10(4H, m)

MS (FAB, m/e): 495(M+H)

EXAMPLES 46 to 55

The same starting material as Example 45 was reacted with each of the compounds prepared in Preparations 19 to 28 according to the same procedure as Example 45 to prepare the respective compounds listed in the following Table 12.

TABLE 12

Examples 46 to 55

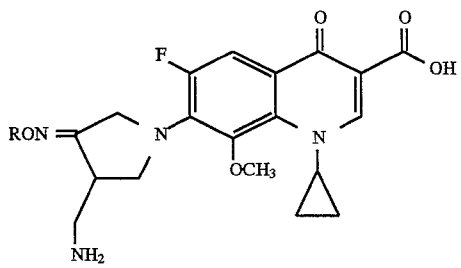

| Examp. No. | R | ¹H NMR, δ (ppm) | NMR solv. | FAB, MS (M+1) | Reac. time (hr) | Yield (%) |
|---|---|---|---|---|---|---|
| 46 | ―CH₂―C₆H₄―OCH₃ (p) | 8.8(1H, s), 7.8(1H, d), 7.4(2H, d), 7.1(2H, d), 5.2(2H, s), 4.6 (2H, s), 4.3(1H, m), 4.1(1H, m), 3.9(1H, m), 3.8(3H, s), 3.0(1H, m), 2.9–2.7(2H, m), 2.7(3H, s), 1.3(2H, m), 0.95(2H, m) | DMSO-$d_6$ | 525 | 17 | 38 |
| 47 | ―CH₂―C₆H₄―C(CH₃)₃ (p) | 8.8(1H, s), 7.8(1H, d), 7.6(2H, d), 7.4(2H, d), 5.3(2H, s), 4.6 (2H, s), 4.3(1H, m), 4.1(1H, m), 3.9(1H, m), 3.0(1H, m), 2.9–2.7 (2H, m), 2.7(3H, s), 1.5(9H, s), 1.3(2H, m), 0.95(2H, m) | DMSO-$d_6$ | 551 | 17 | 34 |
| 48 | ―CH₂―C₆H₄―F (p) | 8.8(1H, s), 7.8(1H, d), 7.5(2H, m), 7.2(2H, m), 5.2(2H, s), 4.6 (2H, s), 4.3(1H, m), 4.1(1H, m), 3.9(1H, m), 3.0(1H, m), 2.9–2.7 (2H, m), 2.7(3H, s), 1.3(2H, m), 0.95(2H, m) | DMSO-$d_6$ | 513 | 17 | 40 |
| 49 | ―CH₂―C₆H₄―NO₂ (p) | 8.8(1H, s), 8.3(2H, d), 7.8(1H, d), 7.7(2H, d), 5.4(2H, s), 4.6 (2H, s), 4.3(1H, m), 4.1(1H, m), 3.9(1H, m), 3.0(1H, m), 2.9–2.7 (2H, m), 2.7(3H, s), 1.3(2H, m), 0.95(2H, m) | DMSO-$d_6$ | 540 | 17 | 37 |
| 50 | ―CH₂―C₆H₄―CN (o) | 8.8(1H, s), 8.0–7.5(5H, m), 5.4 (2H, s), 4.6(2H, s), 4.3(1H, m), 4.1(1H, m), 3.9(1H, m), 3.0(1H, m), 2.9–2.7(2H, m), 2.7(3H, s), 1.3(2H, m), 0.95(2H, m) | DMSO-$d_6$ | 520 | 17 | 42 |
| 51 | ―CH₂―C₆H₃―OCH₂O― (3,4) | 8.8(1H, s), 7.8(1H, d), 7.0(3H, m), 6.2(2H, s), 5.2(2H, s), 4.6 (2H, s), 4.3(1H, m), 4.1(1H, m), 3.9(1H, m), 3.0(1H, m), 2.9–2.7 (2H, m), 2.7(3H, s), 1.3(2H, m), 0.95(2H, m) | DMSO-$d_6$ | 539 | 17 | 44 |
| 52 | ―CH₂―(4-pyridyl) | 8.8(1H, s), 8.6(2H, m), 7.9(1H, d), 7.8(1H, d), 7.4(1H, q), 5.3 (2H, s), 4.6(2H, s), 4.3(1H, m), 4.1(1H, m), 3.9(1H, m), 3.0(1H, m), 2.9–2.7(2H, m), 2.7(3H, s), 1.3(2H, m), 0.95(2H, m) | DMSO-$d_6$ | 496 | 17 | 30 |

TABLE 12-continued

Examples 46 to 55

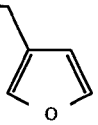

| Examp. No. | R | ¹H NMR, δ (ppm) | NMR solv. | FAB, MS (M+1) | Reac. time (hr) | Yield (%) |
|---|---|---|---|---|---|---|
| 53 | 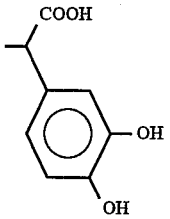 | 8.8(1H, s), 7.8(1H, d), 7.6(2H, m), 6.5(1H, m), 5.1(2H, m), 4.6 (2H, s), 4.3(1H, m), 4.1(1H, m), 3.9(1H, m), 3.0(1H, m), 2.9–2.7 (2H, m), 2.7(3H, s), 1.3(2H, m), 0.95(2H, m) | DMSO-$d_6$ | 485 | 17 | 29 |
| 54 | 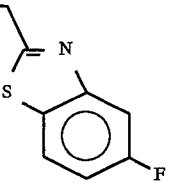 | 8.8(1H, s), 7.8(1H, d), 7.2(3H, m), 6.8(1H, s), 4.6(2H, s), 4.3 (1H, m), 4.1(1H, m), 3.9(1H, m), 3.0(1H, m), 2.9–2.7(2H, m), 2.7 (3H, s), 1.3(2H, m), 0.95(2H, m) | DMSO-$d_6$ | 571 | 20 | 27 |
| 55 | 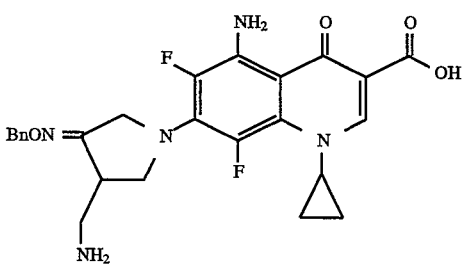 | 8.8(1H, s), 8.3(1H, m), 8.0(1H, m), 7.8(1H, d), 7.5(1H, m), 5.7 (2H, s), 4.6(2H, s), 4.3(1H, m), 4.1(1H, m), 3.9(1H, m), 3.0(1H, m), 2.9–2.7(2H, m), 2.7(3H, s), 1.3(2H, m), 0.95(2H, m) | DMSO-$d_6$ | 570 | 17 | 42 |

EXAMPLE 56

Synthesis of 5-amino-7-(4-aminomethyl-3-benzyloxyimino-pyrrolidin-1-yl)-1-cyclopropyl-6,8-difluoro-1,4-dihydro-4-oxoquinoline-3-carboxylic acid

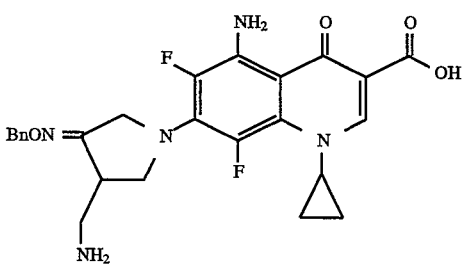

448 mg of 5-amino-1-cyclopropyl-6,7,8-trifluoro-1,4-dihydro-4-oxoquinoline-3-carboxylic acid and 438 mg of the compound prepared in Preparation 8 were suspended in 15 ml of acetonitrile and then 685 mg of 1,8-diazabicyclo [5.4.0]undec-7-ene(DBU) was slowly added thereto. The reaction mixture was heated for 6 hours at 80° C. and 10 ml of water was added thereto. This suspension was filtered. The filtered solid product was washed with water, acetonitrile and ethyl ether to obtain 395 mg (Yield: 53%) of the title compound.

¹H NMR (DMSO-$d_6$, ppm): δ8.62(1H, s), 7.92(1H, d), 7.40(5H, m), 6.10(2H, bs), 5.13(2H, s), 4.73(2H, s), 4.15 (1H, m), 3.95(1H, m), 3.82(1H, m), 3.35(2H, m), 3.01(1H, m), 2.80(1H, m), 2.73(1H, m), 1.25–1.05(4H, m)

MS (FAB, m/e): 498(M+H)

EXAMPLES 57 to 66

The same starting material as Example 56 was reacted with each of the compounds prepared in Preparations 19 to 28 according to the same procedure as Example 56 to prepare the respective compounds listed in the following Table 13.

TABLE 13

Examples 57 to 66

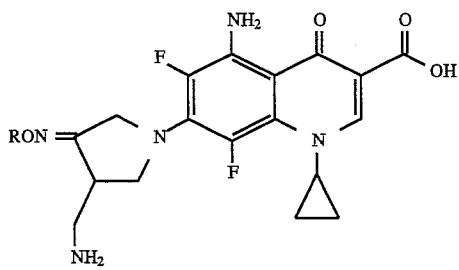

| Examp. No. | R | ¹H NMR, δ (ppm) | NMR solv. | FAB, MS (M+1) | Reac. time (hr) | Yield (%) |
|---|---|---|---|---|---|---|
| 57 | ―CH₂―C₆H₄―OCH₃ | 8.4(1H, s), 7.4(2H, bs), 7.2 (2H, d), 7.0(2H, d), 5.1(2H, s), 4.6(2H, m), 4.2(1H, m), 3.9(1H, m), 3.8(3H, s), 3.7(1H, m), 3.0 (1H, m), 2.8–2.6(2H, m), 1.1 (4H, s) | DMSO-d₆ | 528 | 10 | 59 |
| 58 | ―CH₂―C₆H₄―C(CH₃)₃ | 8.4(1H, s), 7.5(2H, d), 7.4(2H, bs), 7.3(2H, d), 5.2(2H, s), 4.6 (2H, m), 4.2(1H, m), 3.9(1H, m), 3.7(1H, m), 3.0(1H, m), 2.8–2.6 (2H, m), 1.4(9H, s), 1.1(4H, s) | DMSO-d₆ | 554 | 17 | 67 |
| 59 | ―CH₂―C₆H₄―F | 8.4(1H, s), 7.4(4H, m), 7.1(2H, m), 5.1(2H, s), 4.6(2H, m), 4.2 (1H, m), 3.9(1H, m), 3.7(1H, m), 3.0(1H, m), 2.8–2.6(2H, m), 1.1 (4H, s) | DMSO-d₆ | 516 | 17 | 55 |
| 60 | ―CH₂―C₆H₄―NO₂ | 8.4(1H, s), 8.2(2H, d), 7.6(2H, d), 7.4(2H, bs), 5.3(2H, s), 4.6 (2H, m), 4.2(1H, m), 3.9(1H, m), 3.7(1H, m), 3.0(1H, m), 2.8–2.6 (2H, m), 1.1(4H, s) | DMSO-d₆ | 543 | 17 | 56 |
| 61 | ―CH₂―C₆H₄―CN | 8.4(1H, s), 7.9–7.4(6H, m), 5.3 (2H, s), 4.6(2H, m), 4.2(1H, m), 3.9(1H, m), 3.7(1H, m), 3.0(1H, m), 2.8–2.6(2H, m), 1.1(4H, s) | DMSO-d₆ | 523 | 18 | 62 |
| 62 | ―CH₂―C₆H₃―OCH₂O― | 8.4(1H, s), 7.3(2H, bs), 7.0 (3H, m), 6.2(2H, s), 5.2(2H, s), 4.6(2H, m), 4.2(1H, m), 3.9(1H, m), 3.7(1H, m), 3.0(1H, m), 2.8–2.6(2H, m), 1.1(4H, s) | DMSO-d₆ | 542 | 18 | 65 |
| 63 | ―CH₂―pyridyl | 8.5(3H, m), 7.6(1H, d), 7.4(1H, q), 7.3(2H, bs), 5.3(2H, s), 4.6 (2H, m), 4.2(1H, m), 3.9(1H, m), 3.7(1H, m), 3.0(1H, m), 2.8–2.6 (2H, m), 1.1(4H, s) | DMSO-d₆ | 499 | 17 | 52 |

TABLE 13-continued

Examples 57 to 66

| Examp. No. | R | $^1$H NMR, δ (ppm) | NMR solv. | FAB, MS (M+1) | Reac. time (hr) | Yield (%) |
|---|---|---|---|---|---|---|
| 64 | (3-furylmethyl) | 8.4(1H, s), 7.5–7.4(4H, m), 6.5 (1H, m), 5.0(2H, m), 4.6(2H, m), 4.2(1H, m), 3.9(1H, m), 3.7(1H, m), 3.0(1H, m), 2.8–2.6(2H, m), 1.1(4H, s) | DMSO-$d_6$ | 488 | 18 | 49 |
| 65 | (3,4-dihydroxyphenyl)(COOH)methyl | 8.4(1H, s), 7.4(2H, bs), 7.1 (3H, m), 6.7(1H, s), 4.6(2H, m), 4.2(1H, m), 3.9(1H, m), 3.7(1H, m), 3.0(1H, m), 2.8–2.6(2H), 1.1(4H, s) | DMSO-$d_6$ | 574 | 18 | 43 |
| 66 | (6-fluorobenzothiazol-2-yl)methyl | 8.4(1H, s), 8.2(1H, m), 7.9(1H, m), 7.4(3H, m), 5.6(2H, s), 4.6 (2H, m), 4.2(1H, m), 3.9(1H, m), 3.7(1H, m), 3.0(1H, m), 2.8–2.6 (2H, m), 1.1(4H, s) | DMSO-$d_6$ | 573 | 17 | 65 |

EXAMPLE 67

Synthesis of 7-(4-aminomethyl-3-benzyloxyimino-pyrrolidin-1-yl)-1-(2,4-difluorophenyl)-6-fluoro-1,4-dihydro-4-oxo-1,8-naphthyridine-3-carboxylic acid

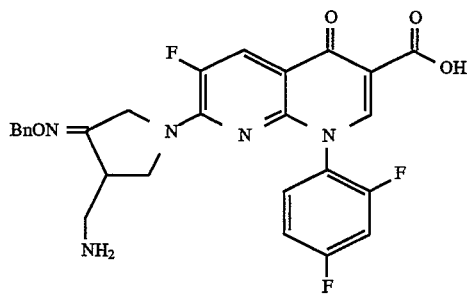

806 mg of 7-chloro-1(2,4-difluorophenyl)-6-fluoro-1,4-dihydro-4-oxo-1,8-naphthyridine-3-carboxylic acid and 438 mg of the compound prepared in Preparation 8 were suspended in 15 ml of acetonitrile and then 913 mg of 1,8-diazabicyclo[5.4.0]undec-7-ene(DBU) was slowly added thereto. The reaction mixture was stirred for one hour at room temperature, and after adding 15 ml of water, was then stirred for further 30 minutes and filtered. The filtered solid product was washed with water and acetonitrile to obtain 524 mg (Yield: 65%) of the title compound.

$^1$H NMR (DMSO-$d_6$, ppm): δ8.82(1H, s), 8.21(1H, d), 7.85(1H, m), 7.56(1H, m), 7.40(6H, m), 5.16(2H, s), 4.76 (2H, s), 4.18(1H, m), 3.94(1H, m), 3.81(1H, m), 3.34(2H, m), 3.04(1H, m), 2.82(1H, m), 2.73(1H, m), 1.30–1.00 (4H, m)

MS (FAB, m/e): 538(M+H)

EXAMPLES 68 to 77

The same starting material as Example 67 was reacted with each of the compounds prepared in Preparations 19 to 28 according to the same procedure as Example 67 to prepare the respective compounds listed in the following Table 14.

TABLE 14

Examples 68 to 77

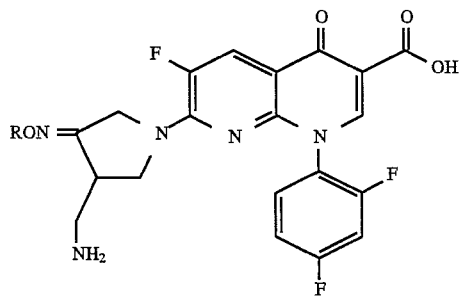

| Examp. No. | R | $^1$H NMR, δ (ppm) | NMR solv. | FAB, MS (M+1) | Reac. time (hr) | Yield (%) |
|---|---|---|---|---|---|---|
| 68 | ‐CH$_2$‐C$_6$H$_4$‐OCH$_3$ | 8.9(1H, s), 8.1(1H, d), 7.8(1H, m), 7.6(1H, dd), 7.3(3H, m), 7.1(2H, d), 5.2(2H, s), 4.3(2H, s), 4.0(1H, m), 3.9(1H, m), 3.8(3H, s), 3.0(1H, m), 2.8–2.6(2H, m) | DMSO-d$_6$ | 568 | 20 | 78 |
| 69 | ‐CH$_2$‐C$_6$H$_4$‐C(CH$_3$)$_3$ | 8.9(1H, s), 8.1(1H, d), 7.8(1H, m), 7.6(2H, m), 7.3(2H, m), 5.2(2H, s), 4.3(2H, s), 3.9(1H, m), 3.0(1H, m), 2.8–2.6(2H, m), 1.5(9H, s) | DMSO-d$_6$ | 594 | 10 | 80 |
| 70 | ‐CH$_2$‐C$_6$H$_4$‐F | 8.9(1H, s), 8.1(1H, d), 7.8(1H, m), 7.6(1H, dd), 7.4(2H, m), 7.3(1H, dd), 7.1(2H, m), 5.1(2H, s), 4.3(2H, s), 4.0(1H, m), 3.9(1H, m), 3.0(1H, m), 2.8–2.6(2H, m) | DMSO-d$_6$ | 556 | 15 | 81 |
| 71 | ‐CH$_2$‐C$_6$H$_4$‐NO$_2$ | 8.9(1H, s), 8.3(2H, d), 8.1(1H, d), 7.8(1H, m), 7.7(2H, d), 7.6(1H, dd), 7.3(1H, m), 5.3(2H, s), 4.3(2H, s), 4.0(1H, m), 3.9(1H, m), 3.0(1H, m), 2.8–2.6(2H, m) | DMSO-d$_6$ | 583 | 15 | 75 |
| 72 | ‐CH$_2$‐C$_6$H$_4$‐CN | 8.8(1H, s), 8.1(1H, d), 7.9–7.4(6H, m), 7.3(1H, dd), 5.3(2H, s), 4.3(2H, s), 4.0(1H, m), 3.9(1H, m), 3.0(1H, m), 2.8–2.6(2H, m) | DMSO-d$_6$ | 563 | 15 | 80 |
| 73 | ‐CH$_2$‐C$_6$H$_3$(OCH$_2$O) | 8.8(1H, s), 8.1(1H, d), 7.8(1H, m), 7.6(1H, dd), 7.3(1H, dd), 7.0(3H, m), 6.2(2H, s), 5.1(2H, s), 4.3(2H, s), 4.0(1H, m), 3.9(1H, m), 3.0(1H, m), 2.8–2.6(2H, m) | DMSO-d$_6$ | 582 | 15 | 87 |

TABLE 14-continued

Examples 68 to 77

| Examp. No. | R | $^1$H NMR, δ (ppm) | NMR solv. | FAB, MS (M+1) | Reac. time (hr) | Yield (%) |
|---|---|---|---|---|---|---|
| 74 | (3-pyridylmethyl) | 8.8(1H, s), 8.6(1H, s), 8.5(1H, q), 7.8(2H, m), 7.6(1H, dd), 7.4 (1H, q), 7.3(1H, dd), 5.2(2H, s), 4.3(2H, s), 4.0(1H, m), 3.9 (1H, m), 3.0(1H, m), 2.8–2.6 (2H, m) | DMSO-$d_6$ | 539 | 15 | 70 |
| 75 | (3-furylmethyl) | 8.8(1H, s), 8.1(1H, d), 7.8(1H, m), 7.6(1H, dd), 7.5(1H, d), 7.45(1H, dd), 6.6(1H, m), 5.0 (2H, m), 4.3(2H, s), 4.0(1H, m), 3.9(1H, m), 3.0(1H, m), 2.8–2.6(2H, m) | DMSO-$d_6$ | 528 | 10 | 69 |
| 76 | (α-carboxy-3,4-dihydroxybenzyl) | 8.8(1H, s), 8.1(1H, d), 7.8(1H, m), 7.6(1H, dd), 7.3(1H, dd), 7.1(3H, m), 6.7(1H, s), 4.3(2H, s), 4.0(1H, m), 3.9(1H, m), 3.0 (1H, m), 2.8–2.6(2H, m) | DMSO-$d_6$ | 614 | 20 | 59 |
| 77 | (6-fluorobenzothiazol-2-ylmethyl) | 8.8(1H, s), 8.2(1H, m), 8.1(1H, d), 8.0(1H, m), 7.8(1H, d), 7.6 (1H, dd), 7.4(1H, m), 7.3(1H, dd), 5.6(2H, s), 4.3(2H, s), 4.0 (1H, m), 3.9(1H, m), 3.0(1H, m), 2.8–2.6(2H, m) | DMSO-$d_6$ | 613 | 10 | 82 |

EXAMPLE 78

Synthesis of 7-(4-aminomethyl-3-benzyloxyiminopyrrolidin-1-yl)-1-ethyl-6,8-difluoro-1,4-dihydro-4-oxoquinoline-3-carboxylic acid

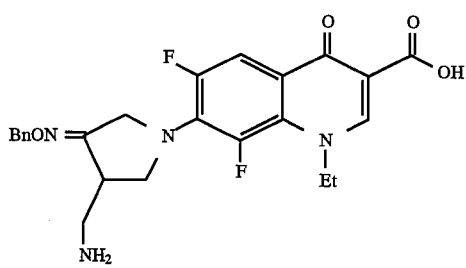

353 mg of 1-ethyl-6,7,8-trifluoro-1,4-dihydro-4-oxoquinoline-3-carboxylic acid and 380 mg of the compound prepared in Preparation 8 were suspended in 15 ml of acetonitrile and then 593 mg of 1,8-diazabicyclo[5.4.0]undec-7-ene(DBU) was slowly added thereto. The reaction mixture was stirred for 2.5 hours at 80° C., and after adding 15 ml of water, was then stirred for further 30 minutes under cold water bath and filtered. The filtered solid product was washed with water, acetonitrile and ethyl ether to obtain 391 mg (Yield: 64%) of the title compound.

$^1$H NMR (DMSO-$d_6$, ppm): δ8.8(1H, s), 7.8(1H, d), 7.40(5H, m), 5.10(2H,s), 4.6(2H, q), 4.4(2H, dd), 4.0(1H, m), 3.7(1H, m), 3.1(1H, m), 2.8(2H, ddd), 1.46(3H, t)

MS (FAB, m/e): 471(M+H)

EXAMPLES 79 to 88

The same starting material as Example 78 was reacted with each of the compounds prepared in Preparations 19 to 28 according to the same procedure as Example 78 to prepare the respective compounds listed in the following Table 15.

TABLE 15

Examples 79 to 88

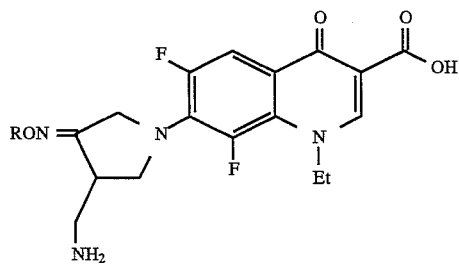

| Examp. No. | R | $^1$H NMR, δ (ppm) | NMR solv. | FAB, MS (M+1) | Reac. time (hr) | Yield (%) |
|---|---|---|---|---|---|---|
| 79 | —CH₂—C₆H₄—OCH₃ | 8.8(1H, s), 7.8(1H, d), 7.4(2H, d), 7.1(2H, d), 5.0(2H, s), 4.5 (2H, q), 4.4(2H, s), 4.2(1H, m), 3.9(1H, m), 3.7(3H, s), 3.1(1H, m), 2.9–2.7(2H, m), 1.45(3H, t) | DMSO-d₆ | 501 | 4 | 73 |
| 80 | —CH₂—C₆H₄—C(CH₃)₃ | 8.8(1H, s), 7.8(1H, d), 7.4(2H, d), 7.2(2H, d), 5.1(2H, s), 4.5 (2H, q), 4.4(2H, s), 4.1(1H, m), 3.9(1H, m), 3.1(1H, m), 2.9–2.7 (2H, m), 1.45(3H, t), 1.4(9H, s) | DMSO-d₆ | 527 | 2.5 | 77 |
| 81 | —CH₂—C₆H₄—F | 8.8(1H, s), 7.8(1H, d), 7.3(2H, m), 7.0(2H, m), 5.0(2H, s), 4.5 (2H, q), 4.4(2H, s), 4.2(1H, m), 3.9(1H, m), 3.1(1H, m), 2.9–2.7 (2H, m), 1.45(3H, t) | DMSO-d₆ | 489 | 3 | 80 |
| 82 | —CH₂—C₆H₄—NO₂ | 8.8(1H, s), 8.3(2H, d), 7.8(1H, d), 7.7(2H, d), 5.3(2H, s), 4.5 (2H, q), 4.4(2H, s), 4.2(1H, m), 3.9(1H, m), 3.1(1H, m), 2.9–2.7 (2H, m), 1.45(3H, t) | DMSO-d₆ | 516 | 3 | 75 |
| 83 | —CH₂—C₆H₄—CN | 8.8(1H, s), 7.9–7.4(5H, m), 5.3 (2H, s), 4.5(2H, q), 4.4(2H, s), 4.2(1H, m), 3.9(1H, m), 3.1(1H m), 2.9–2.7(2H, m), 1.45(3H, t) | DMSO-d₆ | 496 | 3 | 80 |

TABLE 15-continued

Examples 79 to 88

| Examp. No. | R | ¹H NMR, δ (ppm) | NMR solv. | FAB, MS (M+1) | Reac. time (hr) | Yield (%) |
|---|---|---|---|---|---|---|
| 84 | (3,4-ethylenedioxybenzyl) | 8.8(1H, s), 7.8(1H, d), 6.8(3H, m), 6.0(2H, s), 5.0(2H, s), 4.5 (2H, q), 4.4(2H, s), 4.2(1H, m), 3.9(1H, m), 3.1(1H, m), 2.9–2.7 (2H, m), 1.45(3H, t) | DMSO-$d_6$ | 515 | 4 | 69 |
| 85 | (3-pyridylmethyl) | 8.8(1H, s), 8.6(2H, m), 7.8(2H, m), 7.4(1H, q), 5.3(2H, s), 4.5 (2H, q), 4.4(2H, s), 4.2(1H, m), 3.9(1H, m), 3.1(1H, m), 2.9–2.7 (2H, m), 1.45(3H, t) | DMSO-$d_6$ | 471 | 2 | 70 |
| 86 | (3-furylmethyl) | 8.8(1H, s), 7.8(1H, d), 7.5(2H, m), 6.5(1H, m), 5.0(2H, m), 4.5 (2H, q), 4.4(2H, s), 4.2(1H, m), 2.9(1H, m), 3.1(1H, m), 2.9–2.7 (2H, m), 1.45(3H, t) | DMSO-$d_6$ | 461 | 2 | 67 |
| 87 | (α-carboxy-3,4-dihydroxybenzyl) | 8.8(1H, s), 7.8(1H, d), 7.1(3H, m), 6.7(1H, s), 4.5(2H, q), 4.4 (2H, s), 4.2(1H, m), 3.9(1H, m), 3.1(1H, m), 2.9–2.7(2H, m), 1.45(3H, t) | DMSO-$d_6$ | 547 | 3 | 63 |
| 88 | (α-(6-fluorobenzothiazol-2-yl)ethyl) | 8.8(1H, s), 8.2(1H, m), 7.9(1H, m), 7.8(1H, d), 7.4(1H, m), 5.6 (2H, s), 4.5(2H, q), 4.4(2H, s), 4.2(1H, m), 3.9(1H, m), 3.1(1H, m), 2.9–2.7(2H, m), 1.5(3H, t) | DMSO-$d_6$ | 546 | 4 | 70 |

EXAMPLE 89

Synthesis of 7-(4-aminomethyl-3-t-butyloxyimino-pyrrolidin-1-yl)-1-cyclopropyl-6-fluoro-4-dihydro-4oxo-1,8-naphthyridine-3-carboxylic acid

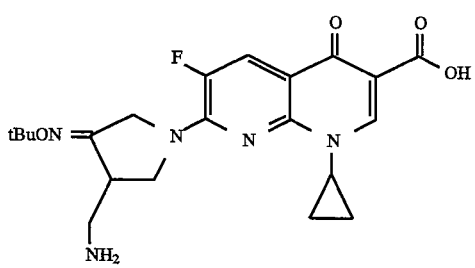

141 mg (0.5 mmole) of 7-chloro-1-cyclopropyl-6-fluoro-4-oxo-1,4-dihydro[1,8]naphthyridine-3-carboxylic acid and 143 mg (0.55 mmole) of 4-aminomethyl-pyrrolidin-3-one t-butyloxime dihydrochloride were thoroughly suspended in 2.5 ml of acetonitrile. Then, 230 mg (1.5 mmole) of 1,8-diazabicyclo[5.4.0]undec-7-ene was slowly added dropwise thereto. The reaction mixture was stirred for 30 minutes at room temperature, and after adding 1 ml of water, was then vigorously stirred for 10 minutes and filtered. The filtered solid product was successively washed with acetonitrile-water (4:1 v/v, 2 ml) and acetonitrile (2 ml×2) and then with ether and dried to obtain 132 mg (Yield: 61%) of the title compound.

$^1$H NMR (DMSO-d$_6$, ppm): δ8.6(1H, s), 8.1(1H, d), 4.6(2H, s), 4.2(1H, dd), 3.9(1H, dd), 3.7 (1H, m), 3.1(1H, dd), 2.9–2.7 (2H, ddd), 1.3(9H, s), 1.2(2H, m), 1.1(2H, m)

FAB MS (POS): 432[M+H]$^+$

EXAMPLE 90

Synthesis of 7-(3-aminomethyl-4-t-butyloxyiminopyrrolidin-1-yl)-1-cyclopropyl-6,8-difluoro-4-oxo-1,4-dihydroquinoline-3-carboxylic acid

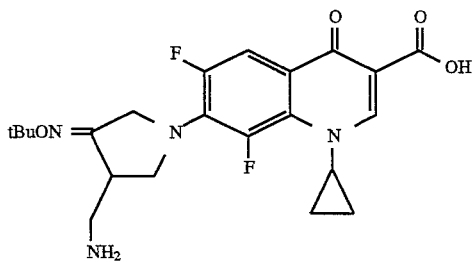

141 mg (0.5 mmole) of 1-cyclopropyl-6,7,8-trifluoro-4-oxo-1,4-dihydroquinoline-3-carboxylic acid and 143 mg (0.55 mmole) of 3-aminomethyl-4-t-butyloxyiminopyrrolidine dihydrochloride were refluxed for 2.5 hours under heating according to the same manner as Example 89 and cooled down to room temperature. Then, the resulting product was then separated and purified with preparative HPLC to obtain 151 mg (Yield: 67%) of the title compound.

$^1$H NHR (DMSO-d$_6$, ppm): δ8.8(1H, s), 7.8(1H, d), 4.5(2H, s), 4.3(1H, m), 3.9(1H, m), 3.8(1H, m), 2.9(1H, m), 2.8–2.7(2H, m), 1.3(9H, s), 1.15(4H, s)

FAB MS (POS): 449[M+H]$^+$

EXAMPLE 91

Synthesis of 8-chloro-1-cyclopropyl-6-fluoro-[7-(3-aminomethyl-4-t-butyloxyiminopyrrolidin-1-yl)]-4-oxo-1,4-dihydroquinoline-3-carboxylic acid

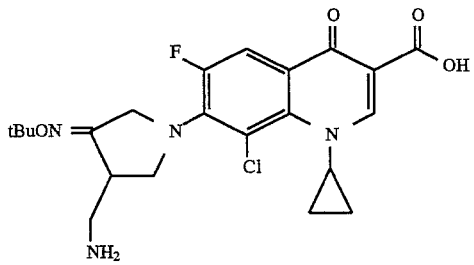

150 mg (0.5 mmole) of 8-chloro-1-cyclopropyl-6,7-difluoro-4-oxo-1,4-dihydroquinoline-3-carboxylic acid was reacted according to the same manner as Example 90. Then, the reaction solution as concentrated and the residue was purified with preparative HPLC to obtain 148 mg (Yield: 64%) of the title compound.

$^1$H NMR (DMSO-d$_6$, ppm): δ8.7(1H, s), 7.9(1H, d), 4.4(2H, s), 4.3(1H, m), 3.8(1H, m), 3.7(1H, m), 3.0(1H, m), 2.9–2.7(2H, m), 1.3(9H, s), 1.2–0.9(4H, m)

FAB MS(POS): [M+H]$^+$=465

EXAMPLE 92

Synthesis of 7-(3-aminomethyl-4-t-butyloxyiminopyrrolidin-1-yl)-1-cyclopropyl-6-fluoro-4-oxo-1,4-dihydroquinoline-3-carboxylic acid

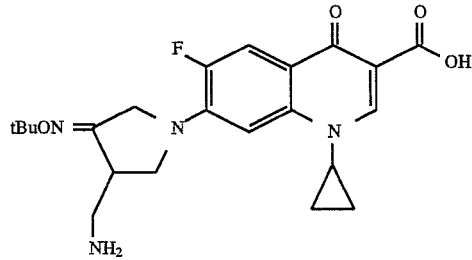

132 mg (0.5 mmole) of 1-cyclopropyl-6,7-difluoro-4-oxo-1,4-dihydroquinoline-3-carboxylic acid was refluxed for 3.5 hours under heating according to the same manner as Example 89. Then, the resulting residue was subjected to preparative HPLC to obtain 129 mg (Yield: 60%) of the title compound.

$^1$H NMR (DMSO-d$_6$, ppm): δ8.6(1H, s), 7.8(1H, d), 7.2(1H, d), 4.4(2H, s), 3.9(1H, m), 3.8(1H, m), 3.7(1H, m), 3.0(1H, m), 2.9–2.7(2H, m), 1.4(9H, s), 1.3–1.1(4H, m)

FAB MS (POS): [M+H]$^+$=431

EXAMPLE 93

Synthesis of 5-amino-7-(3-aminomethyl-4-t-butyloxyiminopyrrolidin-1-yl)-1-cyclopropyl-4-oxo-1,4-dihydroquinoline-3-carboxylic acid

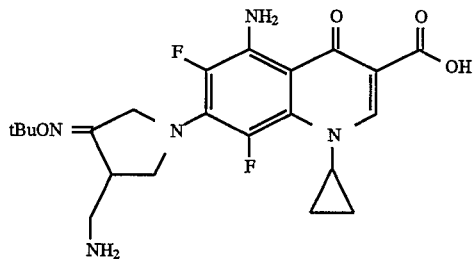

148 mg (0.5 mmole) of 5-amino-1-cyclopropyl-6,7,8-trifluoro-4-oxo-1,4-dihydroquinoline-3-carboxylic acid was refluxed for 8 hours under heating according to the same manner as Example 89. Then, the resulting residue was purified with preparative HPLC to obtain 151 mg (Yield: 65%) of the title compound.

$^1$H NMR (DMSO-d$_6$, ppm): δ8.6(1H, s), 7.5(2H, br), 4.3(2H, s), 4.0–3.8(3H, m), 3.2(1H, m), 2.8–2.6(2H, m), 1.3(9H, s), 1.1(4H, m)

FAB MS(POS): [M+H]$^+$=464

EXAMPLE 94

Synthesis of 7-(3-aminomethyl-4-t-butyloxyiminopyrrolidin-1l-yl)-1-cyclopropyl-6-fluoro-8-methoxy-4-oxo-1,4-dihydroquinoline-3-carboxylic acid

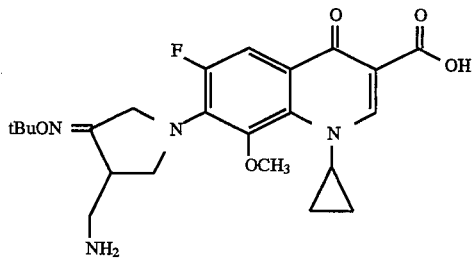

148 mg (0.5 mmole) of 1-cyclopropyl-6,7-difluoro-8-methoxy-4-oxo-1,4-dihydroquinoline-3-carboxylic acid was refluxed for 10 hours under heating according to the same manner as Example 89. Then, the resulting residue was purified with preparative HPLC to obtain 92 mg (Yield: 40%) of the title compound.

$^1$H NMR (DMSO-d$_6$, ppm): δ8.9(1H, s), 7.8(1H, d), 4.5(2H, s), 4.3(1H, m), 4.1(1H, m), 3.9(1H, m), 3.0(1H, m), 2.8–2.7(2H, m), 2.7(3H, s), 1.3(9H, s), 1.25(2H, m), 0.9(2H, s)

FAB MS(POS): [M+H]$^+$=461

EXAMPLE 95

Synthesis of 7-(3-aminomethyl-4-t-butyloxyiminopyrrolidin-1-yl)-1-(2,4-difluorophenyl)-6-fluoro-4-oxo-1,4-dihydro-1,8-naphthyridine-3-carboxylic acid

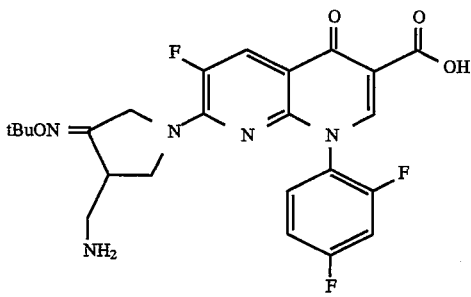

168 mg (0.5 mmole) of 6,7-difluoro-1-(2,4-difluorophenyl)-4-oxo-1,4-dihydro-naphthyridine-3-carboxylic acid and 143 mg (0.55 mmole) of 3-aminomethyl-4-t-butyloxyiminopyrrolidine dihydrochloride were suspended in 3 ml of dry acetonitrile. Then, 230 mg (1.5 mmole) of 1,8-diazabicyclo[5.4.0]undec-7-ene was added thereto, and the reaction mixture was stirred for 15 minutes at room temperature and then treated according to the same manner as Example 89 to obtain 203 mg (Yield: 81%) of the title compound.

$^1$H NMR (DMSO-d$_6$, ppm): δ8.9(1H, s), 8.1(1H, d), 7.8(1H, m), 7.6(1H, dd), 7.3(1H, dd), 4.3(2H, s), 4.0(1H, m), 3.9(1H, m), 3.0(1H, m), 2.8–2.6(2H, m), 1.3(9H, s)

FAB MS(POS): [M+H]$^+$=504

EXAMPLE 96

Synthesis of 7-(3-aminomethyl-4-t-butyloxyiminopyrrolidin-1-yl)- 6,8-difluoro-1-ethyl-4-oxo-1,4-dihydroquinoline-3-carboxylic acid

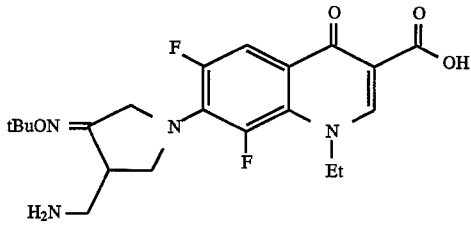

136 mg (0.5 mmole) of 1-ethyl-6,7,8-trifluoro-4-oxo-1,4-dihydroquinoline-3-carboxylic acid was refluxed for 5 hours under heating according to the same manner as Example 89. Then, the resulting residue was purified with preparative HPLC to obtain 170 mg (Yield: 78%) of the title compound.

$^1$H NMR (DMSO-d$_6$, ppm): δ8.8(1H, s), 7.8(1H, d), 4.5(2H, q), 4.4(2H, s), 4.2(1H, m), 3.9(1H, m), 3.1(1H, m), 2.9–2.7(2H, m), 1.45(3H, t), 1.3(9H, s)

FAB MS(POS): [M+H]$^+$=437

EXAMPLES 97 to 176

The amine compounds prepared in Preparations 41 to 50 were treated according to the same procedure as Examples 89 to 96 to prepare the respective compounds 97 to 176 of which NMR and MS data are listed in the following Tables 16 to 23.

TABLE 16

Examples 97 to 106

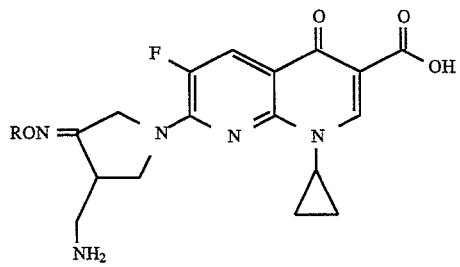

| Examp. No. | R | $^1$H NMR, δ (ppm) | NMR solv. | FAB, MS (M+1) | Reac. time (hr) | Yield (%) |
|---|---|---|---|---|---|---|
| 97 | isopropyl | 8.6(1H, s), 8.0(1H, d), 4.7(1H, m), 4.6(2H, s), 4.2(1H, m), 3.9 (1H, m), 3.7(1H, m), 3.0(1H, m), 2.9–2.7.(2H, m), 1.2–1.0(4H, m), 0.9(6H, d) | DMSO-d$_6$ | 418 | 10 | 73 |
| 98 | cyclobutylmethyl | 8.6(1H, s), 8.05(1H, d), 4.8 (1H, m), 4.7(2H, s), 4.2(1H, m), 4.0(1H, m), 3.7(1H, m), 3.0(1H, m), 2.9–2.7(2H, m), 2.2(2H, m), 2.1(2H, m), 1.7(1H, m), 1.5(1H, m), 1.2–1.0(4H, m) | DMSO-d$_6$ | 430 | 10 | 63 |
| 99 | cyclopentylmethyl | 8.6(1H, s), 8.0(1H, d), 4.7(1H, m), 4.5(2H, s), 4.2(1H, m), 3.9 (1H, m), 3.7(1H, m), 3.1(1H, m), 2.9–2.8(2H, m), 1.7(4H, s), 1.6 (2H, m), 1.5(2H, m), 1.2–1.0 (4H, m) | DMSO-d$_6$ | 444 | 50 | 77 |
| 100 | tetrahydrofuranylmethyl | 8.6(1H, s), 8.0(1H, d), 4.8(1H, m), 4.6(2H, s), 4.2(1H, m), 3.9 (1H, m), 3.8–3.6(5H, m), 3.1 (1H, m), 2.9–2.7(2H, m), 2.3– 1.9(2H, m), 1.2–1.0(4H, m) | DMSO-d$_6$ | 446 | 30 | 61 |
| 101 | cyclopropylmethyl | 8.65(1H, s), 8.05(1H, d), 4.6 (2H, s), 4.25(1H, m), 3.9(1H, m), 3.85(2H, dd), 3.75(1H, m), 3.1(1H, m), 3.0–2.8(2H, m), 1.3–1.0(5H, m), 0.5(2H, m), 0.3(2H, m) | DMSO-d$_6$ | 430 | 30 | 84 |
| 102 | isobutyl | 8.6(1H, s), 8.0(1H, d), 4.6(2H, s), 4.2(1H, m), 3.95(1H, m), 3.8 (2H, d), 3.7(1H, m), 3.05(1H, m), 2.9–2.7(2H, m), 1.9(1H, m), 1.2–1.0(4H, m), 0.9(6H, d) | DMSO-d$_6$ | 432 | 15 | 80 |
| 103 | propargyl | 8.60(1H, s), 8.05(1H, d), 4.74 (2H, s), 4.60(2H, s), 4.21(1H, m), 3.97(1H, m), 3.75(1H, m), 3.50(1H, s), 3.35(2H, s), 3.08 (1H, m), 2.90–2.70(2H, m), 1.30–1.05(4H, m) | DMSO-d$_6$ | 414 | 90 | 63 |
| 104 | butynyl | 8.6(1H, s), 8.0(1H, d), 4.6(2H, s), 4.2(1H, m), 4.1(2H, t), 3.9 (1H, m), 3.7(1H, m), 3.1(1H, m), 2.9–2.7(2H, m), 2.8(1H, s), 2.5 (2H, t), 1.2–1.0(4H, m) | DMSO-d$_6$ | 428 | 15 | 65 |
| 105 | methoxyethyl | 8.6(1H, s), 8.0(1H, d), 4.6(2H, s), 4.2(1H, m), 3.9(1H, m), 3.7 (1H, m), 3.4(2H, s), 3.3(3H, s), 3.0(1H, m), 2.8–2.6(2H, m), 1.2–1.0(4H, m) | DMSO-d$_6$ | 420 | 20 | 52 |

TABLE 16-continued

Examples 97 to 106

| Examp. No. | R | ¹H NMR, δ (ppm) | NMR solv. | FAB, MS (M+1) | Reac. time (hr) | Yield (%) |
|---|---|---|---|---|---|---|
| 106 | ⟶Cl | 8.6(1H, s), 8.05(1H, d), 4.6 (2H, s), 4.3(2H, t), 4.2(1H, m), 3.9(1H, m), 3.8(2H, t), 3.7(1H, m), 3.1(1H, m), 2.9–2.7(2H, m), 1.2–1.0(4H, m) | DMSO-$d_6$ | 438 | 10 | 50 |

TABLE 17

Examples 107 to 116

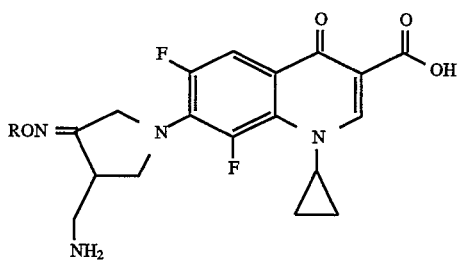

| Examp. No. | R | ¹H NMR, δ (ppm) | NMR solv. | FAB, MS (M+1) | Reac. time (hr) | Yield (%) |
|---|---|---|---|---|---|---|
| 107 | isopropyl | 8.8(1H, s), 7.8(1H, d), 4.7(1H, m), 4.5(2H, s), 4.1(1H, m), 3.9 (1H, m), 3.8(1H, m), 2.9(1H, m), 2.8–2.7(2H, m), 1.15(4H, s), 0.9(6H, d) | DMSO-$d_6$ | 435 | 2 | 69 |
| 108 | cyclobutyl | 8.8(1H, s), 7.8(1H, d), 4.8(1H, m), 4.4(2H, s), 4.1(1H, m), 3.9 (1H, m), 3.8(1H, m), 2.9(1H, m), 2.8–2.7(2H, m), 2.2(2H, m), 2.1 (2H, m), 1.7(1H, m), 1.5(1H, m), 1.15(4H, s) | DMSO-$d_6$ | 447 | 2 | 61 |
| 109 | cyclopentyl | 8.8(1H, s), 7.8(1H, d), 4.7(1H, m), 4.5(2H, s), 4.1(1H, m), 3.9 (1H, m), 3.8(1H, m), 2.91H, m), 2.8–2.7(2H, m), 1.7(4H, s), 1.6 (2H, m), 1.5(2H, m), 1.15(2H, m), 1.0(2H, m) | DMSO-$d_6$ | 461 | 2 | 63 |
| 110 | tetrahydrofuranyl | 8.8(1H, s), 7.8(1H, d), 4.8(1H, m), 4.5(2H, s), 4.1(1H, m), 3.9 (1H, m), 3.8–3.6(4H, m), 3.1 (1H, m), 2.8–2.7(2H, m), 2.3– 1.9(2H, m), 1.2–1.0(4H, s) | DMSO-$d_6$ | 463 | 2 | 54 |

TABLE 17-continued

Examples 107 to 116

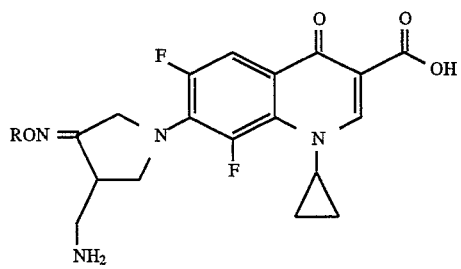

| Examp. No. | R | $^1$H NMR, δ (ppm) | NMR solv. | FAB, MS (M+1) | Reac. time (hr) | Yield (%) |
|---|---|---|---|---|---|---|
| 111 | cyclopropylmethyl | 8.8(1H, s), 7.8(1H, d), 4.5 (2H, s), 4.1(1H, m), 3.9(1H, m), 3.8(2H, dd), 3.75(1H, m), 3.1 (1H, m), 2.8–2.7(2H, m), 1.15 (4H, m), 1.05(1H, m), 0.5(2H, m), 0.3(2H, m) | DMSO-$d_6$ | 447 | 2 | 59 |
| 112 | isobutyl | 8.8(1H, s), 7.8(1H, d), 4.5(2H, s), 4.1(1H, m), 3.9(1H, m), 3.8 (2H, d), 3.75(1H, m), 3.0(1H, m), 2.8–2.7(2H, m), 1.9(1H, m), 1.2–1.0(4H, m), 0.9(6H, d) | DMSO-$d_6$ | 449 | 2 | 64 |
| 113 | propargyl | 8.8(1H, s), 7.8(1H, d), 4.62 (2H, s), 4.3(2H, s), 4.1(1H, m), 3.9(1H, m), 3.8(1H, m), 3.5 (1H, s), 2.9(1H, m), 2.8–2.7 (2H, m), 1.15(4H, m) | DMSO-$d_6$ | 431 | 4 | 55 |
| 114 | 3-butynyl | 8.8(1H, s), 7.8(1H, d), 4.5(2H, s), 4.1(1H, m), 4.0(2H, t), 3.9 (1H, m), 3.8(1H, m), 3.1(1H, m), 2.8–2.7(2H, m), 2.7(1H, s), 2.5 (2H, t), 1.2(4H, m) | DMSO-$d_6$ | 445 | 2 | 65 |
| 115 | -CH$_2$CH$_2$OCH$_3$ | 8.8(1H, s), 7.8(1H, d), 4.5(2H, s), 4.1(1H, m), 3.9(1H, m), 3.8 (1H, m), 3.3(2H, s), 3.1(3H, s), 3.0(1H, m), 2.8–2.7(2H, m), 1.15(4H, m) | DMSO-$d_6$ | 437 | 1.5 | 47 |
| 116 | -CH$_2$CH$_2$Cl | 8.8(1H, s), 7.8(1H, d), 4.5(2H, s), 4.3(2H, t), 4.1(1H, m), 3.9 (1H, m), 3.8(2H, t), 3.75(1H, m), 3.0(1H, m), 2.8–2.7(2H, m), 1.15(4H, m) | DMSO-$d_6$ | 455 | 1.5 | 53 |

TABLE 18

Examples 117 to 126

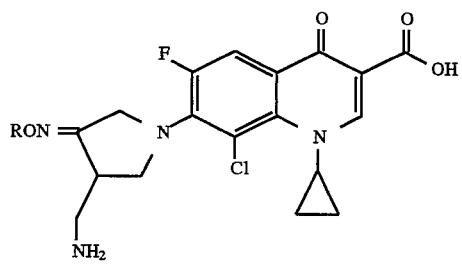

| Examp. No. | R | ¹H NMR, δ (ppm) | NMR solv. | FAB, MS (M+1) | Reac. time (hr) | Yield (%) |
|---|---|---|---|---|---|---|
| 117 | isopropyl | 8.8(1H, s), 7.9(1H, d), 4.7(1H, m), 4.4(2H, s), 4.3(1H, m), 3.8 (1H, m), 3.7(1H, m), 3.0(1H, m), 2.9–2.7(2H, m), 1.8–0.9(4H, m), 0.9(6H, d) | DMSO-$d_6$ | 451 | 2.5 | 68 |
| 118 | cyclobutylmethyl | 8.8(1H, s), 7.9(1H, d), 4.7(1H, m), 4.4(2H, s), 4.3(1H, m), 3.8 (1H, m), 3.7(1H, m), 3.0(1H, m), 2.9–2.7(2H, m), 2.2(2H, m), 2.1(2H, m), 1.7(1H, m), 1.5(1H, m), 1.12–0.9(4H, m) | DMSO-$d_6$ | 463 | 2 | 61 |
| 119 | cyclopentylmethyl | 8.8(1H, s), 7.9(1H, d), 4.7(1H, m), 4.4(2H, s), 4.3(1H, m), 3.8 (1H, m), 3.7(1H, m), 3.0(1H, m), 2.9–2.7(2H, m), 1.7(4H, s), 1.6 (2H, m), 1.5(2H, m), 1.2–0.9 (4H, m) | DMSO-$d_6$ | 477 | 2 | 55 |
| 120 | tetrahydrofuranylmethyl | 8.8(1H, s), 7.9(1H, d), 4.8(1H, m), 4.4(2H, s), 4.3(1H, m), 3.8–3.6(6H, m), 3.0(1H, m), 2.9–2.7 (2H, m), 2.3–1.9(2H, m), 1.2–0.9(4H, m) | DMSO-$d_6$ | 479 | 2.5 | 49 |
| 121 | cyclopropylmethyl | 8.8(1H, s), 7.9(1H, d), 4.4 (2H, s), 4.3(1H, m), 3.8–3.7 (4H, m), 3.0(1H, m), 2.9–2.7 (2H, m), 1.2–0.9(5H, m), 0.5 (2H, m), 0.3(2H, m) | DMSO-$d_6$ | 463 | 2 | 52 |
| 122 | isobutyl | 8.8(1H, s), 7.9(1H, d), 4.4(2H, s), 4.3(1H, m), 3.8–3.7(4H, m), 3.0(1H, m), 2.9–2.7(2H, m), 1.9(1H, m), 1.2–0.9(4H, m), 0.9(6H, d) | DMSO-$d_6$ | 465 | 2 | 60 |
| 123 | propargyl | 8.8(1H, s), 7.9(1H, d), 4.61 (2H, s), 4.4(2H, s), 4.3(1H, m), 3.8(1H, m), 3.5(1H, s), 3.0(1H, m), 2.9–2.7(2H, m), 1.2–0.9(4H, m,) | DMSO-$d_6$ | 447 | 2 | 62 |
| 124 | butynyl | 8.8(1H, s), 7.9(1H, d), 4.4(2H, s), 4.3(1H, m), 4.1(2H, t), 3.8 (1H, m), 3.7(1H, m), 3.0(1H, m), 2.9–2.7(2H, m), 2.8(1H, s), 2.5 (2H, t), 1.2–0.9(4H, m) | DMSO-$d_6$ | 461 | 2.5 | 57 |
| 125 | CH₂OCH₃ | 8.8(1H, s), 7.9(1H, d), 4.4(2H, s), 4.3(1H, m), 3.8(1H, m), 3.7 (1H, m), 3.3(2H, s), 3.1(3H, s), 3.0(1H, m), 2.9–2.7(2H, m), 1.2–0.9(4H, m) | DMSO-$d_6$ | 453 | 1.5 | 51 |

TABLE 18-continued

Examples 117 to 126

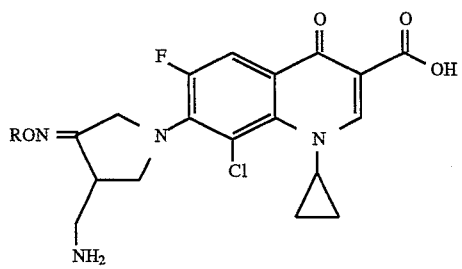

| Examp. No. | R | ¹H NMR, δ (ppm) | NMR solv. | FAB, MS (M+1) | Reac. time (hr) | Yield (%) |
|---|---|---|---|---|---|---|
| 126 | —CH₂—Cl | 8.8(1H, s), 7.9(1H, d), 4.4(2H, s), 4.3(3H, m), 3.8–3.7(4H, m), 3.0(1H, m), 2.9–2.7(2H, m), 1.2–0.9(4H, m) | DMSO-d₆ | 471 | 2 | 64 |

TABLE 19

Examples 127 to 136

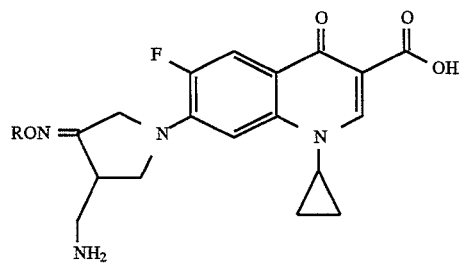

| Examp. No. | R | ¹H NMR, δ (ppm) | NMR solv. | FAB, MS (M+1) | Reac. time (hr) | Yield (%) |
|---|---|---|---|---|---|---|
| 127 | isopropyl | 8.6(1H, s), 7.8(1H, d), 7.2(1H, d), 4.6(1H, m), 4.4(2H, s), 3.9 (1H, m), 3.8(1H, m), 3.7(1H, m), 3.0(1H, m), 2.9–2.7(2H, m), 1.3–1.1(4H, m), 0.9(6H, d) | DMSO-d₆ | 417 | 3 | 55 |
| 128 | cyclobutyl | 8.6(1H, s), 7.8(1H, d), 7.2 (1H, d), 4.7(1H, m), 4.4(2H, s), 3.9(1H, m), 3.8(1H, m), 3.0(1H, m), 2.9–2.7(2H, m), 2.2(2H, m), 2.1(2H, m), 1.7(1H, m), 1.5(2H, m), 1.3–1.1(4H, m) | DMSO-d₆ | 429 | 3 | 52 |
| 129 | cyclopentyl | 8.6(1H, s),7.8(1H, d), 7.2(1H, d), 4.7(1H, m), 4.4(2H, s), 3.9 (1H, m), 3.8(1H, m), 3.7(1H, m), 3.0(1H, m), 2.9–2.7(2H, m), 1.7 (4H, s), 1.6(2H, m), 1.5(2H, m), 1.3–1.1(4H, m) | DMSO-d₆ | 443 | 3 | 59 |
| 130 | tetrahydrofuranyl | 8.6(1H, s), 7.8(1H, d), 7.2(1H, d), 4.8(1H, m), 4.4(2H, s), 3.9 (1H, m), 3.8–3.6(6H, m), 3.0 (1H, m), 2.9–2.7(2H, m), 2.3–1.9(2H, m), 1.3–1.1(4H, m) | DMSO-d₆ | 445 | 3 | 45 |
| 131 | cyclopropylmethyl | 8.6(1H, s), 7.8(1H, d), 7.2(1H, d), 4.6(1H, m), 4.4(2H, s), 3.9 (1H, m), 3.8–3.7(3H, m), 3.1 (1H, m), 2.9–2.7(2H, m), 1.3–1.1(4H, m), 1.0(1H, m), 0.5(2H, m), 0.3(2H, m) | DMSO-d₆ | 429 | 3 | 57 |

TABLE 19-continued
Examples 127 to 136
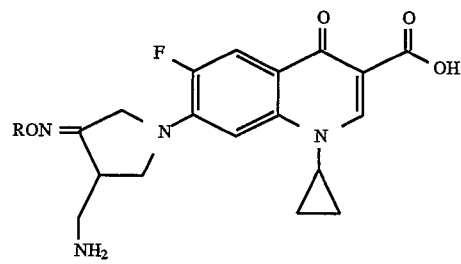
| Examp. No. | R | $^1$H NMR, δ (ppm) | NMR solv. | FAB, MS (M+1) | Reac. time (hr) | Yield (%) |
|---|---|---|---|---|---|---|
| 132 | ![isobutyl] | 8.6(1H, s), 7.8(1H, d), 7.2(1H, d), 4.4(2H, s), 3.9(1H, m), 3.8 (3H, m), 3.7(1H, m), 3.1(1H, m), 2.9–2.7(2H, m), 1.9(1H, m), 1.3–1.1(4H, m), 0.9(6H, d) | DMSO-$d_6$ | 431 | 3 | 76 |
| 133 | ![propargyl] | 8.6(1H, s), 7.8(1H, d), 7.2(1H, d), 4.6(2H, s), 4.4(2H, s), 3.9 (1H, m), 3.8(1H, m), 3.7(1H, m), 3.5(1H, s), 3.0(1H, m), 2.9–2.7(2H, m), 1.3–1.1(4H, m) | DMSO-$d_6$ | 413 | 3 | 49 |
| 134 | ![butynyl] | 8.6(1H, s), 7.8(1H, d), 7.2(1H, d), 4.4(2H, s), 4.1(2H, t), 3.9 (1H, m), 3.8(1H, m), 3.7(1H, m), 3.1(1H, m), 2.9–2.7(2H, m), 2.8(1H, s), 2.5(2H, t), 1.3–1.1(4H, m) | DMSO-$d_6$ | 427 | 3 | 59 |
| 135 | ![CH2CH2OCH3] OCH$_3$ | 8.6(1H, s), 7.8(1H, d), 7.2(1H, d), 4.4(2H, s), 4.1(2H, t), 3.9 (1H, m), 3.8(1H, m), 3.7(1H, m), 3.3(2H, s), 3.2(3H, s), 3.0(1H, m), 2.9–2.7(2H, m), 1.3–1.1 (4H, m) | DMSO-$d_6$ | 419 | 1.5 | 47 |
| 136 | ![CH2CH2Cl] Cl | 8.6(1H, s), 7.8(1H, d), 7.2(1H, d), 4.4(2H, s), 4.3(2H, t), 3.9 (1H, m), 3.8(3H, m), 3.7(1H, m), 3.0(1H, m), 2.9–2.7(2H, m), 1.3–1.1(4H, m) | DMSO-$d_6$ | 437 | 2 | 53 |

TABLE 20

Examples 137 to 146

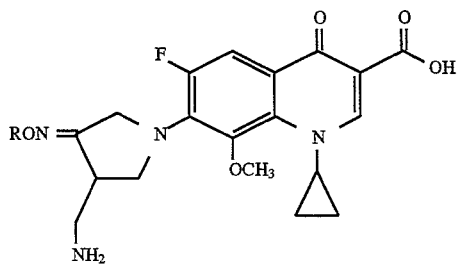

| Examp. No. | R | $^1$H NMR, δ (ppm) | NMR solv. | FAB, MS (M+1) | Reac. time (hr) | Yield (%) |
|---|---|---|---|---|---|---|
| 137 | isopropyl | 8.8(1H, s), 7.8(1H, d), 4.7(1H, m), 4.5(2H, s), 4.3(1H, m), 4.1 (1H, m), 3.9(1H, m), 3.0(1H, m), 2.8–2.7(2H, m), 2.65(3H, s), 1.3(2H, m), 1.0(2H, m), 0.9 (6H, d) | DMSO-$d_6$ | 447 | 9 | 57 |
| 138 | cyclobutyl | 8.8(1H, s), 7.8(1H, d), 4.8(1H, m), 4.7(2H, s), 4.3(1H, m), 4.2 (1H, m), 3.9(1H, m), 3.0(1H, m), 2.9–2.7(2H, m), 2.7(3H, s), 2.2 (2H, m), 2.1(2H, m), 1.6(1H, m), 1.5(1H, m), 1.3(2H, m), 0.95 (2H, m) | DMSO-$d_6$ | 459 | 12 | 65 |
| 139 | cyclopentyl | 8.8(1H, s), 7.8(1H, d), 4.7(1H, m), 4.5(2H, s), 4.3(1H, m), 4.2 (1H, m), 3.9(1H, m), 3.1(1H, m), 2.9–2.8(2H, m), 2.7(3H, s), 1.7 (4H, s), 1.6(2H, m), 1.5(2H, m), 1.3(2H, m), 0.9(2H, m) | DMSO-$d_6$ | 473 | 12 | 63 |
| 140 | tetrahydrofuranyl | 8.8(1H, s), 7.8(1H, d), 4.8(1H, m), 4.6(2H, s), 4.3(1H, m), 4.2 (1H, m), 4.0(1H, m), 3.8–3.6 (4H, m), 3.1(1H, m), 2.9–2.7 (2H, m), 2.7(3H, s), 2.3–1.9 (2H, m), 1.3(2H, m,), 0.9(2H, m) | DMSO-$d_6$ | 475 | 12 | 42 |
| 141 | cyclopropylmethyl | 8.8(1H, s), 7.8(1H, d), 4.6 (2H, s), 4.3(1H, m), 3.9(1H, m), 3.85(2H, dd), 3.1(1H, m), 3.0– 2.8(2H, m), 2.7(3H, s), 1.3(2H, m), 1.1(1H, m), 0.9(2H, m), 0.5(2H, m), 0.3(2H, m) | DMSO-$d_6$ | 459 | 12 | 63 |
| 142 | isobutyl | 8.8(1H, s), 7.8(1H, d), 4.6(2H, s), 4.3(1H, m), 4.2(1H, m), 3.95 (1H, m), 3.8(2H, d), 3.05(1H, m), 2.9–2.7(2H, m), 2.7(3H, s), 1.9(1H, m), 1.3(2H, m), 1.0(2H, m), 0.9(6H, d) | DMSO-$d_6$ | 461 | 12 | 68 |
| 143 | propargyl | 8.8(1H, s), 7.8(1H, d), 4.62 (2H, s), 4.60(2H, s), 4.3(1H, m), 4.1(1H, m), 3.9(1H, m), 3.5 (1H, s),3.0(1H, m), 2.7(3H, s), 2.9–2.7(2H, m), 1.3(2H, m), 1.0(2H, m) | DMSO-$d_6$ | 443 | 12 | 30 |
| 144 | 3-butynyl | 8.8(1H, s), 7.8(1H, d), 4.6(2H, s), 4.3(1H, m), 4.2(1H, m), 4.15(2H, t), 3.1(1H, m), 2.9– 2.7(2H, m), 2.8(1H, s), 2.7(3H, s), 2.5(3H, t), 1.3(2H, m), 0.9(2H, m) | DMSO-$d_6$ | 457 | 12 | 52 |

TABLE 20-continued

Examples 137 to 146

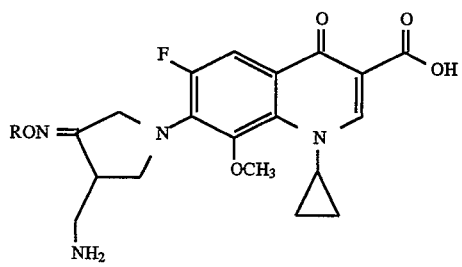

| Examp. No. | R | ¹H NMR, δ (ppm) | NMR solv. | FAB, MS (M+1) | Reac. time (hr) | Yield (%) |
|---|---|---|---|---|---|---|
| 145 | ⏘OCH₃ | 8.8(1H, s), 7.8(1H, d), 4.6(2H, s), 4.3(1H, m), 4.15(1H, m), 3.9 (1H, m), 3.3(2H, s), 3.1(3H, s), 2.9(1H, m), 2.8–2.6(2H, m), 2.7(3H, s), 1.3(2H, m), 0.9(2H, m) | DMSO-$d_6$ | 449 | 8 | 39 |
| 146 | ⏘Cl | 8.8(1H, s), 7.8(1H, d), 4.6(2H, s), 4.3(2H, t), 4.25(1H, m), 4.2 (1H, m), 3.9(1H, m), 3.8(2H, t), 2.9–2.7(2H, m), 2.7(3H, s), 1.3 (2H, m), 1.0(2H, m) | DMSO-$d_6$ | 467 | 12 | 57 |

TABLE 21

Examples 147 to 156

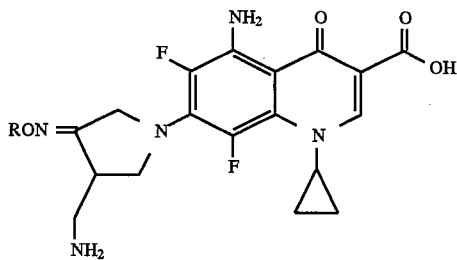

| Examp. No. | R | ¹H NMR, δ (ppm) | NMR solv. | FAB, MS (M+1) | Reac. time (hr) | Yield (%) |
|---|---|---|---|---|---|---|
| 147 | isopropyl | 8.4(1H, s), 7.7(2H, br), 4.5 (1H, m), 4.3(2H, s), 4.0–3.8 (3H, m), 3.2(1H, m), 2.8–2.6 (2H, m), 1.1(4H, s), 0.9 (6H, d) | DMSO-$d_6$ | 450 | 5 | 73 |
| 148 | cyclobutyl | 8.3(1H, s), 7.3(2H, br), 4.8 (1H, m), 4.3(2H, s), 4.0–3.8 (3H, m), 2.8–2.6(2H, m), 2.2 (2H, m), 2.1(2H, m), 1.6(1H, m), 1.5(1H, m), 1.1(4H, m) | DMSO-$d_6$ | 462 | 8 | 64 |
| 149 | cyclopentyl | 8.4(1H, s), 7.4(2H, br), 4.7 (1H, m), 4.5(2H, s), 4.2(1H, m), 3.9(1H, m), 3.7(1H, m), 3.0(1H, m), 2.8–2.6(2H, m), 1.7(4H, s), 1.6(2H, m), 1.5(2H, m), 1.1 (4H, m) | DMSO-$d_6$ | 476 | 8 | 61 |
| 150 | tetrahydrofuranyl | 8.4(1H, s), 7.4(2H, br), 4.8 (1H, m), 4.6(2H, s), 4.2(1H, m), 4.0(1H, m), 3.8–3.6(4H, m), 3.0(1H, m), 2.8–2.6(2H, m), 2.3–1.9(2H, m), 1.20–0.9(4H, m) | DMSO-$d_6$ | 478 | 12 | 54 |

TABLE 21-continued

Examples 147 to 156

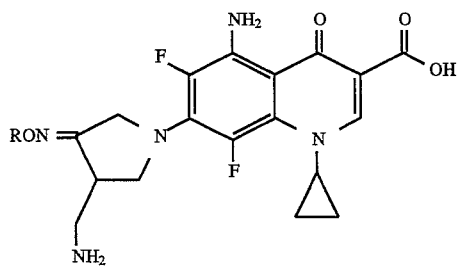

| Examp. No. | R | ¹H NMR, δ (ppm) | NMR solv. | FAB, MS (M+1) | Reac. time (hr) | Yield (%) |
|---|---|---|---|---|---|---|
| 151 | ▷—CH₂— | 8.4(1H, s), 7.5(2H, br), 4.6 (2H, s), 3.9(1H, m), 3.8(2H, dd), 3.0(1H, m), 2.9–2.8(2H, m), 1.0(1H, m), 0.5(2H, m), 0.3(2H, m) | DMSO-$d_6$ | 462 | 5 | 82 |
| 152 | (CH₃)₂CHCH₂— | 8.4(1H, s), 7.5(2H, br), 4.5 (2H, s), 3.9(1H, m), 3.8(2H, dd), 3.1(1H, m), 2.9–2.7(2H, m), 1.9(1H, m), 1.2–1.1(4H, m), 0.9(6H, d) | DMSO-$d_6$ | 464 | 6 | 75 |
| 153 | HC≡C-CH₂— | 8.4(1H, s), 7.4(2H, br), 4.6 (2H, s), 4.59(2H, m), 4.2(1H, m), 3.9(1H, m), 3.7(1H, m), 3.5 (1H, s), 3.0(1H, m), 2.8–2.6 (2H, m), 1.1(4H, s) | DMSO-$d_6$ | 446 | 4 | 50 |
| 154 | HC≡C-CH₂-CH₂— | 8.4(1H, s), 7.5(2H, br), 4.4 (2H, s), 4.1(1H, m), 4.0(2H, t), 3.9(1H, m), 3.8(1H, m), 3.1(1H, m), 2.8–2.7(2H, m), 2.8(1H, s), 2.5(2H, t), 1.2–0.9(4H, m) | DMSO-$d_6$ | 460 | 5 | 70 |
| 155 | CH₃O-CH₂-CH₂— | 8.4(1H, s), 7.4(2H, br), 4.4 (2H, s), 4.3(2H, t), 4.1(1H, m), 3.9(1H, m), 3.7(2H, t), 3.6(1H, m), 3.3(2H, s), 3.0(3H, s), 2.9 (1H, m), 2.8–2.6(2H, m), 1.3–0.9(4H, m) | DMSO-$d_6$ | 452 | 3 | 60 |
| 156 | Cl-CH₂-CH₂-CH₂— | 8.4(1H, s), 7.4(2H, br), 4.4 (2H, s), 4.3(2H, t), 4.0(2H, m), 3.9(1H, m), 3.8(2H, t), 3.7(1H, m), 3.2(1H, m), 2.9–2.7(2H, m), 1.1(4H, s) | DMSO-$d_6$ | 470 | 5 | 72 |

TABLE 22

Examples 157 to 166

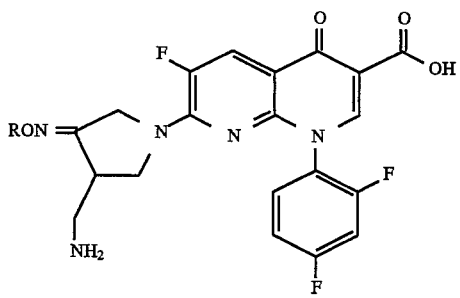

| Examp. No. | R | $^1$H NMR, δ (ppm) | NMR solv. | FAB, MS (M+1) | Reac. time (hr) | Yield (%) |
|---|---|---|---|---|---|---|
| 157 | isopropyl | 8.8(1H, s), 8.1(1H, d), 7.8(1H, m), 7.6(1H, dd), 7.3(1H, dd), 4.6(1H, m), 4.3(2H, s), 4.0(1H, m), 3.9(1H, m), 3.0(1H, m), 2.8–2.6(2H, m), 0.9(6H, d) | DMSO-$d_6$ | 490 | 15 | 64 |
| 158 | cyclobutylmethyl | 8.8(1H, s), 8.1(1H, d), 7.8(1H, m), 7.6(1H, dd), 7.3(1H, dd), 4.7(1H, m), 4.4(2H, s), 4.0(1H, m), 3.9(1H, m), 3.0(1H, m), 2.8–2.6(2H, m), 2.2(2H, m), 2.1(2H, m), 1.7(1H, m), 1.5(1H, m) | DMSO-$d_6$ | 502 | 20 | 61 |
| 159 | cyclopentylmethyl | 8.8(1H, s), 8.1(1H, d), 7.8(1H, m), 7.6(1H, dd), 7.3(1H, dd), 4.7(1H, m), 4.4(2H, s), 4.0(1H, m), 3.9(1H, m), 3.0(1H, m), 2.8–2.6(2H, m), 2.2(2H, m), 2.1(2H, m), 1.7(1H, m), 1.5(1H, m) | DMSO-$d_6$ | 516 | 35 | 70 |
| 160 | tetrahydrofuranylmethyl | 8.8(1H, s), 8.1(1H, d), 7.8(1H, m), 7.6(1H, dd), 7.3(1H, dd), 4.8(1H, m), 4.4(2H, s), 4.0(1H, m), 3.9(1H, m), 3.8–3.6(4H, m), 3.0(1H, m), 2.9–2.6(2H, m), 2.3–1.9(2H, m) | DMSO-$d_6$ | 518 | 35 | 55 |
| 161 | cyclopropylmethyl | 8.8(1H, s), 8.1(1H, d), 7.8 (1H, dd), 7.6(1H, dd), 7.3(1H, dd), 4.6(2H, s), 4.2(1H, m), 3.9(1H, m), 3.8(2H, dd), 3.0 (1H, m), 2.8–2.6(2H, m), 1.1 (1H, m), 0.5(2H, m), 0.3(2H, m) | DMSO-$d_6$ | 502 | 30 | 65 |
| 162 | isobutyl | 8.8(1H, s), 8.1(1H, d), 7.8(1H, dd), 7.6(1H, dd), 7.3(1H, dd), 4.6(2H, s), 4.0(1H, m), 3.9(1H, m), 3.8(2H, d), 3.0(1H, m), 2.8–2.6(2H, m), 1.9(1H, m), 0.9(6H, d) | DMSO-$d_6$ | 504 | 20 | 70 |
| 163 | propargyl | 8.79(1H, s) 8.01(1H, d), 7.8 (1H, m), 7.6(1H, dd), 7.3(1H, dd), 4.73(2H, s), 4.61(2H, s), 4.21(1H, m), 3.75(1H, m), 3.50 (1H, s), 3.35(2H, s), 3.08(1H, m), 2.90–2.70(2H, m) | DMSO-$d_6$ | 486 | 60 | 52 |
| 164 | but-3-ynyl | 8.8(1H, s), 8.1(1H, d), 7.8(1H, m), 7.6(1H, dd), 7.3(1H, dd), 4.6(2H, s), 4.1(1H, m), 4.0(2H, t), 3.9(1H, m), 3.0(1H, m), 2.8–2.6(2H, m), 2.7(1H, s), 2.5(2H, t) | DMSO-$d_6$ | 500 | 25 | 53 |

TABLE 22-continued

Examples 157 to 166

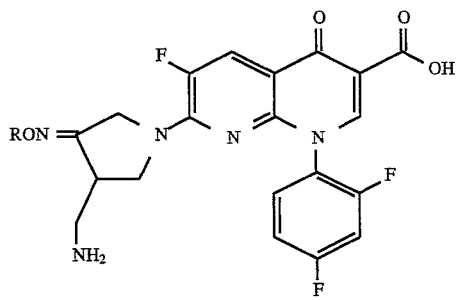

| Examp. No. | R | ¹H NMR, δ (ppm) | NMR solv. | FAB, MS (M+1) | Reac. time (hr) | Yield (%) |
|---|---|---|---|---|---|---|
| 165 | ⟋OCH₃ | 8.8(1H, s), 8.1(1H, d), 7.8(1H, m), 7.6(1H, dd), 7.3(1H, dd), 4.6(2H, s), 4.1(1H, m), 3.9(1H, m), 3.3(2H, s), 3.1(3H, s), 3.0 (1H, m), 2.8–2.6(2H, m) | DMSO-d₆ | 492 | 30 | 47 |
| 166 | ⟋⟍Cl | 8.8(1H, s), 8.1(1H, d), 7.8(1H, m), 7.6(1H, dd), 7.3(1H, m), 4.6 (2H, s), 4.3(2H, t), 4.1(1H, m), 3.9(1H, m), 3.8(2H, t), 3.1(1H, m), 2.8–2.6(2H, m) | DMSO-d₆ | 510 | 15 | 51 |

TABLE 23

Examples 167 to 176

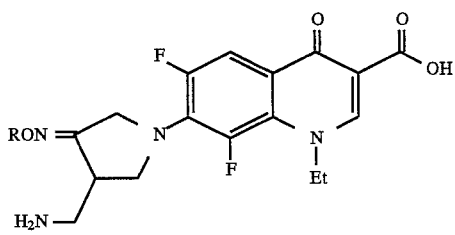

| Examp. No. | R | ¹H NMR, δ (ppm) | NMR solv. | FAB, MS (M+1) | Reac. time (hr) | Yield (%) |
|---|---|---|---|---|---|---|
| 167 | isopropyl | 8.8(1H, s), 7.8(1H, d), 4.6(1H, m), 4.5(2H, q), 4.4(2H, s), 4.2 (1H, m), 3.9(1H, ,m), 3.1(1H, m), 2.9–2.7(2H, m), 1.45(3H, t), 0.9(6H, d) | DMSO-d₆ | 423 | 4.5 | 82 |
| 168 | cyclobutyl | 8.8(1H, s), 7.8(1H, d), 4.7(1H, m), 4.5(2H, q), 4.4(2H, s), 4.2 (1H, m), 4.1(1H, m), 3.1(1H, m), 2.9–2.7(2H, m), 2.2(2H, m), 2.1 (2H, m), 1.7(1H, m), 1.6(1H, m), 1.45(3H, t) | DMSO-d₆ | 435 | 5 | 73 |
| 169 | cyclopentyl | 8.8(1H, s), 7.8(1H, d), 4.75 (1H, m), 4.6(2H, s), 4.5(2H, q), 4.2(1H, m), 3.9(1H, m), 3.0–2.7 (2H, m), 1.8(4H, s), 1.65(2H, s), 1.5(2H, s), 1.4(3H, t) | DMSO-d₆ | 449 | 5 | 77 |
| 170 | tetrahydrofuranyl | 8.7(1H, s), 7.8(1H, d), 4.8(1H, m), 4.55(2H, s), 4.5(2H, dd), 4.15(1H, m), 3.85(1H, m), 3.7 (2H, m), 3.1(1H, m), 2.9–2.7 (2H, m), 2.1–1.9(2H, m), 1.5 (3H, t) | DMSO-d₆ | 451 | 6 | 71 |

TABLE 23-continued

Examples 167 to 176

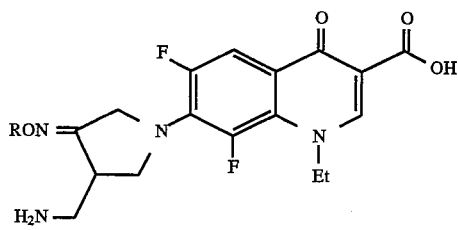

| Examp. No. | R | ¹H NMR, δ (ppm) | NMR solv. | FAB, MS (M+1) | Reac. time (hr) | Yield (%) |
|---|---|---|---|---|---|---|
| 171 | cyclopropyl | 8.8(1H, s), 7.8(1H, d), 4.6 (2H, s), 4.45(2H, m), 4.25(1H, m), 3.9(2H, dd), 3.7(1H, m), 3.1(1H, m), 1.45(3H, t), 0.5 (2H, m), 0.25(2H, m) | DMSO-$d_6$ | 435 | 5 | 84 |
| 172 | isopropyl | 8.8(1H, s), 7.8(1H, d), 4.6(2H, s), 4.5(2H, q), 4.2(1H, m), 3.9 (1H, m), 3.85(2H, dd), 3.1(1H, m), 2.9–2.7(2H,m), 1.9(1H, m), 0.9(6H, d) | DMSO-$d_6$ | 437 | 4 | 70 |
| 173 | propargyl | 8.8(1H, s), 7.8(1H, d), 4.62 (2H, s), 4.5(2H, q), 4.4(2H, s), 4.2(1H, m), 3.9(1H, m), 3.5(1H, s), 3.1(1H, m), 2.9–2.7(2H, m), 1.45(3H, t) | DMSO-$d_6$ | 419 | 3 | 50 |
| 174 | butynyl | 8.8(1H, s), 7.8(1H, d), 4.5(2H, dd), 4.2(1H, m), 4.15(2H, t), 3.9(1H, m), 3.1(1H, m), 2.9–2.7(2H, m), 2.8(1H, s), 2.5(2H, t), 1.5(3H, t) | DMSO-$d_6$ | 433 | 4.5 | 72 |
| 175 | $-CH_2CH_2OCH_3$ | 8.8(1H, s), 7.8(1H, d), 4.6(2H, s), 4.5(2H, dd), 4.15(1H, m), 3.9(1H, m), 3.3(2H, s), 3.1(3H, s), 2.9(1H, m), 2.8(1H, m), 2.6 (1H, m), 1.5(3H, t) | DMSO-$d_6$ | 425 | 2 | 39 |
| 176 | $-CH_2CH_2Cl$ | 8.8(1H, s), 7.8(1H, d), 4.6(2H, s), 4.5(2H, dd), 4.3(2H, t), 4.2 (1H, m), 3.9(1H, m), 3.8(2H, t), 2.9–2.7(2H, m), 1.5(3H, t) | DMSO-$d_6$ | 443 | 2 | 57 |

EXAMPLE 177

Synthesis of 7-(4-amino-3-methoxyimino-pyrrolidin-1-yl)-1-cyclopropyl-6,8-difluoro-4-oxo-1,4-dihydroquinoline-3-carboxylic acid

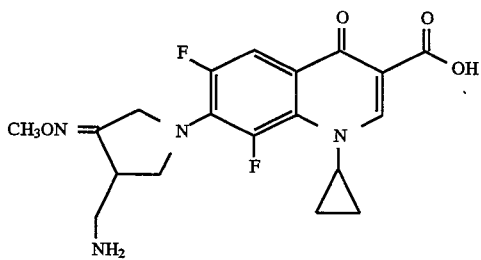

2.83 g (10 mmole) of 1-cyclopropyl-6,7,8-trifluoro-4-oxo-1,4-dihydroquinoline-3-carboxylic acid and 4.27 g (11.5 mmole) of 4-aminomethyl-pyrrolidin-3-one O-methyloxime ditrifluoroacetate were added to 23 ml of dry acetonitrile. Then, 4.6 g (30 mmole) of 1,8-diazabicyclo[5.4.0]undec-7-ene was added thereto and the mixture was refluxed for 1.5 hours under heating and then cooled down to room temperature. 15 ml of distilled water was added to the reaction solution. The precipitated solid product was separated and dried to obtain 2.24 g (Yield: 55%) of the title compound.

¹H NMR (DMSO-$d_6$, ppm): δ8.6(1H, s), 7.75(1H, d), 4.35(2H, s), 4.1–3.9(2H, m), 3.8(3H, s), 3.7(1H, m), 3.35 (1H, m), 2.9–2.6(2H, m), 1.25 (2H, d), 0.95(2H, s)

FAB MS (POS): [H+H]=407

EXAMPLE 178

Synthesis of 7-(4-aminomethyl-3-methoxyiminopyrrolidin-1-yl)-8-chloro-1-cyclopropyl-6-fluoro-4-oxo-1,4-dihydroquinoline-3-carboxylic acid

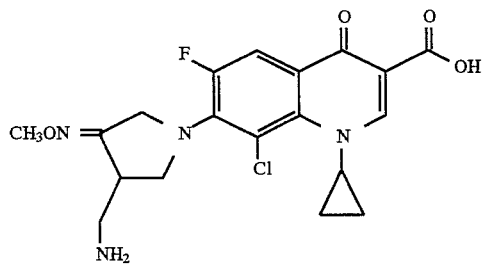

141 mg (0.5 mmole) of 1-cyclopropyl-8-chloro-6,7-difluoro-4-oxo-1,4-dihydroquinoline-3-carboxylic acid and 205 mg (0.55 mmole) of 4-aminomethylpyrrolidin-3-one O-methyloxime ditrifluoroacetate were reacted for one hour according to the same manner as Example 177. Then, the reaction solution was concentrated and the residue was purified with preparative HPLC to obtain 88 mg (Yield: 42%) of the title compound.

$^1$H NMR (DMSO-$d_6$, ppm): δ8.7(1H, s), 7.85(1H, d), 4.4 (1H, m), 3.75(3H, s), 3.7(3H, m), 3.4(2H, m), 3.0–2.7(2H, m), 1.25(2H, d), 1.0(2H, s)

FAB MS (POS): [M+H]=423

EXAMPLE 179

Synthesis of 7-(4-aminomethyl-3-methoxyiminopyrrolidin-1-yl)-1-cyclopropyl-6-fluoro-4-oxo-1,4-dihydroquinoline-3-carboxylic acid

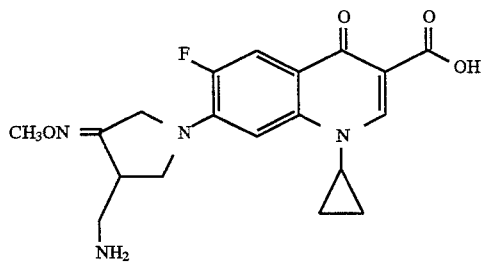

132 mg (0.5 mmole) of 1-cyclopropyl-6,7-difluoro-4-oxo-1,4-dihydroquinoline-3-carboxylic acid and 205 mg (0.55 mmole) of 4-aminomethylpyrrolidin-3-one O-methyloxime ditrifluoroacetate were reacted for 3 hours according to the same manner as Example 177. Then, the reaction solution was concentrated and the residue was purified with preparative HPLC to obtain 73 mg (Yield: 37%) of the title compound.

$^1$ H NMR (DMSO-$d_6$, ppm): δ8.6(1H, s), 7.85(1H, d), 7.2(1H, d), 4.4(2H, d), 3.9(1H, m), 3.85(3H, s), 3.8–3.65 (2H, m), 3.0(1H, m), 2.9–2.7(2H, m), 1.3 (2H, m), 1.1(2H, m)

FAB MS (POS): [M+H]=389

EXAMPLE 180

Synthesis of 7-(4-aminomethyl3-methoxyiminopyrrolidin-1-yl)-1-cyclopropyl-6-fluoro-4-oxo-1,4-dihydro[1,8]naphthyridine-3-carboxylic acid

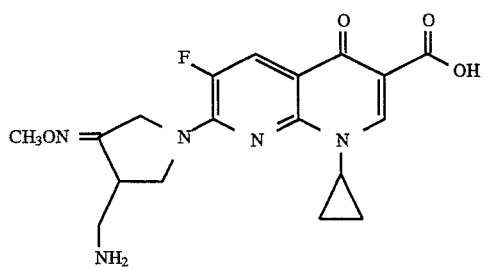

141 mg (0.5 mmole) of 1-cyclopropyl-7-chloro-6-fluoro-4-oxo-1,4-dihydro[1,8]naphthyridine-3-carboxylic acid and 205 mg (0.5 mmole) of 4-aminomethylpyrrolidin-3-one O-methyloxime ditrifluoroacetate were reacted for 0.5 hour according to the same manner as Example 177 to obtain 167 mg (Yield: 85%) of the title compound.

$^1$H NMR (DMSO-$d_6$, ppm): δ8.6(1H, s), 8.05(1H, d) , 4.55(2H, s), 4.3(1H, m), 3.85(3H, s, 1H, m), 3.7 (1H, m), 3.1–3.0(2H, m), 1.2–1.0(4H, m)

FAB MS(POS): [M+H]=390

EXAMPLE 181

Synthesis of 7-(4-aminomethyl-3-methoxyiminopyrrolidin-1-yl)-1-(2,4-difluorophenyl)-6-fluoro-4-oxo-1,4-dihydro[1,8] naphthyridine-3-carboxylic acid

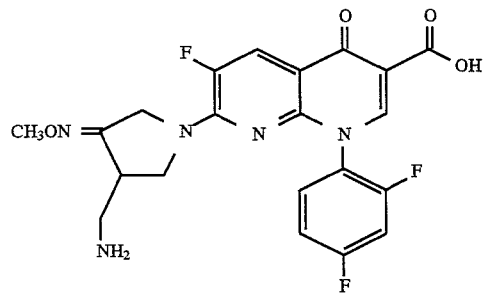

177 mg (0.5 mmole) of 1-(2,4-difluorophenyl)-7-chloro-6-fluoro-4-oxo-1,4-dihydro[1,8]naphthyridine-3-carboxylic acid and 205 mg (0.55 mmole) of 4-aminomethylpyrrolidin-3-one O-methyloxime ditrifluoroacetate were reacted for 0.5 hour according to the same manner as Example 177 to obtain 59 mg (Yield: 25%) of the title compound.

$^1$H NMR (DMSO-$d_6$, ppm): δ8.85(1H, s), 8.05(1H, d), 7.75(1H, dd), 7.6(1H, dd), 7.35(1H, dd), 4.3(2H, m), 3.8(3H, s, 1H, m), 3.6(1H, m), 3.0 (1H, m), 2.7(2H, m)

FAB MS (POS): [M+H]=462

EXAMPLE 182

Synthesis of 1-cyclopropyl-5-amino-6,8-difluoro-7-(4-aminomethyl-3-methyloxyiminopyrrolidin-1-yl)-4-oxo-1,4-dihydroquinoline-3-carboxylic acid

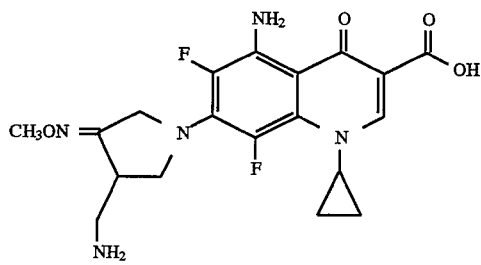

148 mg (0.5 mmole) of 1-cyclopropyl-5-amino-6,7,8-trifluoro-4-oxo-1,4-dihydroquinoline-3-carboxylic acid and 205 mg (0.55 mmole) of 4-aminomethylpyrrolidin-3-one O-methyloxime ditrifluoroacetate were refluxed for 4 hours under heating according to the same manner as Example 177. Then, the reaction solution was concentrated and the residue was purified with preparative HPLC to obtain 84 mg (Yield: 40%) of the title compound.

$^1$H NMR (DMSO-d$_6$, ppm): δ8.49(1H, s), 7.28(2H, bs), 4.3(2H, s), 3.9(2H, m), 3.8(3H, s), 3.7(1H, m), 2.6–2.8(3H, m), 1.05(4H, m)

FAB MS(POS): [M+H]$^+$=422

EXAMPLES 183 to 202

The compounds prepared in Preparations 40 and 55 to 57 were treated according to the same procedure as Example 177 to 182 to prepare the respective compounds 183 to 202 of which NMR and NS data are listed in the following Table 24.

TABLE 24

Examples 183 to 202

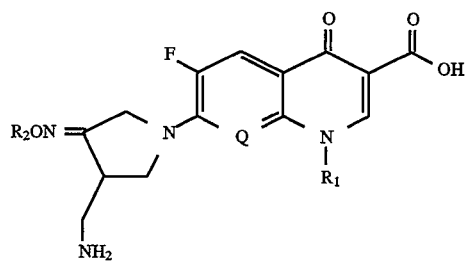

| Ex. No. | Q | R$_1$ | R$_2$ | $^1$H NMR (DMSO-d$_6$) δ (ppm) | FAB MS (POS) [M+H] | Reac. Time (hr) | Yield (%) |
|---|---|---|---|---|---|---|---|
| 183 | CF | cyclopropyl | H | 8.8(1H, s), 7.9(1H, d), 4.35(1H, m), 3.8(2H, m), 3.7(2H, m), 3.4 (1H, m), 3.0(2H, m), 1.2–1.0 (4H, m) | 393 | 2.5 | 41 |
| 184 | CF | cyclopropyl | Et | 8.8(1H, s), 7.9(1H, d), 4.4(1H, m), 4.2(2H, q), 4.1–3.9(2H, m), 3.4(2H, m), 2.8(2H, m), 1.4(3H, t), 1.25–1.0(4H, m) | 421 | 2 | 38 |
| 185 | CF | cyclopropyl | Ph | 8.8(1H, s), 7.9(1H, d), 7.3–7.1 (5H, m), 4.3(1H, m), 3.9–3.7(3H, m), 3.4(2H, m), 2.8(2H, m), 1.2 (2H, d), 1.05(2H, s) | 469 | 4 | 29 |
| 186 | CF | cyclopropyl | tBu | 8.8(1H, s), 7.9(1H, d), 4.35(1H, d), 4.1–3.9(3H, m), 3.4(2H, m), 2.9–2.7(2H, m), 1.35(9H, s), 1.2–0.95(4H, m) | 449 | 2 | 35 |
| 187 | CCl | cyclopropyl | H | 8.9(1H, s), 7.9(1H, d), 4.4(1H, m), 3.8(2H, m), 3.7(2H, m), 3.4 (1H, m), 2.9(2H, m), 1.25(2H, m), 1.1(2H, s) | 409 | 1.5 | 39 |
| 188 | CCl | cyclopropyl | Et | 8.9(1H, s), 7.9(1H, d), 4.35 (1H, m), 4.2(2H, q), 3.95–3.75 (3H, m), 3.7(2H, m), 3.4(2H, m), 2.85–2.7(2H, m), 1.4(3H, t), 1.3–1.15(4H, m) | 437 | 1.5 | 37 |

TABLE 24-continued

Examples 183 to 202

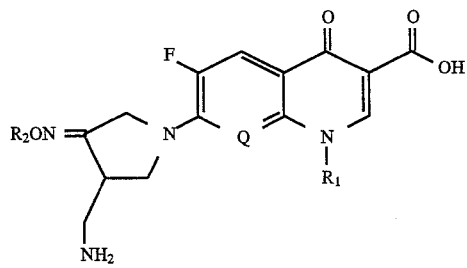

| Ex. No. | Q | R₁ | R₂ | ¹H NMR (DMSO-d₆) δ (ppm) | FAB MS (POS) [M+H] | Reac. Time (hr) | Yield (%) |
|---|---|---|---|---|---|---|---|
| 189 | CCl | ◁ | Ph | 8.9(1H, s), 7.9(1H, d), 7.3–7.1 (5H, m), 4.35(1H, m), 4.1–3.9 (3H, m), 3.65(2H, m), 3.35(2H, m), 2.8–2.7(2H, m), 1.15(2H, d), 0.95(2H, s) | 485 | 4.5 | 25 |
| 190 | CCl | ◁ | tBu | 8.9(1H, s), 7.85(1H, d), 4.3(1H, m), 3.95–3.8(3H, m), 3.7(2H, m), 3.4(2H, m), 2.8(2H, m), 1.3(9H, s), 1.2–1.0(4H, m) | 465 | 3 | 51 |
| 191 | CH | ◁ | H | 8.6(1H, s), 7.85(1H, d), 7.2(1H, d), 4.4(1H, m), 3.9(2H, m), 3.8–3.65(3H, m), 2.9–2.7(2H, m), 1.3 (2H, d), 1.1(2H, s) | 375 | 2.2 | 42 |
| 192 | CH | ◁ | Et | 8.6(1H, s), 7.8(1H, d), 7.2(1H, d), 4.4(1H, m), 4.25(2H, q), 3.9–3.7(3H, m), 3.5(2H, m), 2.9–2.7 (2H, m), 1.3(3H, t), 1.25–0.95 (4H, m) | 403 | 1.5 | 40 |
| 193 | CH | ◁ | Ph | 8.6(1H, s), 7.8(1H, d), 7.5–7.2 (5H, m, 1H, d), 4.35(1H, m), 4.0–3.8(3H, m), 3.5(2H, m), 2.85–2.7 (2H, m), 1.3(2H, d), 1.15(2H, s) | 451 | 4.5 | 31 |
| 194 | CH | ◁ | tBu | 8.6(1H, s), 7.75(1H, d), 7.2(1H, d), 4.35(1H, m), 4.0–3.8(3H, m), 3.5(2H, m), 2.9–2.7(2H, m), 1.4 (9H, s), 1.2–1.05(4H, m) | 431 | 3 | 43 |
| 195 | N | ◁ | H | 8.6(1H, s), 8.1(1H, d), 4.5(2H, s), 4.3(1H, m), 3.8(1H, m), 3.65 (1H, m), 3.35(1H, m), 3.0–2.9 (2H, m), 1.2–1.0(4H, m) | 376 | 1 | 61 |
| 196 | N | ◁ | Et | 8.6(1H, s), 8.05(1H, d), 4.55 (2H, s), 4.3(1H, m), 4.25(2H, q), 3.8(1H, m), 3.7(1H, m), 3.4 (1H, m), 3.0–2.85(2H, m), 1.35 (3H, t), 1.2–0.95(4H, m) | 404 | 1 | 57 |
| 197 | N | ◁ | Ph | 8.6(1H, s), 8.1(1H, d), 7.7–7.3 (5H, m), 4.6(2H, s), 4.35(1H, m), 3.9(1H, m), 3.75(1H, m,), 3.4(1H, m), 3.05–2.8(3H, m), 1.25(2H, d), 1.05(2H, s) | 452 | 1 | 40 |
| 198 | N | ◁ | tBu | 8.6(1H, s), 8.05(1H, d), 4.55 (2H, s), 4.35(1H, m), 3.95(1H, m), 3.7(1H, m), 3.35(1H, m), 3.0–2.85(2H, m), 1.35(9H, s), 1.15 (2H, d), 1.0(2H, s) | 432 | 1.5 | 54 |

TABLE 24-continued

Examples 183 to 202

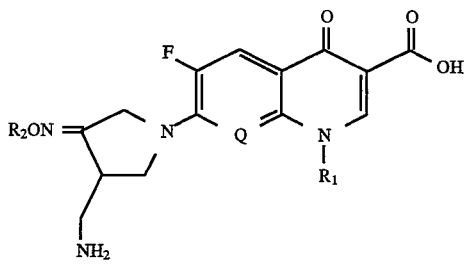

| Ex. No. | Q | R₁ | R₂ | ¹H NMR (DMSO-d₆) δ (ppm) | FAB MS (POS) [M+H] | Reac. Time (hr) | Yield (%) |
|---|---|---|---|---|---|---|---|
| 199 | N | 2,4-difluorophenyl | H | 8.85(1H, s), 8.1(1H, d), 7.75 (1H, m), 7.6(1H, dd), 7.35(1H, dd), 4.3(1H, m), 3.8(3H, m), 3.6 (1H, m), 3.0(1H, m), 2.7(2H, m) | 448 | 1 | 33 |
| 200 | N | 2,4-difluorophenyl | Et | 8.85(1H, s), 8.05(1H, d), 7.75 (1H, m), 7.6(1H, dd), 7.35(1H, dd), 4.3(1H, m), 4.25(2H, q), 3.75(3H, m), 3.6(2H, m), 2.95 (2H, m), 2.7–2.6(2H, m), 1.4 (3H, t) | 476 | 1 | 37 |
| 201 | N | 2,4-difluorophenyl | Ph | 8.85(1H, s), 8.1(1H, d), 7.75 (1H, m), 7.6(1H, dd), 7.55–7.35 (5H, m, 1H, dd), 4.35(1H, m), 3.75 (3H, m), 3.65(2H, m), 3.0(2H, m), 2.85(2H, m) | 524 | 1.5 | 29 |
| 202 | N | 2,4-difluorophenyl | tBu | 8.85(1H, s), 8.05(1H, d), 7.75 (1H, m), 7.55(1H, dd), 7.3(1H, dd), 4.3(1H, m), 3.8(3H, m), 3.55 (2H, m), 2.9(2H, m), 2.7–2.65 (2H, m), 1.3(9H, s) | 504 | 0.5 | 41 |

Biological Example 1

In vitro antibacterial activity test

The antibacterial activity of the compounds according to the present invention was determined by measuring their minimum inhibitory concentrations (MIC, μg/ml) against standard strains, clinically isolated strains and strains resistant to some antibacterial agents. In this test, the known antibacterial compounds, ofloxacin and ciprofloxacin, were used as the comparative agents. The minimum inhibitory concentration could be determined by diluting the test compounds according to a two-times dilution method, dispersing the diluted test compounds in Mueller-Hinton agar medium and then inoculating 5 μl of the standard strain having $10^7$ CFU per ml to the medium, which is then incubated for 18 hours at 37° C. The measured results are described in the following Table 25.

TABLE 25

Minimum Inhibitory Concentration of the test compounds (μg/ml)

| Test Strains | Examples | | | | |
|---|---|---|---|---|---|
| | 1 | 12 | 34 | 56 | 89 |
| Staphylococcus aureus 6538p | ≦0.008 | ≦0.008 | ≦0.008 | ≦0.008 | ≦0.008 |
| Staphylococcus aureus giorgio | ≦0.008 | ≦0.008 | ≦0.008 | ≦0.008 | ≦0.008 |
| Staphylococcus aureus 77 | ≦0.008 | ≦0.008 | ≦0.008 | ≦0.008 | ≦0.008 |
| Staphylococcus aureus 241 | 2 | 1 | 4 | 2 | 1 |
| Staphylococcus epidermidis 887E | ≦0.008 | ≦0.008 | ≦0.008 | ≦0.008 | ≦0.008 |
| Staphylococcus epidermidis 178 | 2 | 0.5 | 2 | 2 | 0.5 |
| Streptococcus faecalis 29212 | 0.031 | 0.031 | 0.13 | 0.016 | 0.063 |
| Bacillus subtilis 6633 | ≦0.008 | ≦0.008 | ≦0.008 | ≦0.008 | ≦0.008 |
| Micrococcus luteus 9341 | 0.063 | 0.13 | 0.13 | 0.063 | 0.25 |
| Escherichia coli 10536 | ≦0.008 | ≦0.008 | 0.016 | ≦0.008 | 0.016 |
| Escherichia coli 3190Y | ≦0.008 | 0.016 | ≦0.008 | ≦0.008 | 0.016 |

TABLE 25-continued

Minimum Inhibitory Concentration of the test compounds (μg/ml)

| | | | | | |
|---|---|---|---|---|---|
| Escherichia coli 851E | 0.016 | 0.063 | 0.13 | ≦0.008 | 0.063 |
| Escherichia coli TEM3 3455E | 0.25 | 0.5 | 1 | 0.5 | 0.25 |
| Escherichia coli TEM5 3739E | 0.063 | 0.25 | 0.5 | 0.25 | 0.13 |
| Escherichia coli TEM9 2639E | 0.063 | 0.25 | 0.13 | 0.063 | 0.063 |
| Pseudomonas aeruginosa 1912E | 1 | 2 | 0.5 | 2 | 2 |
| Pseudomonas aeruginosa 10145 | 2 | 0.5 | 2 | 2 | 2 |
| Acinetobacter calcoaceticus 15473 | ≦0.008 | 0.016 | 0.031 | ≦0.008 | 0.031 |
| Citrobacter diversus 2046E | 0.063 | 0.13 | 0.25 | 0.016 | 0.13 |
| Enterobacter cloacae 1194E | 0.031 | 0.13 | 0.25 | 0.031 | 0.13 |
| Enterobacter cloacae P99 | ≦0.008 | 0.063 | 0.063 | ≦0.008 | 0.016 |
| Klebsiella aerogenes 1976E | 0.25 | 1 | 0.5 | 0.5 | 0.5 |
| Klebsiella aerogenes 1082E | 0.063 | 0.13 | 0.031 | 0.016 | 0.25 |
| Salmonella typhimurium 14028 | 0.13 | 0.25 | 0.063 | 0.031 | 0.13 |

| | Examples | | | | |
|---|---|---|---|---|---|
| Test Strains | 97 | 102 | 103 | 104 | 177 |
| Staphylococcus aureus 6538p | ≦0.008 | 0.016 | ≦0.008 | ≦0.008 | ≦0.008 |
| Staphylococcus aureus giorgio | ≦0.008 | ≦0.008 | ≦0.008 | ≦0.008 | ≦0.008 |
| Staphylococcus aureus 77 | 0.016 | 0.016 | ≦0.008 | ≦0.008 | 0.016 |
| Staphylococcus aureus 241 | 2 | 4 | 4 | 8 | 0.5 |
| Staphylococcus epidermidis 887E | ≦0.008 | ≦0.008 | ≦0.008 | 0.016 | ≦0.008 |
| Staphylococcus epidermidis 178 | 1 | 1 | 4 | 4 | 1 |
| Streptococcus faecalis 29212 | 0.063 | 0.063 | 0.031 | 0.031 | 0.031 |
| Bacillus subtilis 6633 | ≦0.008 | ≦0.008 | ≦0.008 | ≦0.008 | ≦0.008 |
| Micrococcus luteus 9341 | 0.063 | 0.063 | 0.13 | 0.13 | 0.063 |
| Escherichia coli 10536 | ≦0.008 | ≦0.008 | ≦0.008 | ≦0.008 | ≦0.008 |
| Escherichia coli 3190Y | ≦0.008 | ≦0.008 | ≦0.008 | ≦0.008 | ≦0.008 |
| Escherichia coli 851E | 0.031 | 0.063 | ≦0.008 | ≦0.008 | 0.031 |
| Escherichia coli TEM3 3455E | 0.13 | 0.5 | 0.13 | 0.25 | 0.25 |
| Escherichia coli TEM5 3739E | 0.063 | 0.25 | 0.063 | 0.13 | 0.13 |
| Escherichia coli TEM9 2639E | 0.031 | 0.063 | 0.031 | 0.031 | 0.063 |
| Pseudomonas aeruginosa 1912E | 1 | 2 | 0.5 | 1 | 0.5 |
| Pseudomonas aeruginosa 10145 | 1 | 2 | 0.5 | 1 | 0.5 |
| Acinetobacter calcoaceticus 15473 | 0.016 | 0.063 | 0.031 | ≦0.008 | 0.13 |
| Citrobacter diversus 2046E | 0.063 | 0.13 | 0.13 | ≦0.008 | 0.031 |
| Enterobacter cloacae 1194E | 0.063 | 0.25 | 0.016 | ≦0.008 | 0.063 |
| Enterobacter cloacae P99 | ≦0.008 | 0.031 | ≦0.008 | 0.016 | 0.016 |
| Klebsiella aerogenes 1976E | 0.25 | 0.5 | 0.063 | 0.13 | 0.13 |
| Klebsiella aerogenes 1082E | 0.13 | 0.25 | 0.031 | 0.031 | 0.063 |
| Salmonella typhimurium 14028 | 0.13 | 0.25 | 0.031 | 0.031 | 0.063 |

TABLE 25-continued

Minimum Inhibitory Concentration of the test compounds (μg/ml)

| | Examples | | | | |
|---|---|---|---|---|---|
| Test Strains | 178 | 179 | 180 | OFLX | CFLX |
| Staphylococcus aureus 6538p | 0.031 | ≦0.008 | ≦0.008 | 0.25 | 0.13 |
| Staphylococcus aureus giorgio | 0.016 | 0.016 | ≦0.008 | 0.25 | 0.25 |
| Staphylococcus aureus 77 | 0.031 | 0.031 | ≦0.008 | 0.25 | 0.25 |
| Staphylococcus aureus 241 | 1 | 2 | 2 | 64 | 64 |
| Staphylococcus epidermidis 887E | 0.063 | 0.031 | 0.063 | 2 | 0.5 |
| Staphylococcus epidermidis 178 | 1 | 2 | 2 | 32 | 128 |
| Streptococcus faecalis 29212 | 0.063 | 0.031 | 0.063 | 2 | 0.5 |
| Bacillus subtilis 6633 | 0.016 | ≦0.008 | ≦0.008 | 0.063 | 0.031 |
| Micrococcus luteus 9341 | 0.25 | 0.13 | 0.13 | 2 | 2 |
| Escherichia coli 10536 | 0.031 | ≦0.008 | ≦0.008 | 0.031 | ≦0.008 |
| Escherichia coli 3190Y | 0.016 | ≦0.008 | ≦0.008 | 0.016 | ≦0.008 |
| Escherichia coli 851E | 0.063 | ≦0.008 | ≦0.008 | 0.063 | 0.016 |
| Escherichia coli TEM3 3455E | 1 | 0.13 | 0.25 | 0.5 | 0.25 |
| Escherichia coli TEM5 3739E | 0.5 | 0.063 | 0.13 | 0.5 | 0.13 |
| Escherichia coli TEM9 2639E | 0.25 | 0.031 | 0.031 | 0.063 | 0.031 |
| Pseudomonas aeruginosa 1912E | 0.5 | 0.25 | 0.25 | 0.5 | 0.31 |
| Pseudomonas aeruginosa 10145 | 1 | 0.25 | 0.25 | 2 | 0.25 |
| Acinetobacter calcoaceticus 15473 | 0.13 | 0.016 | 0.063 | 0.25 | 0.25 |
| Citrobacter diversus 2046E | 0.13 | 0.031 | 0.016 | 0.063 | 0.016 |
| Enterobacter cloacae 1194E | 0.13 | 0.031 | 0.031 | 0.063 | 0.031 |
| Enterobacter cloacae P99 | 0.063 | 0.008 | ≦0.008 | ≦0.008 | ≦0.008 |
| Klebsiella aerogenes 1976E | 0.5 | 0.13 | 0.13 | 0.25 | 0.13 |
| Klebsiella aerogenes 1082E | 0.25 | 0.031 | 0.016 | 0.063 | ≦0.008 |
| Salmonella typhimurium 14028 | 0.063 | 0.063 | 0.031 | 0.13 | 0.031 |

Note)
OFLX = Ofloxacin
CFLX = Ciprofloxacin

Biological Example 2

Pharmacokinetic test

The pharmacokinteic property parameters of the compounds of the present invention were determined using SD rats (male) weighing about 230±10 g. Specifically, the test compounds of the present invention were administered in an amount of 20 mg/kg of body weight to test rats via femoral veins. Then, bloods were collected at certain intervals after administration of the test compounds from femoral veins and analyzed by means of Agar Well Method to measure the blood concentration of the test compounds from which pharmacokinetic parameters, half life ($T_{1/2}$) and AUC (area under the curve) were calculated. The obtained results are described in the following Table 26.

TABLE 26

| | Route | $T_{1/2}$ (hr) | $C_{max}$ (μg/ml) | $T_{max}$ (hr) | F (%) |
|---|---|---|---|---|---|
| CFLX | IV | 1.76 ± 0.035 | | | 71 |
| | PO | 1.7 ± 0.108 | 1.34 ± 0.368 | 1.13 ± 0.605 | |
| EX. 89 | IV | 2.29 ± 1.13 | | | >100 |
| | PO | 6.69 ± 2.78 | 4.89 ± 2.23 | 2.18 ± 0.77 | |
| EX. 177 | IV | 1.92 ± 0.38 | | | 47.23 |
| | PO | 3.93 ± 1.31 | 0.37 ± 0.11 | 0.51 ± 0.33 | |

Note:
CFLX = Ciprofloxacin
IV = Intravenous
PO = Per oral
$T_{1/2}$ = Biological half life
$C_{max}$ = Maximum blood concentration
$T_{max}$ = Time showing maximum blood concnetration after administration of the test compound
F = Bioavailability Biological Example 3

Acute oral toxicity test

To determine the acute oral toxicity of the compounds prepared in Examples 1 and 34, the test solution containing the compounds in various concentrations were orally administered to ICR male mouse in an amount of 10 ml per kg of body weight. For 7 days after administration, the lethality and the conditions of test mouse were observed, from which LD50 value (mg/kg) was calculated. The obtained results are described in the following Table 27.

TABLE 27

| Toxicity | |
|---|---|
| Test Compound (Example No.) | $LD_{50}$ value (mg/kg) |
| 1 | >3,000 |
| 34 | >3,000 |

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A naphthyridine carboxylic acid compound represented by the following formula (I):

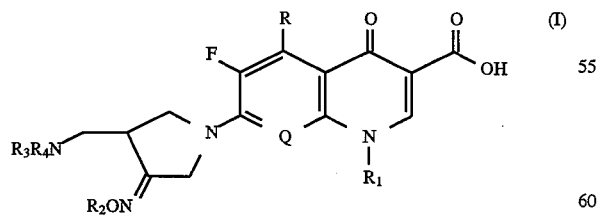

and its pharmaceutically acceptable non-toxic salt, its physiologically hydrolyzable ester, solvate and isomer, in which
R represents hydrogen, methyl or amino;
Q represents N;
$R_1$ represents cyclopropyl, ethyl, or phenyl which is substituted with one or more fluorine atom(s);
$R_2$ represents one of the following a) through e):
  a) hydrogen, straight or branched $C_1$-$C_4$ alkyl, cyclopropyl, cyclopropylmethyl, $C_3$-$C_6$ alkynyl, 2-haloethyl, methoxymethyl, methoxycarbonylmethyl, aryl or allyl,
  b) a group of the following formula (1),

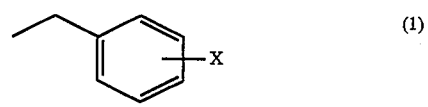

wherein X represents hydrogen, 2, 3 or 4-fluoro, cyano, nitro, methoxy, $C_1$-$C_4$ alkyl, or 2,4-difluoro,
  c) a group of the following formula (2),

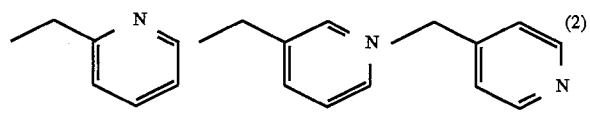

d) a heteroarylmethyl of the following formula (3),

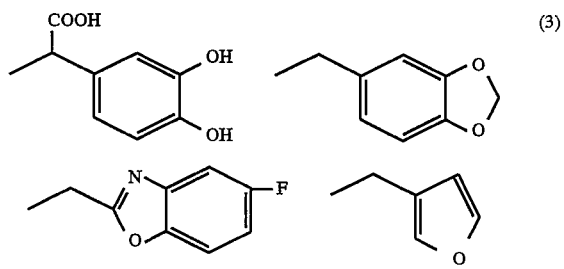

e) a group of the following formula (4),

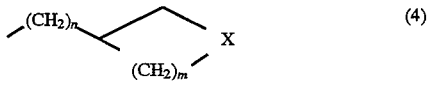

wherein n denotes 0 or 1, m denotes 0, 1 or 2 and X represents methylene, O or N, and
$R_3$ and $R_4$ independently of one another represent hydrogen or $C_1$-$C_3$ alkyl or $R_3$ and $R_4$ together with a nitrogen atom to which they are attached can form a ring.

2. The compound of claim 1, wherein Q represents N, R represents hydrogen or amino, $R_1$ represents cyclopropyl or 2,4-difluorophenyl, and $R_2$ represents hydrogen, methyl, isopropyl, t-butyl, phenyl, homopropargyl, 2-fluoroethyl, benzyl, 2-fluorobenzyl, 2-methylbenzyl or 2-methoxybenzyl.

3. The compound of claim 2, wherein Q represents N, R represents hydrogen or amino, $R_1$ represents cyclopropyl and $R_2$ represents methyl, t-butyl, homopropargyl, 2-fluoroethyl, benzyl, 2-fluorobenzyl or 2-methoxybenzyl.

4. The compound of anyone of claims 1 to 3, wherein $R_3$ and $R_4$ are hydrogen.

5. An antibacterial composition comprising as an active component the compound of formula (I) as defined in claim 1, together with a pharmaceutically acceptable carrier.

6. The composition of claim 5 comprising 1 to 100 mg of the compound of formula (I) in a unit dosage form.

* * * * *